(12) United States Patent
Ejima et al.

(10) Patent No.: US 6,169,086 B1
(45) Date of Patent: Jan. 2, 2001

(54) PYRAZOLE DERIVATIVES

(75) Inventors: Akio Ejima; Satoru Ohsuki; Hitoshi Ohki; Hiroyuki Naito, all of Tokyo (JP)

(73) Assignee: Daiichi Pharmaceutical Co., Ltd., Tokyo (JP)

( * ) Notice: Under 35 U.S.C. 154(b), the term of this patent shall be extended for 0 days.

(21) Appl. No.: 09/359,419

(22) Filed: Jul. 23, 1999

Related U.S. Application Data

(63) Continuation-in-part of application No. PCT/JP98/00300, filed on Jan. 26, 1998.

(30) Foreign Application Priority Data

Jan. 27, 1997 (JP) .................................................. 9-012116
Jul. 24, 1998 (JP) ................................................ 10-208807

(51) Int. Cl.$^7$ ...................... C07D 231/12; C07D 401/04; C07D 417/04; A61K 31/495; A61K 31/505
(52) U.S. Cl. .......................... 514/245; 544/357; 544/371; 544/367; 544/392; 544/295; 544/198; 544/364; 514/252
(58) Field of Search ..................... 544/357, 371, 544/367, 392, 295, 198, 364; 514/252, 245

(56) References Cited

FOREIGN PATENT DOCUMENTS 62-205058   9/1987 (JP) .......................... C07D 207/335
63-88179    4/1988 (JP) ............................ C07D 405/14
WO 98/32739 * 7/1998 (JP) .

* cited by examiner

Primary Examiner—Mukund J. Shah
Assistant Examiner—Hong Liu
(74) Attorney, Agent, or Firm—Sughrue, Mion, Zinn, Macpeak & Seas, PLLC

(57) ABSTRACT

The present invention relates to cis- and trans-forms of pyrazole derivatives, salts thereof, or agents containing the same, and represented by the general formula (I):

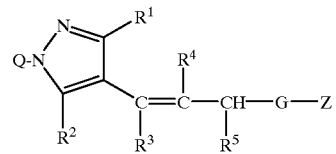

(I)

wherein G represents a nitrogen containing saturated heterocyclic structure represented by the following formula:

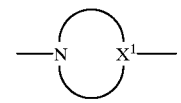

These compounds exhibit anti-tumor activity on 5-FU-resistant tumors and effects on P glycoprotein expressing, multiple-drug resistant tumors. An example of a pyrazole derivative which demonstrates 50% inhibition of tumor cell growth is 3-[4-(3-chloro-5-fluorophenyl)-1 piperazinyl]-1-[1-(3-chloro-2-pyridyl)-5-methyl-4-pyrazolyl)-1-trans-propene hydrochloride. Synthesis of the compounds represented by formula (I) can be prepared by any one of various routes such as a Mannich reaction, a Wittig reaction, reductive amination or substitution by allylation.

7 Claims, No Drawings

PYRAZOLE DERIVATIVES

This is a Continuation-in-Part of PCT Application No. PCT/JP98/00300, filed Jan. 26, 1998 and claims benefit of priority based on Japanese Application Nos. Hei-9-012116 and Hei-10-208807 filed Jan. 27, 1997 and Jul. 24, 1998, respectively.

TECHNICAL FIELD

This invention relates to a novel compound having an antitumor activity, an antitumor agent comprising the compound as an active ingredient, and a method for treating tumors using the antitumor agent.

BACKGROUND ART

Many 5-fluorouracil type drugs (hereinafter abbreviated as 5-FU drugs) have been used as an antitumor agent that can be administered orally, but their mechanism of action is quite the same, and also the effects obtained are not deemed sufficient. Besides, tumors resistant to 5-FU drugs have come out. It has therefore been demanded to develop a new antitumor agent having a different mechanism of action from that of 5-FU drugs which is more efficacious than 5-FU drugs and is effective on 5-FU-resistant tumors as well.

An object of the present invention is to provide a potent antitumor agent which has a novel chemical structure not heretofore reported and exhibits efficacy on 5-FU-resistant tumors as well.

DISCLOSURE OF INVENTION

As a result of extensive study, the inventors of the present invention have found that novel pyrazole derivatives represented by formula (I) hereinafter shown exhibit a powerful antitumor activity even on 5-FU-resistant tumors. It has also been found that the pyrazole derivatives are also effective on P glycoprotein-expressed multiple drug-resistant strains that have been a clinical problem.

The present invention provides a compound represented by formula (I) or a salt thereof;

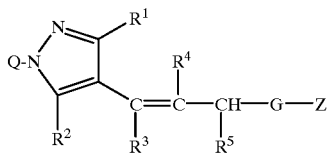

(I)

wherein $R^1$ and $R^2$, which may be the same or different, each represent a hydrogen atom, a halogen atom, a hydroxy group, an alkoxy group, an amino group, an alkylamino group, an aryl group or an alkyl group, in which the alkyl group may be substituted with a halogen atom, an amino group, an alkylamino group, a hydroxy group, an alkoxy group, a thiol group or an alkylthio group; $R^3$ and $R^4$, which may be the same or different, each represent a hydrogen atom, a halogen atom, an alkoxy group, an amino group, an alkylamino group, an aryl group or an alkyl group, in which the alkyl group may be substituted with a halogen atom, an amino group, an alkylamino group, a hydroxy group, an alkoxy group, a thiol group or an alkylthio group; $R^5$ represents a hydrogen atom, an alkyl group, an alkenyl group, an alkynyl group, an aryl group or an arylalkyl group, in which the alkyl group may be substituted with a halogen atom, an amino group, an alkylamino group, a hydroxy group, an alkoxy group, a thiol group or an alkylthio group; Q represents an amidino group, a cycloalkyl group, a phenyl group or a monocyclic heterocyclic group except a pyrimidinyl group bonded to the N atom at its 2-position, and the cycloalkyl, phenyl or monocyclic heterocyclic group may have one or more substituents selected from the group consisting of an alkyl group, an alkyl group substituted with a halogen atom, an amino group, an alkylamino group, a hydroxy group, an alkoxy group, a thiol group or an alkylthio group, a halogen atom, a hydroxy group, an alkoxy group, an alkoxyalkoxy group, an amino group, an alkylamino group, an acylamino group, an alkylaminoalkylamino group, a nitro group, a cyano group, a carbamoyl group, a thiol group, an alkylthio group, an arylthio group, an alkylsulfinyl group, an arylsulfinyl group, an alkylsulfonyl group, an arylsulfonyl group, an aminosulfonyl group, an alkylaminosulfonyl group, an arylaminosulfonyl group, and an aryl group; G represents a nitrogen-containing saturated heterocyclic structure represented by formula:

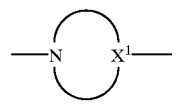

wherein $X^1$ represents a nitrogen atom or CH, in which structure the ring may have a keto group and may have one or more substituents selected from the group consisting of an alkyl group, an alkyl group substituted with a halogen atom, an amino group, an alkylamino group, a hydroxy group, an alkoxy group, a thiol group or an alkylthio group, a halogen atom, a hydroxy group, an alkoxy group, an amino group, an alkylamino group, and an aryl group; Z represents a phenyl group, a heterocyclic group or a phenyl or heterocyclic group having one or more substituents selected from the group consisting of an alkyl group, an alkyl group substituted with a halogen atom, an amino group, an alkylamino group, a hydroxy group, an alkoxy group, a thiol group or an alkylthio group, a halogen atom, a hydroxy group, an alkoxy group, a thiol group, an alkylthio group, an amino group, an alkylamino group, an acylamino group, a nitro group, a cyano group, a carbamoyl group, and an aryl group, in which two substituents on the phenyl or heterocyclic group may be connected to each other to form a ring to provide a condensed bicyclic structure as a whole; the substituent on Z and the substituent on G may be connected to each other to form a condensed tricyclic or tetracyclic structure as a whole.

The compound represented by formula (I) includes both cis- and trans-forms attributed to the double bond of the alkenyl moiety.

Terminologies and expressions used in the present invention are explained. The terminology "cis-form" means a configuration having $R^3$ and $R^4$ on the same side of the double bond, and the terminology "trans-form" denotes a configuration in which $R^3$ and $R^4$ are on the opposite sides of the double bond.

The terminologies "alkyl group", "alkenyl group" and "alkynyl group" are intended to include straight-chain groups and branched groups and preferably indicate those having 1 to 6 (2 to 6 as to alkenyl and alkynyl groups) carbon atoms.

The "alkoxy group" preferably include those having 1 to 6 carbon atoms.

The term "aryl group" means a monovalent group derived from an aromatic hydrocarbon by removing one hydrogen atom from its nucleus and includes, for example, phenyl, tolyl, biphenyl and naphthyl groups.

In the "aminoalkyl group" as referred to herein, the amino moiety may be bonded to any position of the alkyl moiety, and the alkyl moiety preferably contains 1 to 6 carbon atoms.

The terminology "alkylamino group" is indented to include an amino group substituted with one alkyl group and an amino group substituted with two alkyl groups, which may be the same or different, in which the alkyl group preferably contains 1 to 6 carbon atoms.

The term "acyl group" means a carbonyl group (—CO—) with a hydrogen atom, an alkyl group or an aryl group bonded thereto, including formyl, acetyl, propanoyl and benzoyl groups. The alkyl group bonded to the carbonyl group preferably contains 1 to 6 carbon atoms, and the aryl group bonded is preferably a phenyl group.

The term "heterocyclic group" designates a group derived from a monocyclic or bicyclic, saturated or unsaturated heterocyclic compound containing in its ring one or more hetero atoms selected from an oxygen atom, a nitrogen atom and a sulfur atom, the position of the hetero atom(s) being not limited. Monocyclic heterocyclic groups include those derived from monocyclic heterocyclic compounds, such as pyrrole, furan, thiophene, pyrrolidine, tetrahydrofuran, tetrahydrothiophene, imidazole, pyrazole, imidazolidine, pyrazolidine, oxazole, thiazole, oxadiazole, thiadiazole, pyridine, dihydropyridine, tetrahydropyran, piperidine, pyridazine, pyrimidine, triazine, pyrazine, piperazine, dioxane, pyran, and morpholine. Bicyclic heterocyclic groups include those derived from bicyclic heterocyclic compounds, such as benzofuran, indolizine, benzothiophene, indole, naphthyridine, quinoxaline, quinazoline, and chroman.

The terminology "nitrogen-containing saturated heterocyclic group" means a group derived from a saturated heterocyclic compound which contains in its ring one nitrogen atom and may further contain one or more hetero atoms selected from a nitrogen atom, an oxygen atom and a sulfur atom. Examples are those derived from such compounds as pyrrolidine, imidazolidine, pyrazolidine, piperidine, piperazine, and homopiperazine.

The expression "two substituents on the phenyl or heterocyclic group may be connected to each other to form a ring to provide a condensed bicyclic structure as a whole" as used in the definition of Z is intended to mean that two substituents on Z are bonded together to form a structure represented by formula:

wherein $X^2$ and $X^3$ each independently represent an oxygen atom, a sulfur atom, NH or $CH_2$; and l represents an integer of 1 to 3, so that Z has a condensed bicyclic structure as a whole. For example, where Z is a phenyl group, the condensed bicyclic structure has the following structure:

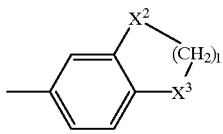

The expression "the substituent on Z and the substituent on G may be connected to each other to form a condensed tricyclic or tetracyclic structure as a whole" as used in the definition of G and Z is intended to mean that the substituent on Z and the substituent on G may be connected to each other to form a cyclic structure represented by formula:

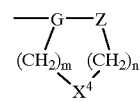

wherein $X^4$ represents an oxygen atom, a sulfur atom, NH or $CH_2$; and m and n each represent 0 or an integer of 1 to 3, so that G and Z form a condensed tricyclic or tetracyclic structure as a whole. For example, where G is a piperazinyl group, and Z is a phenyl group, there is formed the following structure as a whole:

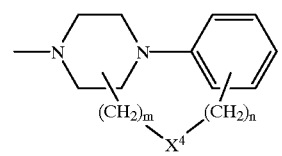

In formula (I), $R^1$ preferably represents a hydrogen atom, a halogen atom, a hydroxy group, an alkoxy group, an amino group, a phenyl group or an alkyl group, in which the alkyl group may be substituted with an amino group, an alkylamino group, a hydroxy group, an alkoxy group, a thiol group or an alkylthio group.

$R^2$ preferably represents a hydroxy group, an alkoxy group, an amino group or an alkyl group, in which the alkyl group may be substituted with a halogen atom, an amino group, an alkylamino group, a hydroxy group, an alkoxy group, a thiol group or an alkylthio group.

$R^3$ preferably represents a hydrogen atom or an alkyl group, in which the alkyl group may be substituted with an amino group, an alkylamino group, a hydroxy group, an alkoxy group, a thiol group or an alkylthio group.

$R^4$ preferably represents a hydrogen atom or an alkyl group, in which the alkyl group may be substituted with an amino group, an alkylamino group, a hydroxy group, an alkoxy group, a thiol group or an alkylthio group.

$R^5$ preferably represents a hydrogen atom or an alkyl group, in which the alkyl group may be substituted with an amino group, an alkylamino group, a hydroxy group, an alkoxy group, a thiol group or an alkylthio group.

Q preferably represents a phenyl group or a monocyclic heterocyclic group. The phenyl group or monocyclic heterocyclic group may have a substituent. The monocyclic heterocyclic group is preferably unsaturated and still preferably a 5- or 6-membered ring.

Q still preferably represents a 5- or 6-membered, unsaturated, monocyclic heterocyclic group, exclusive of a pyrimidinyl group bonded at the 2-position thereof, containing at least one nitrogen atom in its ring, such as one derived from pyridine, pyrimidine or pyridazine.

Substituents on Q preferably include a halogen atom, a cyano group, a hydroxy group, an alkoxy group, an alkylthio group, an alkylsulfinyl group, an alkylsulfonyl group, and an alkyl group.

G preferably represents a 5- or 6-membered nitrogen-containing saturated heterocyclic structure represented by formula:

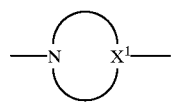

wherein $X^1$ represents a nitrogen atom or CH, particularly one derived from piperazine or piperidine.

The heterocyclic group as Z is preferably a 5- or 6-membered monocyclic heterocyclic group, particularly an unsaturated one. Examples of the preferred heterocyclic group are pyridyl, pyridazyl, pyrazyl, pyrimidinyl and triazyl groups.

Z preferably represents a substituted or unsubstituted phenyl group or a substituted or unsubstituted pyrimidinyl group.

When substituted, Z preferably has one or two-substituents selected from the group consisting of a halogen atom, a hydroxy group, a cyano group, an alkyl group, and an alkyl group substituted with a halogen atom, an amino group, an alkylamino group, a hydroxy group, an alkoxy group, a thiol group or an alkylthio group.

Z also preferably represents a condensed bicyclic structure formed by connecting two substituents on the phenyl or heterocyclic group to form a ring represented by formula:

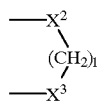

wherein $X^2$ and $X^3$ each independently represent an oxygen atom, a sulfur atom, NH or $CH_2$; and l represents an integer of 1 to 3, Z still preferably represents a phenyl group having two substituents, either the same or different, selected from the group consisting of a halogen atom, a hydroxy group, a cyano group, an alkyl group, and an alkyl group substituted with a halogen atom, an amino group, an alkylamino group, a hydroxy group, an alkoxy group, a thiol group or an alkylthio group.

Of the geometrical isomers of the compounds represented by formula (I), the trans-form (in which $R^3$ and $R^4$ are on the opposite sides of the double bond) is preferred.

The compound represneted by formula (I) can be prepared through various routes. A typical process is shown below.

Process A

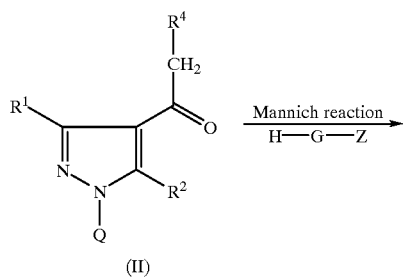

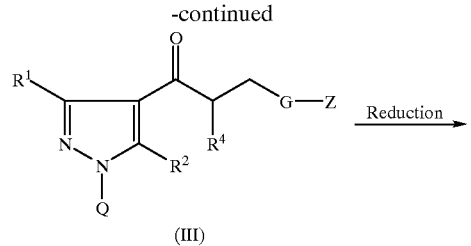

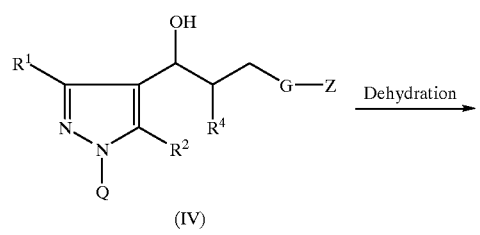

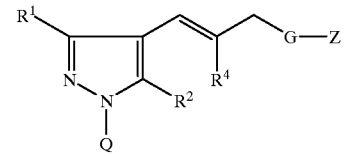

wherein $R^1$, $R^2$, $R^4$, Q, G, and Z are as defined above.

That is, compound (II) and a basic compound H—G—Z are subjected to Mannich reaction to obtain compound (III), which is then reduced to compound (IV), followed by dehydration to give compound (I).

Each reaction involved will be explained in detail.

Mannich Reaction

Compound (II) and a basic compound H—G—Z are reacted in a solvent in the presence of a condensing agent to obtain compound (III). It is preferred for the compound H—G—Z to be used in the salt form such as a hydrochloride, a hydrobromide.

Suitable condensing agents include paraformaldehyde and formaldehyde.

Suitable solvents include alcohols, such as methanol, ethanol and propanol; amide solvents, such as N,N-dimethylformamide, acetamide, and dimethylacetamide; halogenated hydrocarbons, such as chloroform, dichloromethane, and carbon tetrachloride; ethers, such as diethyl ether, tetrahydrofuran, and dioxane; aromatic hydrocarbons, such as benzene, toluene, and xylene; and mixtures thereof.

The reaction is carried out usually at −20° to 150° C., preferably 0° to 100° C., for 5 minutes to 120 hours, preferably 30 minutes to 72 hours.

Reduction

Reduction of compound (III) yields compound (IV). The reduction can be conducted by a method custamrily used in the art. For example, compound (III) is treated with a reducing agent or hydrogenated in the presence of a catalyst.

Suitable reducing agents include boron hydride compounds and aluminum hydride compounds, such as sodium borohydride, sodium cyanoborohydride, and lithium aluminum hydride. Useful catalysts include palladium, Raney nickel, and platinum oxide.

An appropriate solvent is chosen according to the reducing agent. Useful solvents include alcohols, such as methanol, ethanol, and propanol; amide solvents, such as N,N-dimethylformamide, acetamide, and dimethylacetamide; halogenated hydrocarbons, such as chloroform, dichloromethane, and carbon tetrachloride; ethers, such as diethyl ether, tetrahydrofuran, and dioxane; aromatic hydrocarbons, such as benzene, toluene, and xylene; and mixtures thereof.

The reaction is carried out usually at −20° to 150° C., preferably 0° to 100° C., for 5 minutes to 72 hours, preferably 10 minutes to 24 hours.

Dehydration

Dehydration of compound (IV) affords compound (I). The dehydration can be performed in a method commonly used in the art. For example, compound (IV) is heated in the presence of an acid.

Either organic acids or inorganic acids can be used for dehydration. Examples of useful inorganic acids are hydrochloric acid, sulfuric acid, hydrobromic acid, and potassium hydrogensulfate. Examples of useful organic acids are p-toluenesulfonic acid, methanesulfonic acid, and oxalic acid. Inorganic acids are preferred to organic ones. In addition, alumina is also useful.

A solvent may be used for dehydration. Suitable solvents include amide solvents, such as N,N-dimethylformamide, acetamide, and dimethylacetamide; halogenated hydrocarbons, such as chloroform, dichloromethane, and carbon tetrachloride; ethers, such as diethyl ether, tetrahydrofuran, and dioxane; aromatic hydrocarbons, such as benzene, toluene, and xylene; and mixtures thereof.

The reaction is conducted usually at −20° to 150° C., preferably 0° to 100° C., for 5 minutes to 72 hours, preferably 10 minutes to 24 hours.

Process A described above provides compound (I) in which $R^3$ is a hydrogen atom, and the alkenyl group moiety is trans. Compound (I) in which $R^3$ is an alkyl group and/or the alkenyl group moiety is cis can be synthesized according to process B shown below.

Process B

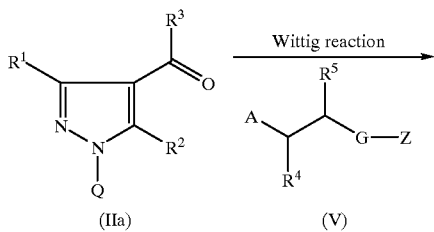

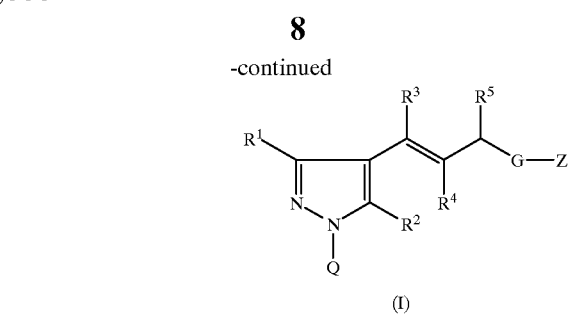

wherein A represents a chlorine atom, a bromine atom or an iodine atom; and $R^1$, $R^2$, $R^3$, $R^4$, $R^5$, Q, G, and Z are as defined above.

That is, compound (I) can be obtained by subjecting compound (IIa) and compound (V) to Wittig reaction. More specifically, compound (V) and a tertiary phosphine compound are reacted in a solvent. The resulting phosphonium salt is treated with a base in a solvent, and compound (IIa) is added thereto to obtain compound (I).

Suitable tertiary phosphine compounds include triphenylphosphine and tri-n-butylphosphine.

Suitable bases include n-butyllithium, phenyllithium, sodium hydride, potassium t-butoxide, sodium ethoxide, and 1,8-diazabicyclo[5.4.0]undec-7-ene (DBU).

Useful solvents includes ethers, such as diethyl ether, tetrahydrofuran, and dioxane; aromatic hydrocarbons, such as benzene, toluene, and xylene; alcohols, such as methanol, ethanol, and propanol; amide solvents, such as N,N-dimethylformamide, acetamide, and dimethylacetamide; halogenated hydrocarbons, such as chloroform, dichloromethane, and carbon tetrachloride; and mixtures thereof.

The reaction is carried out usually at 30° to 150° C., preferably 50° to 100° C., for a period of 5 minutes to 72 hours, preferably 10 minutes to 24 hours.

The starting compounds (II) and (IIa), the basic compound H—G—Z, and compound (V) are known compounds or can easily be synthesized in a known manner.

Compound (I) of the present invention can also be prepared through the following process C (reductive amination or substition via allylation).

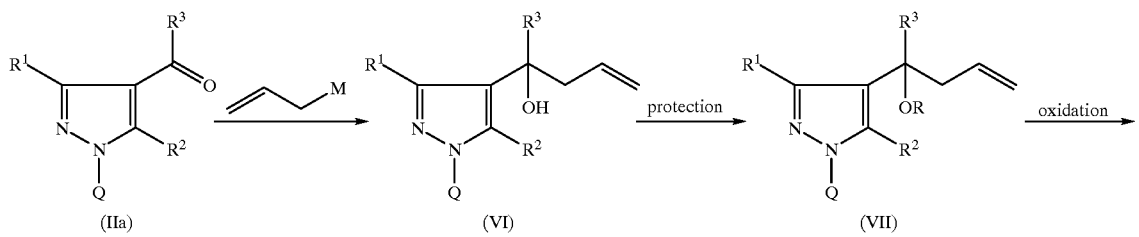

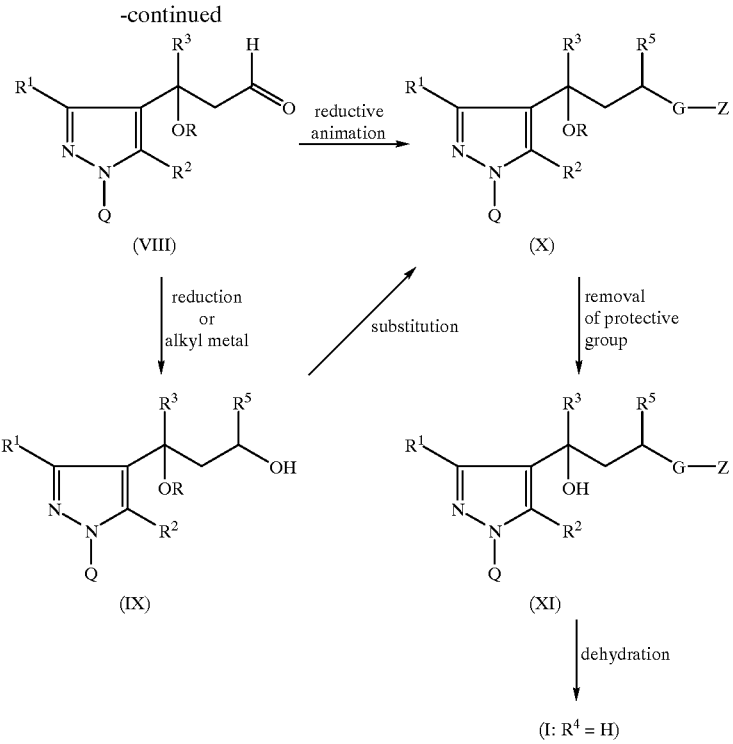

(VIII) → reductive amination → (X)

(VIII) → reduction or alkyl metal → (IX)

(IX) → substitution → (X)

(X) → removal of protective group → (XI)

(XI) → dehydration → (I: $R^4$ = H)

wherein M represents a metal (e.g., an alkali metal, an alkaline earth metal, tin, zinc, nickel, etc.); and $R^1$, $R^2$, $R^3$, $R^5$, Q, G, and Z are as defined above.

Compound (IIa) is reacted with an appropriate allyl metal compound, or allylsilane is added to compound (IIa) in the presence of a Lewis acid, to form compound (VI). The hydroxy group of compound (VI) is protected to obtain compound (VII), which is oxidized to convert to compound (VIII). Compound (VIII) and a basic compound, such as substituted piperazine, are subjected to reductive amination to obtain compound (X). If necessary, the protective group is removed from compound (X). Compound (X) is dehydrated to give compound (I) in which $R^4$ is a hydrogen atom. Compound (X) can also be obtained by reducing compound (VIII) or reacting compound (VIII) with an alkyl metal compound to obtain compound (IX), converting the hydroxy group to a releasable group, followed by substitution reaction with a basic compound, such as substituted piperazine.

Each reaction involved in process C will be described in detail.

Addition Reaction

Compound (IIa) is reacted with an appropriate allyl metal compound, or allylsilane is added to compound (IIa) in the presence of a Lewis acid (e.g., titanium tetrachloride), to form compound (VI).

The allyl metal compound to be used includes allyl lithium, an allylmagnesium halide, and an allyltin compound. The allylsilane compound to be used includes an allyltrialkylsilane and an allyltriarylsilane. Suitable Lewis acids include titanium tetrachloride.

Solvents that can be used in the addition reaction include ethers, such as diethyl ether, tetrahydrofuran, and dioxane; hydrocarbons, such as hexane, pentane, benzene, toluene, and xylene; and mixtures thereof. Where an allyltin compound is used, water or a water-containing ether solvent is also useful.

The addition reaction is carried out usually at −78° to 100° C., preferably −78° to 70° C., for a period of 5 minutes to 120 hours, preferably 30 minutes to 48 hours.

Protection of Hydroxy Group

The hydroxy group of compound (VI) can be protected with a protective group generally used in the art. Examples of such a protective group include substituted methyl ether groups, such as a methoxymethyl ether group, a methylthiomethyl ether group, and a benzyloxymethyl ether group; substituted ethyl ether groups, such as a 1-methoxyethyl ether group and a 2,2,2-trichloroethyl ether group; a benzyl ether group; substituted benzyl ether groups, such as a p-methoxybenzyl ether group; silyl ether groups, such as a triethylsilyl group and a t-butyldimethylsilyl group; ester groups, such as an acetyl group; and carbonate groups, such as a methoxycarbonyl group and a 2,2,2-trichloroethoxycarbonyl group.

Oxidation

Compound (VIII) can be obtained from compound (VII) in a manner usually adopted in the field of the art. For example, compound (VII) is subjected to stoichiometric oxidation reaction with an oxidizing agent (e.g., osmium tetroxide) or catalytic oxidation reaction with a co-oxidizing agent to once obtain a diol compound, which is then subjected to ordinary oxidation reaction, such as decomposition with periodic acid, to give compound (VIII). Alternatively, compound (VIII) can be obtained by subjecting compound (VII) to ordinary ozone decomposition accompanying a reductive treatment in a solvent.

Oxidizing agents useful for the formation of a diol compound include potassium permanganate and osmium tetroxide. Co-oxidizing agents useful for the same purpose include hydrogen peroxide, a hydrogen peroxide aqueous solution, perchloric acid, perchloric acid salts (e.g., sodium perchlorate), N-methylmorpholine-N-oxide, and potassium hexacyanoferrate (III).

Suitable solvents for use in the formation of a diol compound include alcohols, such as methanol, ethanol, and t-butanol; ketones, such as acetone and methyl ethyl ketone; chlorine-containing solvents, such as dichloromethane and dichloroethane; ethers, such as diethyl ether, tetrahydrofuran, and dioxane; hydrocarbons, such as hexane, pentane, and benzene; water; and mixtures thereof.

The reaction for the formation of a diol compound is conducted usually at −78° to 100° C., preferably −78° C. to room temperature, for a period of from 5 minutes to 120 hours, preferably 30 minutes to 48 hours.

Decomposition of the diol with periodic acid is performed in a solvent by using periodic acid, a periodic acid salt, etc. as an oxidizing agent. Suitable solvents include alcohols, such as methanol, ethanol, and t-butanol; ketones, such as acetone and methyl ethyl ketone; chlorine-containing solvents, such as dichloromethane and dichloroethane; ethers, such as diethyl ether, tetrahydrofuran, and dioxane; hydrocarbons, such as hexane, pentane, and benzene; water; and mixtures thereof.

The reaction is conducted usually at −20° to 100° C., preferably 0° C. to room temperature, for 5 minutes to 120 hours, preferably 30 minutes to 48 hours.

Solvents that can be used in ozone decomposition include alcohols, such as methanol, ethanol, and propanol; ketones, such as acetone and methyl ethyl ketone; chlorine-containing solvents, such as dichloromethane and dichloroethane; ethers, such as diethyl ether, tetrahydrofuran, and dioxane; hydrocarbons, such as hexane and pentane; and mixtures thereof.

The ozone decomposition reaction is effected usually at −78° to 100° C., preferably −78° C. to room temperature, for 5 minutes to 120 hours, preferably 30 minutes to 48 hours.

Reductive Amination

The reaction for obtaining compound (X) from compound (VIII) is conducted in a conventional manner. For example, compound (VIII) is reacted with a basic compound, such as substituted piperazine, and the product is treated with a reducing agent to yield compound (X).

Useful reducing agents include complex hydrides, such as lithium aluminum hydride, sodium borohydride, and sodium cyanoborohydride, and diboran. Hydrogenation in the presence of a catalyst, such as Raney nickel or palladium-on-carbon, will do.

Solvents to be used include alcohols, such as methanol, ethanol, and propanol; ethers, such as diethyl ether, tetrahydrofuran, and dioxane; hydrocarbons, such as hexane, pentane, benzene, toluene, and xylene; and mixtures thereof.

The reductive amination reaction is carried out usually at a temperature of −78° to 100° C., preferably −10° C. to room temperature, for a period of from 5 minutes to 120 hours, preferably 30 minutes to 48 hours.

Reduction

Compound (IX) in which $R^5$ is a hydrogen atom can be obtained by reducing the carbonyl group of compound (VIII). The reduction can be carried out in a conventional manner, for example, by treatment with a reducing agent or hydrogenation in the presence of a catalyst. Useful reducing agents include boron hydride compounds and aluminum hydride compounds, such as sodium borohydride and lithium aluminum hydride. Useful catalysts include palladium, Raney nickel, and platinum oxide.

The reaction can be conducted in a solvent, which is to be chosen according to the kind of the reducing agent. Useful solvents include alcohols, such as methanol, ethanol, and propanol; amide solvents, such as N,N-dimethylformamide, acetamide, and dimethylacetamide; chlorine-containing solvents, such as chloroform, dichloromethane, and carbon tetrachloride; ethers, such as diethyl ether, tetrahydrofuran, and dioxane; hydrocarbons, such as hexane, pentane, benzene, toluene, and xylene; and mixture thereof.

The reaction temperature usually ranges from −78° to 100° C., preferably −78° to room temperature. The reaction period usually ranges from 5 minutes to 120 hours, preferably 30 minutes to 48 hours.

Addition of Alkyl Group

Where $R^5$ is not a hydrogen atom, a corresponding compound (IX) can be obtained by reacting compound (VIII) with an alkyl metal compound.

The alkyl addition reaction can be conducted in a customarily employed manner. For example, compound (VIII) is treated with an alkyllithium or an alkylmagnesium halide.

Suitable alkyl metal compounds include alkyllithiums, such as methyllithium and ethyllithium, and alkylmagnesium halides, such as methylmagnesium iodide and ethylmagnesium bromide.

The reaction can be performed in the presence of a solvent, such as an ether solvent, e.g., diethyl ether, tetrahydrofuran or dioxane, a hydrocarbon solvent, e.g., hexane, pentane, benzene, toluene or xylene, or a mixture thereof.

The reaction is executed usually at a temperature of −78° to 100° C., preferably −78° C. to room temperature, for a period of 5 minutes to 120 hours, preferably 30 minutes to 48 hours.

Substitution with Amino Group

The hydroxy group of compound (IX) is once changed to a releasable group, such as a halogen atom or a sulfonic ester group, and then the resulting derivative of compound (IX) is reacted with a basic compound, such as substituted piperazine, to obtain compound (X).

Conversion of a hydroxy group to a releasable group, such as a halogen atom or a sulfonic ester group, can be effected in a usual manner. For example, halogenation is achieved by treating with a phosphorus trihalide, a phosphorus pentahalide, etc. in a solvent, e.g., dichloromethane or chloroform; or treating with a Vilsmeier reagent, such as N,N-dimethylchloroforminium chloride or bromide, in a solvent, such as N,N-dimethylformamide or dioxane. Sulfonylation can be conducted by, for example, treating with methanesulfonyl chloride, p-toluenesulfonyl chloride, etc. in a solvent in the presence of an appropriate base.

The substitution reaction between the resulting derivative of compound (IX) and a basic compound (e.g., substituted piperazine) can be performed in a conventional manner. For example, a mixture of the derivative of compound (IX) and a basic compound (e.g., substituted piperazine) is heated in a solvent (e.g., acetonitrile) in the presence of a base (e.g., potassium carbonate) to give compound (X).

Removal of Protective Group

The hydroxy-protective group of compound (X) can be removed under conditions known for the protective group used.

Dehydration

Dehydration of compound (XI) gives compound (I). The dehydration can be conducted in a known manner, for example, by heating in the presence of an acid.

Either organic acids or inorganic acids can be used. Examples of useful inorganic acids are hydrochloric acid, sulfuric acid, hydrobromic acid, and potassium hydrogensulfate. Examples of useful organic acids are p-toluenesulfonic acid, methanesulfonic acid, and oxalic acid. Inorganic acids are preferred to organic ones. In addition, alumina is also useful.

A solvent may be used in the dehydration. Suitable solvents include amide solvents, such as N,N-dimethylformamide, acetamide, and dimethylacetamide; halogenated hydrocarbons, such as chloroform, dichloromethane, and carbon tetrachloride; ethers, such as diethyl ether, tetrahydrofuran, and dioxane; aromatic hydrocarbons, such as benzene, toluene, and xylene; and mixtures thereof.

The reaction is conducted usually at −20° to 150° C., preferably 0° to 100° C., for 5 minutes to 72 hours, preferably 10 minutes to 24 hours.

Compound (I) in which the alkenyl group moiety is trans can be synthesized according to process D shown below.

presence of a reducing agent. Where the reduction proceeds to give a corresponding alcohol, the resulting alcohol is oxidized to obtain compound (XII).

Suitable reducing agents include those generally used for 1,2-reduction of an α,β-unsaturated carbonyl compound, such as diisobutylaluminum hydride or lithium aluminum hydride.

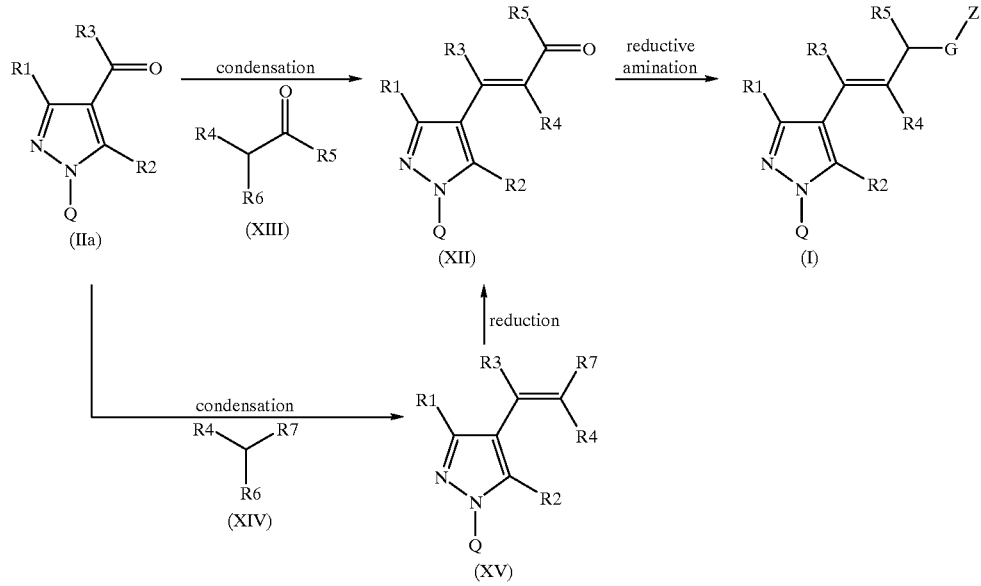

Process D wherein $R^1, R^2, R^3, R^4, R^5$, Q, Z, and Z are as defined above; $R^6$ represents a hydrogen atom, a carboxyl group, an alkoxycarbonyl group, a chlorine atom, a bromine atom or an iodine atom; and $R^7$ represents an alkoxycarbonyl group, a carbamoyl group or a cyano group.

That is, compound (IIa) and compound (XIII) are condensed to obtain compound (XII). Compound (XII) and a basic compound H—G—Z are reacted (reductive aminated) to give compound (I). Compound (XII) where $R^5$ is a hydrogen atom is also obtainable by condensing compound (IIa) and compound (XIV) to obtain compound (XV) and reducing compound (XV).

Each reaction included in process D will be described below in detail.

Condensation

The condensation reaction of compound (IIa) into compound (XII) or (XV) can be carried out by the condensation generally employed in the art. For example, compound (IIa) and compound (XIII) or (XIV) are subjected to Aldol condensation; or compound (IIa) and a phosphonium salt synthesized from compound (XIII) or (XIV) are subjected to Wittig reaction; or compound (IIa) and an alkylphosphorous diester synthesized from compound (XIII) or (XIV) to Wittig-Horner reaction. Phosphonium salts synthesized from compound (XIII) or (XIV) include a triphenylphosphonium salt and a tri-n-butylphosphonium salt. Alkylphosphorous diesters synthesized from compound (XIII) or (XIV) include dimethyl alkylphosphites, diethyl alkylphosphites, and diphenyl alkylphosphites.

Reduction

Compound (XII) in which $R^5$ is a hydrogen atom can be obtained by treating compound (XV) in a solvent in the Reductive Amination Reductive amination can be conducted in the same manner as described above.

If desired, the compounds according to the present invention can be converted to their physiologically acceptable salts with inorganic acids, such as hydrochloric acid, sulfuric acid, and phosphoric acid, or organic acids, such as formic acid, acetic acid, and methanesulfonic acid. Further, the compounds or the salts of the present invention can exist in the form of a hydrate.

The antitumor effect of the compounds according to the present invention will be demonstrated in the following Test Example.

Test Example 1

Tumor cells PC-12 and PC-6, which had been serially cultured in RPMI 1640 containing 10% fetal bovine serum, 2 mM L-glutamine, and 100 μg/ml of kanamycin sulfate, were inoculated to a 96-well microplate ($1.0 \times 10^3$ cells-PC-12/150 μl/well; $5.0 \times 10^3$ cells-PC-6/150 μl/well). After 24-hour incuvation, 50 μl of a preparation containing each of the compounds of Examples 5 to 8 and Example 13 (hereinafter described) in a varied concentration was added to each well, followed by culturing for 3 days. A 5 mg/ml solution of 3-(4,5-dimethylthiazol-2-yl)-2,5-diphenyl-2H-tetrazolium bromide (MTT) was added in an amount of 20 μl per well. Four hours later, the culture broth was removed, 150 μl/well of dimethyl sulfoxide was added to the residue, and the absorbance was measured at 540 nm. The concentration of the compound which showed 50% inhibition on cell growth as compared with a control group ($GI_{50}$; ng/ml) is shown as an antitumor effect in Table 1 below.

TABLE 1

| Compound | PC-6 (ng/ml) | PC-12 (ng/ml) |
|---|---|---|
| Example 5 | 10.6 | 91.3 |
| Example 6 | 8.79 | 34.7 |
| Example 7 | 38.2 | 237 |
| Example 8 | 37.3 | 210 |
| Example 13 | 4.93 | 38.3 |
| Example 58 |  | 13.4 |
| Example 59 |  | 11 |
| Example 60 |  | 20.7 |
| Example 67 |  | 66.2 |
| Example 68 |  | 9.16 |
| Example 69 |  | 24.6 |
| Example 70 |  | 10.1 |
| Example 71 |  | 3.17 |
| Example 72 |  | 35.0 |

As is apparent from Table 1, the compounds according to the present invention exhibit an antitumor activity and is applicable as an antitumor agent in the treatment of various tumors.

The antitumor agent according to the present invention can be administered through various routes, such as intravenous injection, intramuscular injection, subcutaneous injection, or oral administration. Intravenous administration of injectable aqueous preparations and oral administration are preferred. Aqueous preparations can be prepared by converting the compound of the invention into an acid addition salt with a pharmacologically acceptable acid. For oral administration, the compound can be used either in a free form or in a salt form.

The compounds of this invention and the salts thereof can be formulated into various pharmaceutical compositions in a manner commonly employed in the art. Suitable dosage forms can be selected according to the administration route. Typical dosage forms for oral administration include tablets, powders, granules, capsules, solutions, syrups, elixirs, and oily or aqueous suspensions.

Injectable solutions can contain stabilizers, preservatives, and dissolving aids. The solution which may contain these adjuvants can be put in a container and made into a solid preparation by, for example, freeze-drying, which can be dissolved on use. A single injection dose may be put in an ampule, or multiple doses may be put in a container.

Liquid preparations include solutions, suspensions, emulsions, etc. In formulating the pharmaceutical composition into these liquid preparations, suspending agents, emulsifying agents, and the like can be used as additives.

The dosage of the antitumor agent containing the compound of the present invention as an active ingredient is 10 mg to 3 g, preferably 50 mg to 2 g, in a single dose/day for an adult. Administration is preferably repeated at appropriate intervals.

BEST MODE FOR CARRYING OUT INVENTION

The present invention will now be illustrated in greater detail with reference to Examples, but it should be understood that the present invention is not construed as being limited thereto.

EXAMPLE 1

Synthesis of 3-[4-(3,5-Dichlorophenyl)-1-piperazinyl]-1-[5-methyl-1-(2-pyridyl)-4-pyrazolyl]-1-trans-propene Hydrochloride

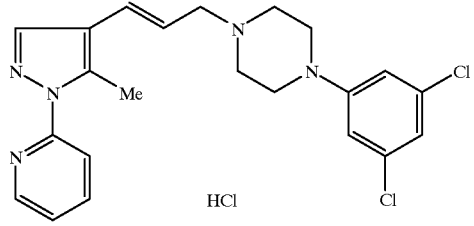

1) Preparation of 3-[4-(3,5-Dichlorophenyl)-1-piperazinyl]-1-[5-methyl-1-(2-pyridyl)-4-pyrazolyl]-1-propanone Hydrochloride In 150 ml of absolute ethanol was dissolved 2.26 g of 4-acetyl-1-(2-pyridyl)-5-methylpyrazole, and 2.94 g of 1-(3,5-dichlorophenyl)piperazine hydrochloride and 0.9 g of p-formaldehyde were added to the solution, followed by refluxing for 6 hours. To the reaction mixture was further added 0.40 g of p-formaldehyde, and the refluxing was continued for an additional 24 hour period. About a half of the ethanol was removed by evaporation, and the precipitate was collected by filtration. The precipitate was dissolved in chloroform, washed successively with a saturated aqueous solution of sodium hydrogencarbonate and a saturated aqueous solution of sodium chloride, and dried over anhydrous sodium sulfate. The solvent was removed by evaporation, and the residue was subjected to column chromatography on silica gel using a mixture of chloroform-methanol (50:1 by volume) as a developing solvent. The fraction containing the desired compound was concentrated. A 1N hydrochloric acid/ethanol solution was added to the residue, followed by concentration. The residue was recrystallized from ethanol to yield 2.90 g of the title compound.

Melting point: 210–213° C. (decomposition)

$^1$H-NMR (DMSO-$d_6$) δ: 2.84 (s, 3H), 3.1–3.3 (m, 4H), 3.45–3.6 (m, 4H), 3.6–3.7 (m, 2H), 3.95–4.05 (m, 2H), 6.94 (s, 1H), 7.07 (s, 2H), 7.51 (dd, 1H, J=7.3, 4.9 Hz), 7.84 (d, 1H, J=7.8 Hz), 8.08 (dd, 1H, J=7.8, 7.3 Hz), 8.40 (s, 1H), 8.58 (d, 1H, J=4.9 Hz)

2) Preparation of 3-[4-(3,5-Dichlorophenyl)-1-piperazinyl]-1-[5-methyl-1-(2-pyridyl)-4-pyrazolyl]-1-trans-propene Hydrochloride In a mixed solvent of 70 ml of absolute ethanol and 70 ml of anhydrous tetrahydrofuran were dissolved 1.44 g of the compound obtained in (1) above, and the solution was cooled to 0° C. To the solution was added 500 mg of sodium borohydride, and the mixture was stirred at that temperature for 1 hour. To the mixture was further added 50 mg of sodium borohydride, followed by stirring for 1 hour. A 1N hydrochloric acid/ethanol solution was added to neutralize, and the solvent was removed by evaporation. To the residue was added chloroform, and the mixture was washed successively with a saturated aqueous solution of sodium hydrogencarbonate and a saturated aqueous solution of sodium chloride, and dried over anhydrous sodium sulfate. The solvent was removed by evaporation. To the residue were added 50 ml of anhydrous dioxane, 50 ml of anhydrous tetrahydrofuran, and 830 mg of p-toluenesulfonic acid monohydrate, followed by heating under reflux for 3 hours. After the solvent was evaporated off, chloroform was added to the residue, and the mixture was washed successively with a saturated aqueous solution of sodium hydrogencarbonate and a saturated aqueous solution of sodium chloride, and dried over anhydrous sodium sulfate. The solvent was removed by evaporation. The residue was subjected to column chromatography on silica gel using a mixture of chloroform-methanol (50:1 by volume) as a developing solvent. The fraction containing the desired compound was concentrated. A 1N hydrochloric acid/ethanol solution was added to the residue, followed by concentration. The residue was recrystallized from ethanol to yield 1.31 g of the title compound.

Melting point: 214–218° C. (decomposition)

$^1$H-NMR (DMSO-d$_6$) δ: 2.65 (s, 3H), 3.05–3.25 (m, 4H), 3.45–3.6 (m, 2H), 3.9–4.05 (m, 4H), 6.18 (dt, 1H, J=15.6, 7.3 Hz), 6.81 (d, 1H, J=15.6 Hz), 6.97 (s, 1H), 7.06 (s, 2H), 7.40 (dd, 1H, J=7.3, 4.9 Hz), 7.83 (d, 1H, J=8.3 Hz), 8.00 (dd, 1H, J=8.3, 7.3 Hz), 8.06 (s, 1H), 8.50 (d, 1H, J=4.9 Hz)

EXAMPLE 2

Synthesis of 3-[4-(3-Chlorophenyl)-1-piperazinyl]-1-[5-methyl-1-(2-pyridyl)-4-pyrazolyl]-1-trans-propene Hydrochloride

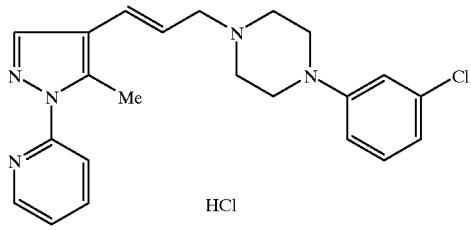

3-[4-(3-Chlorophenyl)-1-piperazinyl]-1-[5-methyl-1-(2-pyridyl)-4-pyrazolyl]-1-propanone hydrochloride (1.29 g) was reacted, and the product was worked up in the same manner as in Example 1-(2) to yield 889 mg of the title compound.

Melting point: 199–204° C. (decomposition)

$^1$H-NMR (DMSO-d$_6$) δ: 2.66 (s, 3H), 3.1–3.2 (m, 4H), 3.5–3.6 (m, 2H), 3.9–4.0 (m, 4H), 6.19 (dt, 1H, J=15.6, 7.3 Hz), 6.82 (d, 1H, J=15.6 Hz), 6.87 (dd, 1H, J=8, 1.5 Hz), 6.97 (dd, 1H, J=8, 2.0 Hz), 7.05 (s, 1H), 7.26 (t, 1H, J=8 Hz), 7.39 (dd, 1H, J=4.9, 2.0 Hz), 7.83 (d, 1H, J=8.3 Hz), 8.00 (t, 1H, J=8.3 Hz), 8.04 (s, 1H), 8.50 (d, 1H, J=4.9 Hz)

EXAMPLE 3

Synthesis of 3-[4-(3,5-Dichlorophenyl)-1-piperazinyl]-1-[5-methyl-1-(4-pyridyl)-4-pyrazolyl]-1-trans-propene Hydrochloride

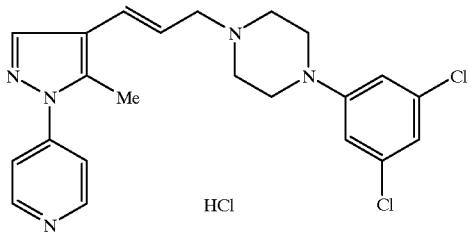

1) Preparation of 3-[4-(3,5-Dichlorophenyl)-1-piperazinyl]-1-[5-methyl-1-(4-pyridyl)-4-pyrazolyl]-1-propanone Hydrochloride 4-Acetyl-5-methyl-1-(4-pyridyl)pyrazole (0.61 g), 1-(3,5-dichlorophenyl)piperazine hydrochloride (0.80 g), and p-formaldehyde (0.42 g) were reacted in the same manner as in Example 1-(1). The reaction mixture was cooled, and the precipitated crystals were collected by filtration, dissolved in chloroform, and washed successively with a saturated aqueous solution of sodium hydrogencarbonate and a saturated aqueous solution of sodium chloride, and dried over anhydrous sodium sulfate. The solvent was removed by evaporation. The residue was subjected to column chromatography on silica gel using a mixture of chloroform-methanol (50:1 by volume) as a developing solvent. The fraction containing the desired compound was concentrated. A 1N hydrochloric acid/ethanol solution was added to the residue, followed by concentration. The residue was recrystallized from ethanol to yield 149 mg of the title compound.

Melting point: 202–206° C. (decomposition)

$^1$H-NMR (DMSO-d$_6$) δ: 2.70 (s, 3H), 3.1–3.25 (m, 4H), 3.45–3.65 (m, 6H), 4.0–4.1 (m, 2H), 6.97 (s, 1H), 7.08 (s, 2H), 7.74 (d, 2H, J=6 Hz), 8.47 (s, 1H), 8.80 (d, 2H, J=6 Hz)

2) Preparation of 3-[4-(3,5-Dichlorophenyl)-1-piperazinyl]-1-[5-methyl-1-(4-pyridyl)-4-pyrazolyl]-1-trans-propene Hydrochloride In a mixed solvent of 7 ml of absolute ethanol and 7 ml of anhydrous tetrahydrofuran was dissolved 144 mg of the compound obtained in (1) above, and the solution was cooled to 0° C. To the solution was added 50 mg of sodium borohydride, and the mixture was stirred at that temperature for 1 hour. To the mixture was further added 5 mg of sodium borohydride, followed by stirring for 1 hour. A 1N hydrochloric acid/ethanol solution was added to neutralize, and the solvent was removed by evaporation. To the residue was added chloroform, and the mixture was washed successively with a saturated aqueous solution of sodium hydrogencarbonate and a saturated aqueous solution of sodium chloride, and dried over anhydrous sodium sulfate. The solvent was removed by evaporation. To the residue were added 7 ml of anhydrous dioxane, 7 ml of anhydrous tetrahydrofuran, and 110 mg of p-toluenesulfonic acid monohydrate, followed by heating under reflux. After 2 hours, 30 ml of anhydrous dioxane and 110 mg of p-toluenesulfonic acidmonohydrate were added, and the heat refluxing was continued for 3 hours. After the solvent was evaporated off, chloroform was added to the residue, and the mixture was washed successively with a saturated aqueous solution of sodium hydrogencarbonate and a saturated aqueous solution of sodium chloride, and dried over anhydrous sodium sulfate. The solvent was removed by evaporation. The residue was subjected to column chromatography on silica gel using a mixture of chloroform-methanol (50:1 by volume) as a developing solvent. The fraction containing the desired compound was concentrated. A 1N hydrochloric acid/ethanol solution was added to the residue, followed by concentration. The residue was recrystallized from ethanol to yield 69 mg of the title compound.

Melting point: 201–205° C. (decomposition)

$^1$H-NMR (DMSO-$d_6$) δ: 2.53 (s, 3H), 3.05–3.25 (m, 4H), 3.4–3.5 (m, 2H), 3.9–4.05 (m, 4H), 6.20 (dt, 1H, J=16, 8 Hz), 6.81 (d, 1H, J=16 Hz), 6.96 (s, 1H), 7.05 (s, 2H), 7.77 (d, 2H, J=6 Hz), 8.14 (s, 1H), 8.76 (d, 2H, J=6 Hz)

EXAMPLE 4

Synthesis of 3-[4-(3-Chlorophenyl)-1-piperazinyl]-1-[5-methyl-1-(4-pyridyl)-4-pyrazolyl]-1-trans-propene Dihydrochloride

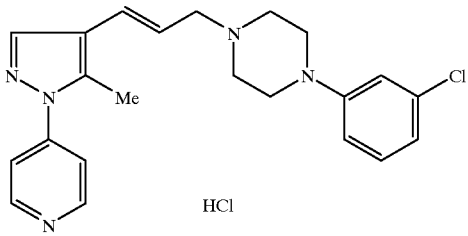

1) Preparation of 3-[4-(3-Chlorophenyl)-1-piperazinyl]-1-[5-methyl-1-(4-pyridyl)-4-pyrazolyl]-1-propanone Dihydrochloride 4-Acetyl-5-methyl-1-(4-pyridyl)pyrazole (0.53 g), 1-(3-chlorophenyl)piperazine hydrochloride (0.60 g), and p-formaldehyde (0.42 g) were reacted, and the product was worked up in the same manner as in Example 3-(1) to yield 0.40 g of the title compound.

Melting point: 196–199° C. (decomposition)

$^1$H-NMR (DMSO-$d_6$) δ: 2.73 (s, 3H), 3.1–3.25 (m, 4H), 3.5–4.0 (m, 8H), 6.88 (dd, 1H, J=8, 2 Hz), 6.99 (dd, 1H, J=8, 2 Hz), 7.08 (s, 1H), 7.27 (t, 1H, J=8 Hz), 7.88 (d, 2H, J=6 Hz), 8.52 (s, 1H), 8.87 (d, 2H, J=6 Hz).

2) preparation of 3-[4-(3-Chlorophenyl)-1-piperazinyl]-1-[5-methyl-1-(4-pyridyl)-4-pyrazolyl]-1-trans-propene Dihydrochloride The compound obtained in (1) above (335 mg) was reacted, and the product was worked up in the same manner as in Example 3-(2) to yield 236 mg of the title compound.

Melting point: 195–200° C. (decomposition)

$^1$H-NMR (DMSO-$d_6$) δ: 2.60 (s, 3H), 3.0–3.1 (m, 4H), 3.4–3.6 (m, 2H), 3.8–4.0 (m, 4H), 6.27 (dt, 1H, J=16, 8 Hz), 6.84 (d, 1H, J=16 Hz), 6.88 (d, 1H, J=8 Hz), 6.97 (d, 1H, J=8 Hz), 7.06 (s, 1H), 7.27 (t, 1H, J=8 Hz), 8.01 (d, 1H, J=6 Hz), 8.23 (s, 1H), 8.86 (d, 2H, J=6 Hz).

EXAMPLE 5

Synthesis of 3-[4-(3-Chloro-5-fluorophenyl)-1-piperazinyl]-1-[1-(3-chloro-2-pyridyl)-5-methyl-4-pyrazolyl]-1-trans-propene Hydrochloride

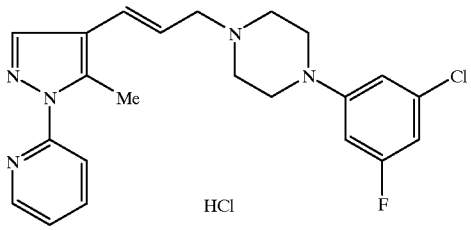

1) Preparation of 3-Chloro-2-hydrazinopyridine

To 30 ml of an n-butanol solution containing 7.0 g of 2,3-dichloropyridine were added 7.1 g of hydrazine monohydrate and 6.54 g of anhydrous potassium carbonate, and the mixture was heated under reflux for 17.5 hours. After cooling, the precipitate was collected by filtration to yield 6.07 g of the title compound.

$^1$H-NMR (CDCl$_3$) δ: 3.98 (br s, 2H), 6.22 (br s, 1H), 6.65 (dd, 1H, J=7, 5 Hz), 7.47 (dd, 1H, J=7, 1.5 Hz), 8.10 (dd, 1H, J=5, 1.5 Hz).

2) Preparation of 4-Acetyl-1-(3-chloro-2-pyridyl)-5-methylpyrazole

To an ethanol solution of 6.58 g of ethoxymethyleneacetylacetone was added 6.05 g of the compound obtained in (1) above, followed by stirring at room temperature for 15 minutes. The mixture was gradually heated to about 70° C. while stirring until the insoluble matter dissolved. After dissolution, the reaction mixture was heated at about 60° C. for 1 hour while stirring, followed by concentration. The residue was dissolved in chloroform, washed with water and then with a saturated sodium chloride aqueous solution, and dried over anhydrous sodium sulfate. The solvent was removed by evaporation. The residue was subjected to silica gel column chromatography using a mixture of chloroform-methanol (50:1 by volume) as a developing solvent. The fraction containing the desired compound was concentrated and recrystallized from a hexane-ethyl ether mixed solvent to yield 6.46 g of the title compound.

$^1$H-NMR (CDCl$_3$) δ: 2.50 (s, 3H), 2.52 (s, 3H), 7.47 (dd, 1H, J=8, 5 Hz), 7.97 (dd, 1H, J=8, 1.5 Hz), 8.08 (s, 1H), 8.56 (dd, 1H, J=5, 1.5 Hz).

3) preparation of 1-(3-Chloro-5-fluorophenyl) piperazine

To a toluene solution of 15.0 g of 1-bromo-3-chloro-5-fluorobenzene were added 24.6 g of piperazine anhydride, 1.69 g of dichlorobis(tri-o-tolylphoshine)palladium, and 9.64 g of sodium t-butoxide, and the mixture was heated at 100° C. for 38 hours in a nitrogen stream. The reaction mixture was cooled to room temperature, and the insoluble matter was removed by filtration through Celite. The solvent was removed by evaporation. Water was added to the residue, followed by extraction with a mixed solvent of chloroform-methanol (9:1 by volume). The extract was washed with a saturated sodium chloride aqueous solution and dried over anhydrous sodium sulfate. The solvent was evaporated off, and the residue was subjected to silica gel column chromatography using a mixture of chloroform-methanol (93:7 by volume) as a developing solvent. The fraction containing the desired compound was concentrated to yield 5.72 g of the title compound.

$^1$H-NMR (CDCl$_3$) δ: 2.8–3.2 (m, 4H), 3.0–3.3 (m, 4H), 6.46 (dt, 1H, J=12, 2 Hz), 6.53 (dt, 1H, J=8, 2 Hz), 6.64 (br s, 1H).

4) preparation of 3-[4-(3-Chloro-5-fluorophenyl)-1-piperazinyl]-1-[1-(3-chloro-2-pyridyl)-5-methyl-4-pyrazolyl]-1-propanone Hydrochloride The compound obtained in (2) above (390 mg), a hydrochloride of the compound obtained in (3) above (414 mg), and p-formaldehyde (1.5 g) were reacted in the same manner as in Example 3-(1). The precipitate was collected by filtration to yield 210 mg of the title compound.

Melting point: 182–190° C. (decomposition)

$^1$H-NMR (DMSO-d$_6$) δ: 2.41 (s, 3H), 3.1–3.3 (m, 4H), 3.4–3.6 (m, 4H), 3.5–3.7 (m, 2H), 3.9–4.1 (m, 2H), 6.76 (dm, 1H, J=8 Hz), 6.88 (dm, 1H, J=12 Hz), 6.93 (br s, 1H), 7.74 (dd, 1H, J=8, 4.5 Hz), 8.32 (dd, 1H, J=8, 2 Hz), 8.39 (s, 1H), 8.64 (dd, 1H, J=4.5, 2 Hz), 10.59 (br s, 1H).

5) Preparation of 3-[4-(3-Chloro-5-fluorophenyl)-1-piperazinyl]-1-[1-(3-chloro-2-pyridyl)-5-methyl-4-pyrazolyl]-1-trans-propene Hydrochloride To 200 mg of the compound obtained in (4) above were added 10 ml of ethanol and 10 ml of tetrahydrofuran, and 109 mg of sodium borohydride was added thereto in small portions over 1 hour while stirring under ice-cooling. The reaction mixture was neutralized by addition of a 1N hydrochloric acid/ethanol solution, and the solvent was removed by evaporation. Chloroform was added to the residue, the mixture was washed with a saturated sodium hydrogencarbonate aqueous solution, dried over anhydrous sodium sulfate, and the solvent was evaporated off. The residue was converted into a hydrochloride by addition of a 1N hydrochloric acid/ethanol solution, and 10 ml of tetrahydrofuran, 10 ml of dioxane, and 118 mg of p-toluenesulfonic acid monohydrate were added thereto. The reaction mixture was heated under reflux for 1.5 hours, followed by concentration. Chloroform was added to the residue, the mixture was washed successively with a saturated sodium hydrogencarbonate aqueous solution and a saturated sodium chloride aqueous solution, and dried over anhydrous sodium sulfate, and the solvent was evaporated off. The residue was subjected to column chromatography on silica gel using a mixture of chloroform-methanol (99:1 by volume) as an eluent. The fraction containing the desired compound was concentrated. A 1N hydrochloric acid/ethanol solution was added to the concentrate, followed by concentration. Recrystallization from ethanol yielded 78 mg of the title compound.

Melting point: 198–209° C. (decomposition)

$^1$H-NMR (DMSO-d$_6$) δ: 2.22 (s, 3H), 3.05–3.40 (m, 4H), 3.45–3.65 (m, 2H), 3.85–4.05 (m, 4H), 6.15 (dd, 1H, J=16, 7 Hz), 6.70–6.85 (m, 2H), 6.86 (dm, 1H, J=13 Hz), 6.91 (br s, 1H), 7.67 (dd, 1H, J=8, 5 Hz), 8.00 (s, 1H), 8.27 (dm, 1H, J=8 Hz), 8.60 (dm, 1H, J=5 Hz), 10.64 (br s, 1H).

EXAMPLE 6

Synthesis of 1-[1-(3-Chloro-2-pyridyl)-5-methyl-4-pyrazolyl]-3-[4-(3,5-difluorophenyl)-1-piperazinyl]-1-trans-propene Hydrochloride

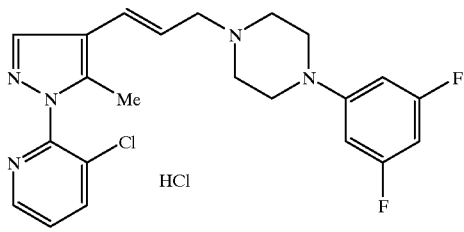

1) Preparation of 1-[1-(3-Chloro-2-pyridyl)-5-methyl-4-pyrazolyl]-3-[4-(3,5-difluorophenyl)-1-piperazinyl]-1-propanone In 40 ml of absolute ethanol was dissolved 0.72 g of 4-acetyl-1-(3-chloro-2-pyridyl)-5-methylpyrazole, and 1.38 g of 1-(3,5-difluorophenyl)piperazine, 7 ml of a 1N hydrochloric acid/ethanol solution, and 0.917 g of p-formaldehyde were added thereto, followed by refluxing for 20 hours. To the reaction mixture was further added 0.917 g of p-formaldehyde, followed by refluxing for 50 hours. After the reaction mixture was allowed to stand at room temperature for 21 hours, a saturated aqueous solution of sodium hydrogencarbonate was added thereto, and the mixture was extracted with chloroform three times. The organic layer was dried over anhydrous sodium sulfate, and the solvent was removed by evaporation. The residue was subjected to silica gel column chromatography using a mixture of chloroform-methanol (50:1 by volume) as a developing solvent. The fraction containing the desired compound was concentrated to yield 0.72 g of the title compound.

$^1$H-NMR (CDCl$_3$) δ: 2.51 (s, 3H), 2.66 (t, 4H, J=5 Hz), 2.89 (t, 2H, J=7 Hz), 3.08 (t, 2H, J=7 Hz), 3.21 (t, 4H, J=5 Hz), 6.25 (tm, 1H, J=9 Hz), 6.37 (dm, 2H, J=9 Hz), 7.48 (dd, 1H, J=8, 5 Hz), 7.97 (dd, 1H, J=8, 2 Hz), 8.12 (s, 1H), 8.56 (dd, 1H, J=5, 2 Hz).

2) Preparation of 1-[1-(3-Chloro-2-pyridyl)-5-methyl-4-pyrazolyl]-3-[4-(3,5-difluorophenyl)-1-piperazinyl]-1-trans-propene Hydrochloride In the same manner as in Example 5-(5), 280 mg of the title compound was obtained from 720 mg of the compound obtained in (1) above.

Melting point: 209–215° C. (decomposition)

$^1$H-NMR (DMSO-d$_6$) δ: 2.22 (s, 3H), 3.0–3.3 (m, 4H), 3.54 (m, 2H), 3.85–4.05 (m, 4H), 6.16 (dt, 1H, J=16, 7 Hz), 6.57 (br t, 1H, J=9 Hz), 6.73 (br d, 2H, J=9 Hz), 6.78 (d, 1H, J=16 Hz), 7.67 (dd, 1H, J=8, 5 Hz), 8.00 (s, 1H), 8.27 (dd, 1H, J=8, 2 Hz), 8.60 (dd, 1H, J=5, 2 Hz), 10.82 (br s, 1H).

EXAMPLE 7

Synthesis of 3-[4-(3,5-Dichlorophenyl)-1-piperazinyl]-1-[1-(3-chloro-2-pyridyl)-5-methyl-4-pyrazolyl]-1-trans-propene Hydrochloride

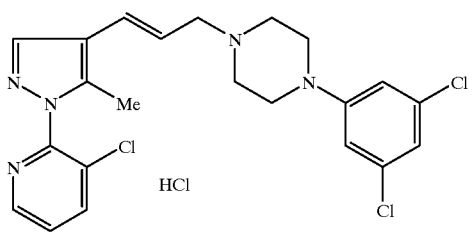

1) Preparation of 3-[4-(3,5-Dichlorophenyl)-1piperazinyl]-1-[1-(3-chloro-2-pyridyl)-5-methyl-4-pyrazolyl]-1-propanone Hydrochloride 4-Acetyl-1-(3-chloro-2-pyridyl)-5-methylpyrazole (0.70 g), 1-(3,5-dichlorophenyl)piperazine hydrochloride (0.735 g), and p-formaldehyde (1.8 g) were reacted, and the product was worked up in the same manner as in Example 5-(4) to yield 0.79 g of the title compound.

Melting point: 209–215° C. (decomposition)

$^1$H-NMR (DMSO-d$_6$) δ: 2.41 (s, 3H), 3.05–3.25 (m, 4H), 3.52 (m, 4H), 3.55–3.70 (m, 2H), 4.01 (m, 2H), 6.96 (s, 1H), 7.07 (s, 2H), 7.74 (dd, 1H, J=8, 5 Hz), 8.33 (dd, 1H, J=8, 2 Hz), 8.39 (s, 1H), 8.65 (dd, 1H, J=5, 2 Hz), 10.29 (br s, 1H).

2) Preparation of 3-[4-(3,5-Dichlorophenyl)-1-piperazinyl]-1-[1-(3-chloro-2-pyridyl)-5-methyl-4-pyrazolyl]-1-trans-propene Hydrochloride The compound obtained in (1) above (700 mg) was reacted and worked up in the same manner as in Example 5-(5) to yield 507 mg of the title compound.

Melting point: 217–220° C. (decomposition)

$^1$H-NMR (DMSO-d$_6$) δ: 2.22 (s, 3H), 3.0–3.25 (m, 4H), 3.5–3.6 (m, 2H), 3.85–4.1 (m, 4H), 6.14 (dt, 1H, J=16, 7 Hz), 6.78 (d, 1H, J=16 Hz), 6.96 (s, 1H), 7.05 (s, 2H), 7.67 (dd, 1H, J=8, 5 Hz), 8.01 (s, 1H), 8.27 (dd, 1H, J=8, 2 Hz), 8.60 (dd, 1H, J=5, 2 Hz), 10.41 (br s, 1H).

EXAMPLE 8

Synthesis of 3-[4-(3-Chlorophenyl)-1-piperazinyl]-1-[1-(3-chloro-2-pyridyl)-5-methyl-4-pyrazolyl]-1-propene Hydrochloride

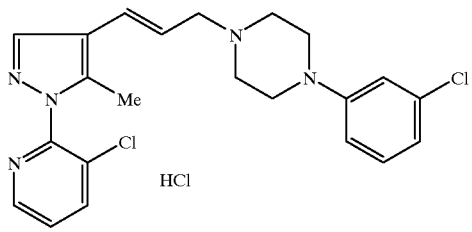

1) Preparation of 3-[4-(3-Chlorophenyl)-1-piperazinyl]-1-[1-(3-chloro-2-pyridyl)-5-methyl-4-pyrazolyl]-1-propanone 4-Acetyl-1-(3-chloro-2-pyridyl)-5-methylpyrazole (648 mg), 1-(3-chlorophenyl)pyrazole hydrochloride (641 mg), and p-formaldehyde (1.65 g) were reacted, and the product was worked up in the same manner as in Example 5-(4) to yield 439 mg of the title compound.

$^1$H-NMR (DMSO-d$_6$) δ: 2.41 (s, 3H), 3.1–3.3 (m, 4H), 3.4–3.7 (m, 6H), 3.8–4.0 (m, 2H), 6.87 (d, 1H, J=8 Hz), 6.99 (d, 1H, J=8 Hz), 7.08 (s, 1H), 7.27 (t, 1H, J=8 Hz), 7.75 (dd, 1H, J=8, 5 Hz), 8.33 (d, 1H, J=8 Hz), 8.40 (s, 1H), 8.65 (d, 1H, J=5 Hz).

2) Preparation of 3-[4-(3-Chlorophenyl)-1-piperazinyl]-1-[1-(3-chloro-2-pyridyl)-5-methyl-4-pyrazolyl]-1-propene Hydrochloride The compound obtained in (1) above (250 mg) was reacted and worked up in the same manner as in Example 1-(2) to yield 70 mg of the title compound.

Melting point: 95–108° C. (decomposition)

$^1$H-NMR (DMSO-d$_6$) δ: 2.50 (s, 3H), 3.0–3.2 (m, 4H), 3.4–3.6 (m, 2H), 3.8–4.0 (m, 4H), 6.16 (dt, 1H, J=16, 7 Hz), 6.78 (d, 1H, J=16 Hz), 6.88 (d, 1H, J=8 Hz), 6.97 (d, 1H, J=9 Hz), 7.05 (s, 1H), 7.27 (t, 1H, J=8 Hz), 7.67 (dd, 1H, J=5, 8 Hz), 8.01 (s, 1H), 8.28 (d, 1H, J=8 Hz), 8.60 (d, 1H, J=5 Hz).

EXAMPLE 9

Synthesis of 1-[1-(3-Chloro-2-pyridyl)-5-methyl-4-pyrazolyl]-3-[4-(3-cyano-5-fluoro-phenyl)-1-piperazinyl]-1-trans-propene Hydrochloride

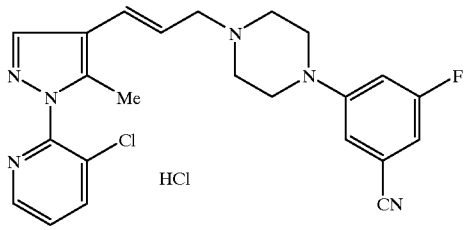

1) Preparation of 3-Fluoro-5-nitrobenzonitrile

Copper cyanide (5.03 g) was dried overnight and mixed with 15.0 g of 1-fluoro-3-iodo-5-nitrobenzene and 120 ml of dimethylformamide. The mixture was heated under reflux for 3 hours. After cooling, the reaction mixture was poured into ice-water containing about 4N hydrochloric acid, followed by stirring vigorously for 1 hour. Ethyl ether was added to the reaction mixture, followed by stirring vigorously for 1.5 hours. The insoluble matter was removed by filtration using Celite, and the filtrate was extracted with ethyl ether repeatedly. The ethyl ether layer was washed with water and a saturated sodium chloride aqueous solution, and dried over anhydrous sodium sulfate. The solvent was removed by evaporation. The residue was subjected to silica gel column chromatography using a mixture of hexane-ethyl acetate (50:3 by volume) as an eluate. The fraction containing the desired compound was concentrated to afford 8.00 g of the title compound.

$^1$H-NMR (CDCl$_3$) δ: 7.73 (dd, 1H, J=7, 1.5 Hz), 8.21 (dt, J=8, 2 Hz), 8.36 (m, 1H)

2) Preparation of 3-Amino-5-fluorobenzonitrile

To 14.1 g of the compound obtained in (1) were added 850 ml of ethanol and 5.0 g of 10% palladium-on-carbon to conduct catalytic hydrogenation. After completion of the reduction reaction, the solvent was removed by evaporation, and the residue was purified by silica gel column chromatography using a hexane-ethyl acetate mixed solvent (4:1 by volume) as an eluate. The fraction containing the desired compound was concentrated to yield 8.49 g of the title compound.

$^1$H-NMR (CDCl$_3$) δ: 4.01 (br s, 2H), 6.56 (dt, 1H, J=10, 2 Hz), 6.65–6.75 (m, 2H)

3) Preparation of 1-(3-Cyano-5-fluorophenyl) piperazine Hydrochloride

To a mixture of 8.49 g of the compound obtained in (2) above and 11.13 g of bis(2-chloroethyl)amine was added 120 ml of n-butanol, and the mixture was heat-refluxed for 63 hours. To the reaction mixture was added 8.62 g of anhydrous potassium carbonate, followed by heat-refluxing for 25 hours. After cooling, the insoluble matter (precipitate) was collected by filtration and dissolved in water. Thereto was added a 10% aqueous solution of sodium hydroxide, and the mixture was extracted with chloroform. The organic layer was washed with a saturated aqueous solution of sodium chloride and dried over anhydrous sulfate. The solvent was evaporated, and to the residue was added a 1N hydrochloric acid/ethanol solution, followed by concentration. Small amounts of ethanol and ethyl ether were added to the residue, and the insoluble matter was collected by filtration to yield 3.4 g of the title compound.

$^1$H-NMR (CDCl$_3$, free form) δ: 3.02 (m, 4H), 3.19 (m, 4H), 6.75 (d, 1H, J=2 Hz), 6.77 (m, 1H), 6.90 (m, 1H).

4) Preparation of 1-[1-(3-Chloro-2-pyridyl)-5-methyl-4-pyrazolyl]-3-[4-(3-cyano-5-fluorophenyl)-1-piperazinyl]-1-propanone Hydrochloride 1-(3-Cyano-5-fluorophenyl)piperazine hydrochloride (660 mg), 4-acetyl-1-(3-chloro-2-pyridyl)-5-methylpyrazole (760 mg), and p-formaldehyde (2.88 g) were reacted, and the product was worked up in the same manner as in Example 5-(4) to yield 486 mg of the title compound.

Melting point: 173–185° C. (decomposition)

$^1$H-NMR (DMSO-d$_6$) δ: 2.41 (s, 3H), 3.22 (m, 4H), 3.53 (m, 4H), 3.65 (m, 2H), 4.07 (m, 2H), 7.16 (dm, 1H, J=7 Hz), 7.26 (dm, 1H, J=12 Hz), 7.36 (m, 1H), 7.74 (dd, 1H, J=8, 5 Hz), 8.33 (dd, 1H, J=8, 1.5 Hz), 8.39 (s, 1H), 8.65 (dd, 1H, J=5, 1.5 Hz), 10.57 (br s, 1H).

5) Preparation of 1-[1-(3-Chloro-2-pyridyl)-5-methyl-4-pyrazolyl]-3-[4-(3-cyano-5-fluorophenyl)-1-piperazinyl]-1-trans-propene Hydrochloride The compound obtained in (4) above (480 mg) was reacted, and the product was worked up in the same manner as in Example 5-(5) to yield 285 mg of the title compound.

Melting point: 180–192° C. (decomposition)

$^1$H-NMR (DMSO-d$_6$) δ: 2.22 (s, 3H), 3.00–3.35 (m, 4H), 3.45–3.65 (m, 2H), 3.85–4.05 (m, 4H), 6.15 (dt, 1H, J=16, 7 Hz), 6.78 (dm, 1H, J=16 Hz), 7.16 (dm, 1H, J=8 Hz), 7.24 (dm, 1H, J=12 Hz), 7.33 (br s, 1H), 7.67 (dd, 1H, J=8, 5 Hz), 8.00 (s, 1H), 8.27 (dd, 1H, J=8, 1.5 Hz), 8.60 (dd, 1H, J=5, 1.5 Hz), 10.71 (br s, 1H).

EXAMPLE 10

Synthesis of 1-[1-(5-Chloro-2-pyridyl -5-methyl-4-pyrazolyl]-3-(4-(3,5-difluorophenyl)-1-piperazinyl]-1-trans-propene Hydrochloride

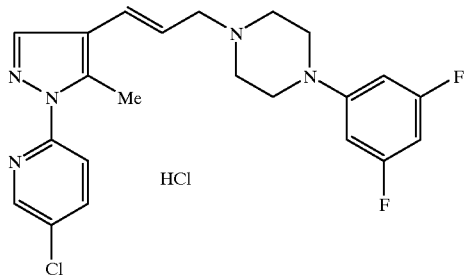

1) Preparation of 4-Acetyl-1-(5-chloro-2-pyridyl)-5-methylpyrazole

The same reaction as in Example 5-(2) was carried out, except for replacing the 3-chloro-2-hydrazinopyridine with 573 mg of 5-chloro-2-hydrazinopyridine. The reaction product was worked up in the same manner to yield 600 mg of the title compound.

Melting point: 130–132° C. (decomposition)

$^1$H-NMR (DMSO-d$_6$) δ: 2.47 (s, 3H), 2.79 (s, 3H), 7.87 (d, 1H, J=9 Hz), 8.18 (dd, 1H, J=9, 1.5 Hz), 8.32 (s, 1H), 8.63 (d, 1H, J=1.5 Hz).

2) Preparation of 1-[1-(5-Chloro-2-pyridyl)-5-methyl-4-pyrazolyl]-3-[4-(3,5-difluorophenyl)-1-piperazinyl]-1-propanone Hydrochloride 1-(3,5-Difluorophenyl)piperazine hydrochloride (710 mg), the compound obtained in (1) above (714 mg), and p-formaldehyde (3.6 g) were reacted, and the product was worked up in the same manner as in Example 5-(4) to yield 349 mg of the title compound.

Melting point: 179–190° C.

$^1$H-NMR (DMSO-d$_6$) δ: 2.84 (s, 3H), 3.19 (m, 4H), 3.51 (m, 4H), 3.64 (m, 2H), 3.98 (m, 2H), 6.55 (tm, 1H, J=9 Hz), 6.74 (d, 2H, J=9 Hz), 7.89 (d, 1H, J=9 Hz), 8.19 (dd, 1H, J=9, 3 Hz), 8.42 (s, 1H), 8.63 (d, 1H, J=3 Hz), 10.61 (br s, 1H).

3) Preparation of 1-[1-(5-Chloro-2-pyridyl)-5-methyl-4-pyrazolyl]-3-[4-(3,5-difluorophenyl)-1-piperazinyl]-1-trans-propene Hydrochloride The compound obtained in (2) (340 mg) was reacted in the same manner as in Example 5-(5), and the reaction mixture was worked up in the same manner to yield 260 mg of the title compound.

Melting point: 191–200° C. (decomposition)

$^1$H-NMR (DMSO-d$_6$) δ: 2.64 (s, 3H), 3.05–3.25 (m, 4H), 3.45–3.60 (m, 2H), 3.85–4.05 (m, 4H), 6.19 (dt, 1H, J=16, 7 Hz), 6.56 (tm, 1H, J=9 Hz), 6.72 (dm, 2H, J=9 Hz), 6.80 (d, 1H, J=16 Hz), 7.87 (d, 1H, J=9 Hz), 8.07 (s, 1H), 8.11 (dd, 1H, J=9, 3 Hz), 8.55 (d, 1H, J=3 Hz), 10.65 (br s, 1H).

EXAMPLE 11

Synthesis of 3-[4-(3,5-Dichlorophenyl)-1-piperazinyl]-1-[1-(5-chloro-2-pyridyl)-5-methyl-4-pyrazolyl]-1-trans-propene Hydrochloride

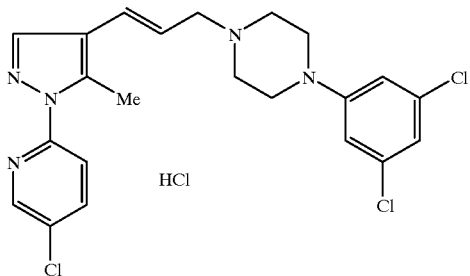

1) Preparation of 3-[4-(3,5-Dichlorophenyl)-1-piperazinyl]-1-[1-(5-chloro-2-pyridyl)-5-methyl-4-pyrazolyl]-1-propanone Hydrochloride 4-Acetyl-1-(5-chloro-2-pyridyl)-5-methylpyrazole (430 mg), 1-(3,5-dichlorophenyl)piperazine hydrochloride (804 mg), and p-formaldehyde (400 mg) were reacted, and the product was worked up in the same manner as in Example 5-(4) to yield 567 mg of the title compound.

Melting point: 200–220° C. (decomposition)

$^1$H-NMR (DMSO-d$_6$) δ: 2.83 (s, 3H), 3.1–3.3 (m, 4H), 3.5–3.9 (m, 8H), 3.9–4.1 (m, 2H), 6.96 (s, 1H), 7.08 (s, 2H), 7.89 (d, 1H, J=9 Hz), 8.20 (dd, 1H, J=9, 2 Hz), 8.43 (s, 1H), 8.65 (d, 1H, J=2 Hz).

2) Preparation of 3-[4-(3,5-Dichlorophenyl)-1-piperazinyl]-1-[1-(5-chloro-2-pyridyl)-5-methyl-4-pyrazolyl]-1-trans-propene Hydrochloride The compound obtained in (1) above (540 mg) was reacted, and the product was worked up in the same manner as in Example 5-(5) to yield 451 mg of the title compound.

Melting point: 225–235° C. (decomposition)

$^1$H-NMR (DMSO-d$_6$) δ: 2.63 (s, 3H), 3.0–3.3 (m, 4H), 3.4–3.6 (m, 2H), 3.9–4.1 (m, 4H), 6.1–6.3 (m, 1H), 6.80 (d, 1H, J=15 Hz), 6.97 (s, 1H), 7.06 (s, 2H), 7.87 (d, 1H, J=8 Hz), 8.09 (s, 1H), 8.12 (dd, 1H, J=9, 1.5 Hz), 8.57 (d, 1H, J=1.5 Hz).

EXAMPLE 12

Synthesis of 3-[4-(3,5-Difluorophenyl)-1-piperazinyl]-1-[1-(3-methoxy-2-pyridyl)-5-methyl-4-pyrazolyl]-1-trans-propene Hydrochloride

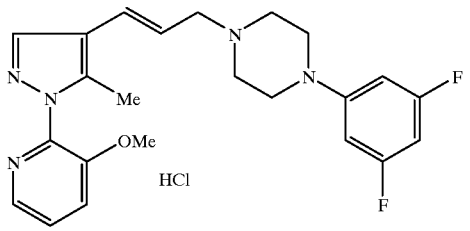

1) Preparation of 2-Hydrazino-3-methoxypyridine

To 50 ml of a butanol solution of 9.376 g of 2-chloro-3-methoxypyridine were added 16 ml of hydrazine monohydrate and 9.03 g of anhydrous potassium carbonate, and the mixture was heated under reflux for 20 hours. After cooling, the reaction mixture was poured into 200 ml of water and extracted with a mixed solvent of methanol-chloroform (1:9 by volume). The organic layer was washed with a saturated sodium chloride aqueous solution, and dried over anhydrous sodium sulfate. The solvent was removed by evaporation. The residue was subjected to silica gel column chromatography using a mixture of chloroform-methanol (20:1 by volume) as an eluate. The fraction containing the desired compound was concentrated to afford 5.952 g of the title compound.

$^1$H-NMR (CDCl$_3$) δ: 3.83 (s, 3H), 6.13 (br, 1H), 6.64 (dd, 1H, J=8, 5 Hz), 6.87 (dd, 1H, J=8, 1 Hz), 7.77 (dd, 1H, J=5, 1 Hz).

2) Preparation of 4-Acetyl-1-(3-methoxy-2-pyridyl)-5-methylpyrazole

The same reaction as in Example 5-(2) was carried out, expect for replacing the 3-chloro-2-hydrazinopyridine with 5.952 g of the compound obtained in (1) above. The reaction mixture was worked up in the same manner as in Example 5-(2) to yield 9.827 g.

$^1$H-NMR (CDCl$_3$) δ: 2.46 (s, 3H), 2.50 (s, 3H), 3.86 (s, 3H), 7.40–7.50 (m, 2H), 8.07 (s, 1H), 8.23 (m, 1H).

3) Preparation of 3-[4-(3,5-Difluorophenyl)-1-piperazinyl]-1-[1-(3-methoxy-2-pyridyl)-5-methyl-4-pyrazolyl]-1-propanone The compound obtained in (2) above (0.948 g), 1-(3,5-difluorophenyl)piperazine hydrochloride (0.961 g), and p-formaldehyde (5.09 g) were reacted, and the product was worked up in the same manner as in Example 6-(1) to yield 0.647 g of the title compound.

$^1$H-NMR (CDCl$_3$) δ: 2.47 (s, 3H), 2.66 (t, 4H, J=5 Hz), 2.89 (t, 2H, J=7 Hz), 3.08 (t, 2H, J=7 Hz), 3.22 (t, 4H, J=5 Hz), 3.87 (s, 3H), 6.25 (tt, 1H, J=9, 2 Hz), 6.36 (dd, 2H, J=10, 2 Hz), 7.40–7.50 (m, 2H), 8.11 (s, 1H), 8.24 (dd, 1H, J=4, 2 Hz).

4) Preparation of 3-[4-(3,5-Difluorophenyl)-1-piperazinyl]-1-[1-(3-methoxy-2-pyridyl)-5-methyl-4-pyrazolyl]-1-trans-propene Hydrochloride The compound obtained in (3) above (634 mg) was reacted, and the product was worked up in the same manner as in Example 5-(5) to yield 327 mg of the title compound.

Melting point: 197–201° C. (decomposition)

$^1$H-NMR (DMSO-d$_6$) δ: 2.14 (s, 3H), 3.0–3.2 (m, 2H), 3.24 (br t, 2H, J=12 Hz), 3.52 (br d, 2H, J=12 Hz), 3.82 (s, 3H), 3.85–4.0 (m, 4H), 6.11 (dt, 1H, J=16, 7 Hz), 6.56 (br t, 1H, J=9 Hz), 6.73 (br d, 2H, J=10 Hz), 6.76 (d, 1H, J=16 Hz), 7.59 (dd, 1H, J=8, 5 Hz), 7.77 (d, 1H, J=8 Hz), 7.89 (s, 1H), 8.17 (d, 1H, J=5 Hz), 11.06 (br s, 1H).

EXAMPLE 13

Synthesis of 3-[4-(3,5-Dichlorophenyl)-1-piperazinyl]-1-[1-(3-methoxy-2-pyridyl)-5-methyl-4-pyrazolyl]-1-trans-propene Hydrochloride

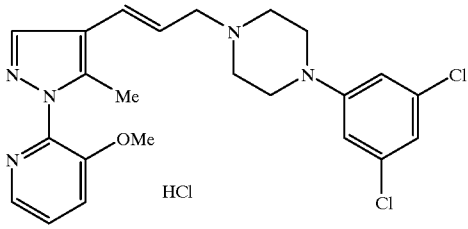

1) Preparation of 3-[4-(3,5-Dichlorophenyl)-1-piperazinyl]-1-[1-(3-methoxy-2-pyridyl)-5-methyl-4-pyrazolyl]-1-propanone 4-Acetyl-1-(3-methoxy-2-pyridyl)-5-methylpyrazole (1.136 g), 1-(3,5-dichlorophenyl)piperazine hydrochloride (1.22 g), and p-formaldehyde (4.41 g) were reacted, and the product was worked up in the same manner as in Example 6-(1) to yield 0.956 g of the title compound.

$^1$H-NMR (CDCl$_3$) δ: 2.46 (s, 3H), 2.65 (t, 4H, J=5 Hz), 2.89 (t, 2H, J=7 Hz), 3.07 (t, 2H, J=7 Hz), 3.22 (t, 4H, J=5 Hz), 3.86 (s, 3H), 6.74 (d, 2H, J=1.5 Hz), 6.79 (d, 1H, J=1.5 Hz), 7.40–7.50 (m, 2H), 8.11 (s, 1H), 8.23 (m, 1H).

2) Preparation of 3-[4-(3,5-Dichlorophenyl)-1-piperazinyl]-1-[1-(3-methoxy-2-pyridyl)-5-methyl-4-pyrazolyl]-1-trans-propene Hydrochloride The compound obtained in (1) (956 mg) was reacted, and the product was worked up in the same manner as in Example 5-(5) to yield 253 mg of the title compound.

Melting point: ≧199° C. (decomposition)

$^1$H-NMR (DMSO-d$_6$) δ: 2.14 (s, 3H), 3.0–3.3 (m, 4H), 3.53 (m, 2H), 3.82 (s, 3H), 3.9–4.1 (m, 4H), 6.09 (dt, 1H, J=16, 7 Hz), 6.75 (d, 1H, J=16 Hz), 6.96 (s, 1H), 7.05 (s, 2H), 7.60 (dd, 1H, J=8, 5 Hz), 7.77 (dd, 1H, J=8, 1 Hz), 7.91 (s, 1H), 8.17 (dd, 1H, J=5, 1 Hz), 10.59 (br s, 1H).

EXAMPLE 14

Synthesis of 3-[4-(3-Chlorophenyl)-1-piperazinyl]-1-[5-methyl-1-(2-pyrazinyl)-4-pyrazolyl]-1-trans-propene Hydrochloride

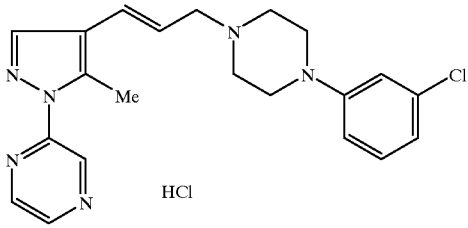

1) Preparation of 4-Acetyl-5-methyl-1-(2-pyrazinyl)pyrazole

To a solution of 0.96 g of 2-chloropyrazine in 10 ml of tetrahydrofuran was added 2.1 g of hydrazine monohydrate under cooling with ice. The mixture was stirred for 20 minutes while gradually raising the temperature to room temperature, followed by heating under reflux for 5 hours. After the reaction mixture was allowed to cool to room temperature, chloroform was added thereto, the mixture was washed with a saturated aqueous solution of sodium chloride and dried over anhydrous sodium sulfate, and the solvent was removed by evaporation. The residue (2.4 g) was dissolved in 20 ml of ethanol, and 3.8 g of ethoxymethyleneacetylacetone was added thereto in small portions. The reaction mixture was stirred at room temperature for 20 minutes and then heated under reflux for 5 hours. After the reaction mixture was allowed to cool to room temperature, the precipitated crystals were collected by filtration and recrystallized from ethanol to yield 0.93 g of the title compound.

$^1$H-NMR (CDCl$_3$) δ: 2.52 (s, 3H), 2.95 (s, 3H), 8.06 (s, 1H), 8.47 (dd, 1H, J=2.4, 1.5 Hz), 8.59 (d, 1H, J=2.4 Hz), 9.23 (d, 2H, J=1.5 Hz).

2) Preparation of 3-[4-(3-Chlorophenyl)-1-piperazinyl]-1-[5-methyl-1-(2-pyrazinyl)-4-pyrazolyl]-1-propanone Hydrochloride The compound obtained in (1) (0.93 g), 1-(3-chlorophenyl)piperazine hydrochloride (1.1 g), and p-formaldehyde (0.8 g) were reacted, and the product was worked up in the same manner as in Example 5-(4) to yield 1.5 g of the title compound.

Melting point: 209.9–211.1° C. (decomposition)

$^1$H-NMR (DMSO-d$_6$) δ: 2.85 (s, 3H), 3.1–3.4 (m, 6H), 3.4–3.7 (m, 4H), 3.8–4.0 (m, 2H), 6.87 (dd, 1H, J=8.3, 1.9 Hz), 6.98 (dd, 1H, J=8.3, 1.9 Hz), 7.08 (t, 1H, J=1.9 Hz), 7.27 (dt, 1H, J=8.3, 1.9 Hz), 8.50 (s, 1H), 8.66 (dd, 1H, J=2.4, 1.5 Hz), 8.76 (d, 1H, J=2.4 Hz), 9.16 (d, 2H, J=1.5 Hz).

3) Preparation of 3-[4-(3-Chlorophenyl)-1-piperazinyl]-1-[5-methyl-1-(2-pyrazinyl)-4-pyrazolyl]-1-trans-propene Hydrochloride The compound obtained in (2) above (500 mg) was reacted, and the product was worked up in the same manner as in Example 1-(2) to yield 70 mg of the title compound.

Melting point: 196.9–198.7° C. (decomposition)

$^1$H-NMR (DMSO-d$_6$) δ: 2.66 (s, 3H), 3.0–3.2 (m, 2H), 3.2–3.4 (m, 6H), 3.8–4.0 (m, 2H), 6.24 (dt, 1H, J=16.0, 7.3 Hz), 6.83 (d, 2H, J=16.0 Hz), 6.87 (dd, 1H, J=8.3, 1.9 Hz), 6.96 (dd, 1H, J=8.3, 1.9 Hz), 7.05 (t, 1H, J=1.9 Hz), 7.26 (dt, 1H, J=8.3, 1.9 Hz), 8.14 (s, 1H), 8.57 (dd, 1H, J=2.4, 1.5 Hz), 8.63 (d, 1H, J=2.4 Hz), 9.14 (d, 2H, J=1.5 Hz).

EXAMPLE 15

Synthesis of 3-[4-(2-Methylphenyl)-piperazinyl]-1-[5-methyl-1-(4-pyrimidinyl)-4-pyrazolyl]-1-trans-propene Hydrochloride

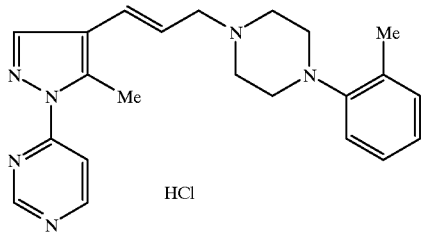

3-[4-(2-Methylphenyl)piperazinyl]-1-[5-methyl-1-(4-pyrimidinyl)-4-pyrazolyl]-1-propanone (200 mg) was reacted, and the product was worked up in the same manner as in Example 1-(2) to yield 17 mg of the title compound.

Melting point: 230–236° C. (decomposition)

$^1$H-NMR (DMSO-$d_6$) δ: 2.27 (s, 3H), 2.77 (s, 3H), 3.0–3.1 (m, 2H), 3.2–3.3 (m, 4H), 3.6-3.6 (m, 2H), 3.9–4.0 (m, 2H), 6.27 (dt, 1H, J=16, 8 Hz), 6.86 (d, 1H, J=16 Hz), 7.02 (t, 1H, J=7 Hz), 7.06 (d, 1H, J=7 Hz), 7.19 (t, 1H, J=7 Hz), 7.20 (d, 1H, J=7Hz), 7.95 (d, 1H, J=6 Hz), 8.22 (s, 1H), 8.88 (d, 1H, J=6 Hz), 9.10 (s, 1H).

EXAMPLE 16

Synthesis of 3-[4-(3,5-Dichlorophenyl)-1-piperazinyl]-1-[5-methyl-1-phenyl-4-2-pyrazolyl]-1-trans-propene Hydrochloride

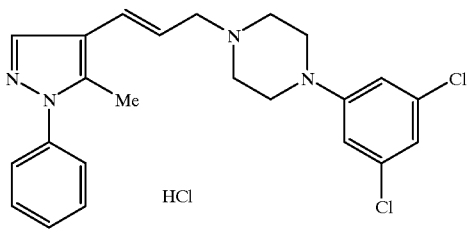

1) Preparation of 3-[4-(3,5-Dichlorophenyl)-1-piperazinyl]-1-[5-methyl-1-phenyl-4-pyrazolyl]-1-propanone Hydrochloride 4-Acetyl-5-methyl-1-phenylpyrazole (0.40 g), 1-(3,5-dichlorophenyl)piperazine hydrochloride (0.54 g), and p-formaldehyde (0.18 g) were reacted, and the product was worked up in the same manner as in Example 1-(1) to yield 0.59 g of the title compound.

Melting point: 206–209° C. (decomposition)

$^1$H-NMR (DMSO-$d_6$) δ: 2.54 (s, 3H), 3.1–3.3 (m, 4H), 3.45–3.55 (m, 4H), 3.55–3.65 (m, 2H), 3.95–4.05 (m, 2H), 6.96 (s, 1H), 7.08 (s, 2H), 7.5–7.6 (m, 5H), 8.36 (s, 1H).

2) Preparation of 3-[4-(3,5-Dichlorophenyl)-1-piperazinyl]-1-[5-methyl-1-phenyl-4-pyrazolyl]-1-trans-propene Hydrochloride The compound obtained in (1) above (527 mg) was reacted, and the product was worked up in the same manner as in Example 1-(2) to yield 1.31 g of the title compound.

Melting point: 207–210° C. (decomposition)

$^1$H-NMR (DMSO-$d_6$) δ: 2.36 (s, 3H), 3.05–3.25 (m, 4H), 3.45–3.6 (m, 2H), 3.9–4.05 (m, 4H), 6.12 (dt, 1H, J=15.6, 7.3 Hz), 6.78 (d, 1H, J=15.6 Hz), 6.97 (s, 1H), 7.06 (s, 2H), 7.4–7.6 (m, 5H), 7.95 (s, 1H).

EXAMPLE 17

Synthesis of 1-[1-(2-Fluorophenyl)-5-methyl-4-pyrazolyl]-3-[4-(3,5-difluorophenyl)-1-piperazinyl]-1-trans-propene Hydrochloride

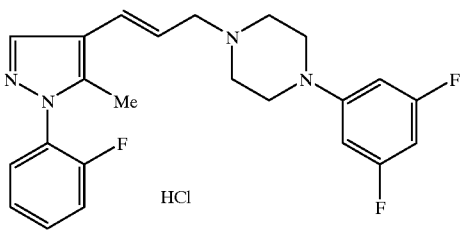

1) Preparation of 1-[1-(2-Fluorophenyl)-5-methyl-4-pyrazolyl]-3-[4-(3,5-difluorophenyl)-1-piperazinyl]-1-propanone 1-(3,5-Difluorophenyl)piperazine hydrochloride (591 mg), 4-acetyl-1-(2-fluorophenyl)-5-methylpyrazole (550 mg), and p-formaldehyde (3.0 g) were reacted, and the product was worked up in the same manner as in Example 6-(1) to yield 398 mg of the title compound.

$^1$H-NMR (CDCl$_3$) δ: 2.49 (d, 3H, J=1.5 Hz), 2.66 (m, 4H), 2.89 (t, 2H, J=7 Hz), 3.07 (t, 2H, J=7 Hz), 3.22 (m, 4H), 6.25 (tt, 1H, J=9, 2 Hz), 6.37 (dm, 2H, J=9 Hz), 7.25–7.55 (m, 4H), 8.09 (s, 1H).

2) Preparation of 1-[1-(2-Fluorophenyl)-5-methyl-4-pyrazolyl]-3-[4-(3,5-difluorophenyl)-1-piperazinyl]-1-trans-propene Hydrochloride The compound obtained in (1) above (395 mg) was reacted, and the product was worked up in the same manner as in Example 5-(5) to yield 238 mg of the title compound.

Melting point: 157–173° C.

$^1$H-NMR (DMSO-$d_6$) δ: 2.20 (s, 3H), 3.00–3.30 (m, 4H), 3.53 (dm, 2H, J=12 Hz), 3.85–4.05 (m, 4H), 6.13 (dt, 1H, J=16, 7 Hz), 6.56 (tm, 1H, J=9 Hz), 6.72 (dm, 2H, J=9 Hz), 6.77 (d, 1H, J=16 Hz), 7.30–7.65 (m, 4H), 7.98 (s, 1H), 10.77 (br s, 1H).

EXAMPLE 18

Synthesis of 3-[4-(3,5-Dichlorophenyl)-1-piperazinyl]-1-[1-(2-fluorophenyl)-5-methyl-4-pyrazolyl]-1-trans-propene Hydrochloride

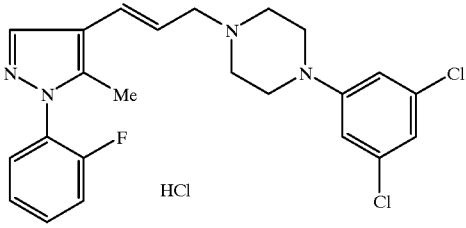

1) Preparation of 3-[4-(3,5-Dichlorophenyl)-1-piperazinyl]-1-[1-(2-fluorophenyl)-5-methyl-4-pyrazolyl]-1-propanone 1-(3,5-Dichlorophenyl)piperazine hydrochloride (674 mg), 1-(2-fluorophenyl)-4-acetyl-5-methylpyrazole (550 mg), and p-formaldehyde (3.0 g) were reacted, and the product was worked up in the same manner as in Example 6-(1) to yield 536 mg of the title compound.

$^1$H-NMR (CDCl$_3$) δ: 2.49 (d, 3H, J=1.5 Hz), 2.66 (m, 4H), 2.89 (t, 2H, J=7 Hz), 3.07 (t, 2H, J=7 Hz), 3.22 (m, 4H), 6.74 (m, 2H), 6.80 (m, 1H), 7.20–7.55 (m, 4H), 8.09 (s, 1H).

2) Preparation of 3-[4-(3,5-Dichlorophenyl)-1-piperazinyl]-1-[1-(2-fluorophenyl)-5-methyl-4-pyrazolyl]-1-trans-propene Hydrochloride The compound obtained in (1) above (530 mg) was reacted, and the product was worked up in the same manner as in Example 1-(2) to yield 274 mg of the title compound.

Melting point: 205–213° C. (decomposition)

$^1$H-NMR (DMSO-d$_6$) δ: 2.20 (s, 3H), 3.05–3.30 (m, 4H), 3.53 (dm, 2H, J=11 Hz), 3.85–4.05 (m, 4H), 6.11 (dt, 1H, J=16, 7 Hz), 6.77 (d, 1H, J=16 Hz), 6.94 (br s, 1H), 7.04 (br s, 2H), 7.30–7.65 (m, 4H), 7.98 (s, 1H), 10.58 (br s, 1H).

EXAMPLE 19

Synthesis of 1-[1-(2,4,6-Trichlorophenyl)-5-methyl-4-pyrazolyl]-3-[4-(3,5-difluoro-phenyl)-1-piperazinyl]-1-trans-propene Hydrochloride

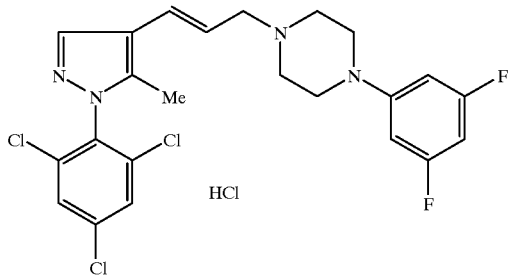

1) Preparation of 1-[1-(2,4,6-Trichlorophenyl)-5-methyl-4-pyrazolyl]-3-[4-(3,5-difluorophenyl)-1-piperazinyl]-1-propanone Hydrochloride 1-(3,5-Difluorophenyl)piperazine hydrochloride (385 mg), 4-acetyl-1-(2,4,6-trichlorophenyl)-5-methylpyrazole (500 mg), and p-formaldehyde (2.0 g) were reacted, and the product was worked up in the same manner as in Example 5-(4) to yield 180 mg of the title compound.

Melting point: 199–203° C. (decomposition)

$^1$H-NMR (DMSO-d$_6$) δ: 2.33 (s, 3H), 3.19 (m, 4H), 3.53 (m, 4H), 3.64 (m, 2H), 3.98 (m, 2H), 6.55 (tm, 1H, J=9 Hz), 6.74 (dm, 2H, J=9 Hz), 8.02 (s, 2H), 8.44 (s, 1H), 10.53 (br s, 1H).

2) Preparation of 1-[1-(2,4,6-Trichlorophenyl)-5-methyl-4-pyrazolyl]-3-[4-(3,5-difluorophenyl)-1-piperazinyl]-1-trans-propene Hydrochloride The compound obtained in (1) (175 mg) was reacted, and the product was worked up in the same manner as in Example 5-(5) to yield 40 mg of the title compound.

Melting point: 187–192° C. (decomposition)

$^1$H-NMR (DMSO-d$_6$) δ: 2.11 (s, 3H), 3.00–3.30 (m, 4H), 3.54 (dm, 2H, J=11 Hz), 3.85–4.05 (m, 4H), 6.15 (dt, 1H, J=16, 7 Hz), 6.56 (tm, 1H, J=9 Hz), 6.72 (dm, 2H, J=9 Hz), 6.77 (d, 1H, J=16 Hz), 7.98 (s, 2H), 8.05 (s, 1H), 10.61 (br s, 1H).

EXAMPLE 20

Synthesis of 1-[1-(2,4,6-Trichlorophenyl)-5-methyl-4-pyrazolyl]-3-[4-(3,5-dichloro-phenyl)-1-piperazinyl]-1-trans-propene Hydrochloride

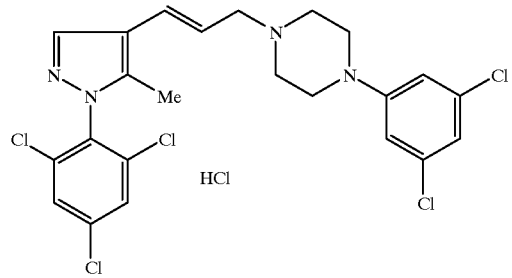

1) Preparation of 1-[1-(2,4,6-Trichlorophenyl)-5-methyl-4-pyrazolyl]-3-[4-(3,5-dichlorophenyl)-1-piperazinyl]-1-propanone Hydrochloride 1- (3,5-Dichlorophenyl)piperazine hydrochloride (440 mg), 4-acetyl-1-(2,4,6-trichlorophenyl)-5-methylpyrazole (500 mg), and p-formaldehyde (2.0 g) were reacted, and the product was worked up in the same manner as in Example 5-(4) to yield 584 mg of the title compound.

Melting point: 198–207° C. (decomposition)

$^1$H-NMR (DMSO-d$_6$) δ: 2.33 (s, 3H), 3.20 (m, 4H), 3.52 (m, 4H), 3.63 (m, 2H), 4.01 (m, 2H), 6.94 (br s, 1H), 7.07 (d, 2H, J=1.5 Hz), 8.03 (s, 2H), 8.45 (s, 1H), 10.52 (br s, 1H).

2) Preparation of 1-[1-(2,4,6-Trichlorophenyl)-5-methyl-4-pyrazolyl]-3-[4-(3,5-dichlorophenyl)-1-piperazinyl]-1-trans-propene Hydrochloride The compound obtained in (1) above (300 mg) was reacted, and the product was worked up in the same manner as in Example 5-(5) to yield 248 mg of the title compound.

Melting point: 215–221° C. (decomposition)

$^1$H-NMR (DMSO-d$_6$) δ: 2.11 (s, 3H), 3.0–3.3 (m, 4H), 3.53 (br d, 2H, J=11 Hz), 3.85–4.05 (m, 4H), 6.15 (dt, 1H, J=16, 7 Hz), 6.77 (d, 1H, J=16 Hz), 6.94 (d, 1H, J=1.5 Hz), 7.04 (d, 2H, J=1.5 Hz), 7.97 (s, 2H), 8.04 (s, 1H), 10.64 (br s, 1H).

EXAMPLE 21

Synthesis of 3-[4-(3-Chlorophenyl)-1-piperazinyl]-1-[5-methyl-1-(2-thiazolyl)-4-pyrazolyl]-1-trans-propene Hydrochloride

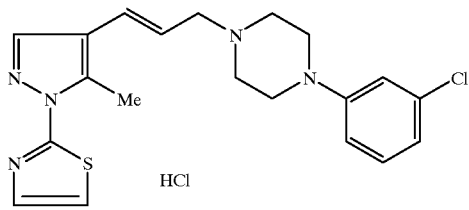

1) Preparation of 4-Acetyl-1-(2-thiazolyl)-5-methylpyrazole

Ethoxymethyleneacetylacetone (3.5 g) and 2-hydrazinothiazole (2.6 g) were reacted, and the product was worked up in the same manner as in Example 5-(2) to yield 3.0 g of the title compound.

$^1$H-NMR (DMSO-$d_6$) δ: 2.51 (s, 3H), 2.66 (s, 3H), 7.77 (s, 1H), 8.24 (s, 2H).

2) Preparation of 3-[4-(3-Chlorophenyl)-1-piperazinyl]-1-[5-methyl-1-(2-thiazolyl)-4-pyrazolyl]-1-propanone Hydrochloride The compound obtained in (1) (2.0 g), 1-(3-chlorophenyl)piperazine hydrochloride (2.3 g), and p-formaldehyde (6.0 g) were reacted, and the product was worked up in the same manner as in Example 6-(1). The resulting compound was converted to its hydrochloride with a 1N hydrochloric acid/ethanol solution and recrystallized from ethanol to yield 566 mg of the title compound.

Melting point: 193.5–195.0 (decomposition)

$^1$H-NMR (DMSO-$d_6$) δ: 2.53 (s, 3H), 3.0–3.2 (m, 4H), 3.2–3.4 (m, 4H), 3.5–3.6 (m, 2H), 3.6–3.8 (m, 2H), 6.88 (d, 2H, J=7.8 Hz), 6.98 (d, 2H, J=7.8 Hz), 7.08 (s, 1H), 7.27 (t, 1H, J=7.8 Hz), 7.75 (d, 1H, J=3.5 Hz), 8.25 (d, 1H, J=3.5 Hz).

3) Preparation of 3-[4-(3-Chlorophenyl)-1-piperazinyl]-1-[5-methyl-1-(2-thiazolyl)-4-pyrazolyl]-1-trans-propene Hydrochloride In a mixed solvent of 10 ml of absolute ethanol and 10 ml of anhydrous tetrahydrofuran was dissolved 346 mg of the compound obtained in (2) above, and the solution was cooled to −10° C. To the solution was added 280 mg of sodium borohydride, and the mixture was stirred at that temperature for 2 hours. A 1N hydrochloric acid/ethanol solution was added to the reaction mixture for neutralization, and the solvent was removed by evaporation. To the residue were added 10 ml of dioxane, 10 ml of tetrahydrofuran, and 300 mg of p-toluenesulfonic acid monohydrate, followed by heating under reflux for 1 hour. The solvent was removed by evaporation, and chloroform was added to the residue. The mixture was washed successively with a saturated aqueous solution of sodium hydrogencarbonate and a saturated aqueous solution of sodium chloride, and dried over anhydrous sodium sulfate. The solvent was removed by evaporation. The residue was subjected to column chromatography on silica gel using a mixture of chloroform-methanol (10:1 by volume) as a developing solvent. The fraction containing the desired compound was concentrated. A 1N hydrochloric acid/ethanol solution was added to the residue, followed by concentration. Recrystallization of the residue from ethanol yielded 300 mg of the title compound.

Melting point: 180.2–182.3° C. (decomposition)

$^1$H-NMR (DMSO-$d_6$) δ: 2.60 (s, 3H), 3.1–3.2 (m, 2H), 3.2–3.3 (m, 4H), 3.4–3.6 (m, 4H), 3.6–3.8 (m, 2H), 6.32 (dt, 1H, J=16, 8 Hz), 6.82 (d, 1H, J=16 Hz), 6.85 (d, 2H, J=8 Hz), 6.95 (d, 2H, J=8 Hz), 7.03 (s, 1H), 7.23 (t, 1H, J=8 Hz), 7.74 (d, 1H, J=3 Hz), 8.27 (d, 1H, J=3 Hz).

EXAMPLE 22

Synthesis of 1-[1-(2-Amidino)-5-methyl-4-pyrazolyl]-3-[4-(3-chlorophenyl)-1-piperazinyl]-1-trans-propene Hydrochloride

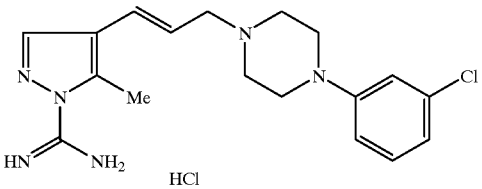

1) Preparation of 4-Acetyl-1-(2-amidino)-5-methylpyrazole

Ethoxymethyleneacetylacetone (4.2 g) and aminoguanidine monohydrochloride (3.0 g) were reacted, and the product was worked up in the same manner as in Example 5-(2) to furnish 0.302 g of the title compound.

$^1$H-NMR (DMSO-$d_6$) δ: 2.35 (s, 3H), 2.68 (s, 3H), 7.75 (br s, 2H), 8.53 (s, 1H), 9.75 (br s, 1H).

2) Preparation of 1-[1-(2-Amidino)-5-methyl-4-pyrazolyl]-3-[4-(3-chlorophenyl)-1-piperazinyl]-1-propanone Hydrochloride The compound obtained in (1) (595 mg), 1-(3-chlorophenyl)piperazine hydrochloride (834 mg), and p-formaldehyde (0.8 g) were reacted, and the product was worked up in the same manner as in Example 21-(2) to yield 1.1 g of the title compound.

Melting point: 154.2–155.8° C. (decomposition)

$^1$H-NMR (DMSO-$d_6$) δ: 2.36 (s, 3H), 3.1–3.2 (m, 4H), 3.3–3.5 (m, 4H), 3.5–3.6 (m, 2H), 3.8–3.9 (m, 2H), 6.88 (d, 2H, J=7.8 Hz), 6.97 (d, 2H, J=7.8 Hz), 7.06 (s, 1H), 7.26 (t, 1H, J=7.8 Hz), 7.6–7.7 (m, 2H), 8.12 (s, 1H), 9.1–9.2 (m, 1H).

3) Preparation of 1-[1-(2-Amidino)-5-methyl-4-pyrazolyl]-3-[4-(3-chlorophenyl)-1-piperazinyl]-1-trans-propene Hydrochloride The compound obtained in (2) (718 mg) was reacted, and the product was worked up in the same manner as in Example 21-(3) to yield 15 mg of the title compound.

Melting point: 142.3–144.2° C. (decomposition)

$^1$H-NMR (DMSO-$d_6$) δ: 2.33 (s, 3H), 3.1–3.2 (m, 2H), 3.3–3.5 (m, 4H), 3.5–3.7 (m, 2H), 3.7–3.8 (m, 2H), 6.22 (dt, 1H, J=16.0, 7.3 Hz), 6.83 (d, 1H, J=16.0 Hz), 6.87 (d, 2H, J=7.8 Hz), 6.97 (d, 2H, J=7.8 Hz), 7.05 (s, 1H), 7.26 (t, 1H, J=7.8 Hz), 8.07 (s, 1H), 9.15 (br s, 1H).

EXAMPLE 23

Synthesis of 1-[1-(3-Chloro-2-pyridyl)-5-methyl-4-pyrazolyl]-3-[4-(2,5-difluorophenyl)-1-piperazinyl]-1-trans-propene Hydrochloride

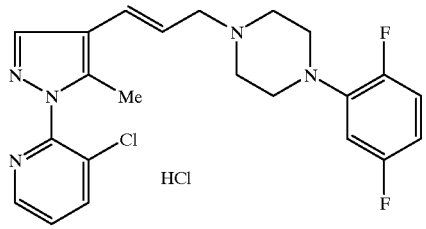

1) Preparation of 1-[1-(3-Chloro-2-pyridyl)-5-methyl-4-pyrazolyl]-3-[4-(2,5-difluorophenyl)-1-piperazinyl]-1-propanone 1-(2,5-Difluorophenyl)piperazine hydrochloride (500 mg), 4-acetyl-1-(3-chloro-2-pyridyl)-5-methylpyrazole (505 mg), and p-formaldehyde (1.92 g) were reacted, and the product was worked up in the same manner as in Example 6-(1), to gives 355 mg of the title compound.

$^1$H-NMR (CDCl$_3$) δ: 2.51 (s, 3H), 2.71 (m, 4H), 2.91 (t, 2H, J=7 Hz), 3.09 (t, 2H, J=7 Hz), 3.13 (m, 4H), 6.50–6.70 (m, 2H), 6.90–7.00 (m, 1H), 7.47 (dd, 1H, J=8, 5 Hz), 7.98 (dd, 1H, J=8, 1.5 Hz), 8.12 (s, 1H), 8.56 (dd, 1H, J=5, 1.5 Hz ).

2) Preparation of 1-[1-(3-Chloro-2-pyridyl)-5-methyl-4-pyrazolyl]-3-[4-(2,5-difluorophenyl)-1-piperazinyl]-1-trans-propene Hydrochloride The compound obtained in (1) above was reacted and worked up in the same manner as in Example 5-(5) to give 102 mg of the title compound.

Melting point: 182–202° C. (decomposition)

$^1$H-NMR (DMSO-d$_6$) δ: 2.23 (s, 3H), 3.10–3.30 (m, 4H), 3.50–3.70 (m, 4H), 3.90–4.00 (m, 2H), 6.16 (dt, 1H, J=16, 8 Hz), 6.79 (d, 1H, J=16 Hz), 6.75–6.90 (m, 1H), 6.90–7.05 (m, 1H), 7.20 (ddd, 1H, J=14, 9, 5 Hz), 7.66 (dd, 1H, J=8, 4 Hz), 8.00 (s, 1H), 8.26 (dd, 1H, J=8, 1.5 Hz), 8.60 (dd, 1H, J=4, 1.5 Hz), 10.60 (brs, 1H).

EXAMPLE 24

Synthesis of 3-[4-(3,5-Difluorophenyl)-1-piperazinyl]-1-[1-(3-iodo-2-pyridyl)-5-methyl-4-pyrazolyl]-1-trans-propene Hydrochloride and 3-[4-(3,5-Difluorophenyl)-1-piperazinyl]-1-[1-(2-pyridyl)-5-methyl-4-pyrazolyl-1-trans-propene Hydrochloride

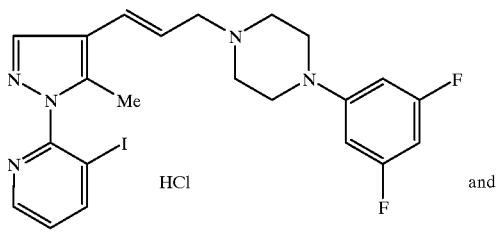

and

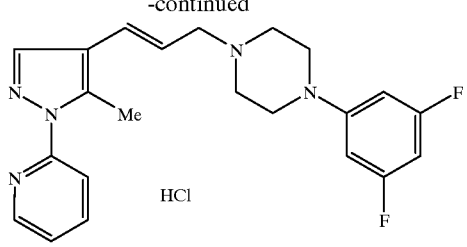

1) Preparation of 2-Fluoro-3-iodopyridine

To 76 ml of an anhydrous tetrahydrofuran (THF) solution of 10 ml of diisopropylamine was added 48.6 ml (1.57 M solution in hexane) of n-butyllithium at −78° C., and the mixture was stirred at that temperature for 30 minutes. To the reaction mixture was added 10 ml of a THF solution of 7.4 g of 2-fluoropyrimidine, followed by stirring at −78° C. for 30 minutes. To the reaction mixture was further added 30 ml of a THF solution of 19.4 g of iodine, followed by stirring at −78° C. for 30 minutes. The temperature was raised to 0° C., at which the reaction mixture was stirred for 24 hours. The reaction mixture was poured into 300 ml of a 8% sodium sulfite aqueous solution and extracted with diethyl ether. The organic layer was washed successively with water and a saturated sodium chloride aqueous solution and dried. The solvent was evaporated, and the residue was subjected to silica gel column chromatography using a mixture of ethyl acetate and hexane (1:9 by volume) as a developing solution. The fraction containing the desired compound was concentrated to yield 14.3 g of the title compound as a pale yellow solid.

$^1$H-NMR (CDCl$_3$) δ: 6.96 (dt, 1H, J=2, 5 Hz), 8.00–8.20 (m, 2H).

2) Preparation of 4-Acetyl-1-(3-iodo-2-pyridyl)-5-methylpyrazole

To 30 ml of a butanol solution of 6.27 g of the compound obtained in (1) above were added 4.4 ml of hydrazine monohydrate and 4.15 g of potassium carbonate. The mixture was heated under reflux for 8 hours, followed by allowing to stand at room temperature for 12 hours. The precipitated crystals were collected by filtration and dried over phosphorus pentoxide under reduced pressure. The resulting crystals weighing 3.08 g was added to 20 ml of an ethanolic solution of 2.42 g of ethoxymethyleneacetylalcetone, and the mixture was stirred at room temperature for 30 minutes and at 60° C. for 2 hours. After cooling, the solvent was removed by evaporation. The residue was subjected to silica gel column chromatography using a 1:1 (by volume) mixture of ethyl acetate and hexane as a developing solvent. The fraction containing the desired compound was concentrated to afford 3.67 g of the title compound.

$^1$H-NMR (CDCl$_3$) δ: 2.48 (s, 3H), 2.52 (s, 3H), 7.2 (dd, 1H, J=5, 8 Hz), 8.07 (s, 1H), 8.36 (dd, 1H, J=1, 8 Hz), 8.60 (dd, 1H, J=1, 5 Hz).

3) Preparation of 3-[4-(3,5-Difluorophenyl)-1-piperazinyl]-1-[1-(3-iodo-2-pyridyl)-5-methyl-4-pyrazolyl]-1-propanone The compound obtained in (2) (500 mg), 1-(3,5-difluorophenyl)piperazine hydrochloride (725 mg), and p-formaldehyde (665 mg) were reacted, and the reaction product was worked up in the same manner as in Example 6-(1) to obtain 498 mg of the title compound.

$^1$H-NMR (CDCl$_3$) δ: 2.49 (s, 3H), 2.66 (t, 4H, J=5 Hz), 2.89 (t, 2H, J=7 Hz), 3.09 (t, 2H, J=7 Hz), 3.21 (t, 4H, J=5 Hz), 6.25 (tt, 1H, J=2, 9 Hz), 6.36 (dd, 2H, J=2, 9 Hz), 7.22 (dd, 1H, J=5, 8 Hz), 8.11 (s, 1H), 8.35 (dd, 1H, J=8, 2 Hz), 8.60 (dd, 1H, J=5, 2 Hz).

4) Preparation of 3-[4-(3,5-Difluorophenyl)-1-piperazinyl]-1-[1-(3-iodo-2-pyridyl)-5-methyl-4-pyrazolyl]-1-trans-propene Hydrochloride and 3-[4-(3,5-Difluorophenyl)-1-piperazinyl]-1-[1-(2-pyridyl)-5-methyl-4-pyrazolyl]-1-trans-propene Hydrochloride The compound obtained in (3) above (498 mg) was reacted and worked up in the same manner as in Example 5-(5) to yield 78 mg of 3-[4-(3,5-difluorophenyl)-1-piperazinyl]-1-[1-(3-iodo-2-pyridyl)-5-methyl-4-pyrazolyl]-1-trans-propene hydrochloride as a low-polar compound and 127 mg of 3-[4-(3,5-difluorophenyl)-1-piperazinyl]-1-[1-(2-pyridyl)-5-methyl-4-pyrazolyl]-1-trans-propene hydrochloride as a high-polar compound.

3-[4-(3,5-Difluorophenyl)-1-piperazinyl]-1-[1-(3-iodo-2-pyridyl)-5-methyl-4-pyrazolyl]-1-trans-propene hydrochloride Melting point: 212–216° C. (decomposition)

$^1$H-NMR (DMSO-d$_6$) δ: 2.25 (s, 3H), 3.05–3.30 (m, 4H), 3.50–3.60 (m, 2H), 3.85–4.05 (m, 4H), 6.17 (dt, 1H, J=16, 7 Hz), 6.56 (t, 1H, J=9 Hz), 6.72 (d, 2H, J=9 Hz), 6.79 (d, 1H, J=16 Hz), 7.38 (dd, 1H, J=4, 8 Hz), 7.96 (s, 1H), 8.54 (dd, 1H, J=1, 8 Hz), 8.61 (dd, 1H, J=4, 1 Hz), 10.65 (br, 1H).

3-[4-(3,5-Difluorophenyl)-1-piperazinyl]-1-[1-(2-pyridyl)-5-methyl-4-pyrazolyl]-1-trans-propene Hydrochloride Melting point: 182–185° C. (decomposition)

$^1$H-NMR (DMSO-d$_6$) δ: 2.65 (s, 3H), 3.05–3.30 (m, 4H), 3.45–3.55 (m, 2H), 3.85–4.05 (m, 4H), 6.19 (dt, 1H, J=16, 7 Hz), 6.56 (t, 1H, J=9 Hz), 6.72 (d, 2H, J=9 Hz), 6.81 (d, 1H, J=16 Hz), 7.39 (dd, 1H, J=5, 7 Hz), 7.83 (d, 1H, J=8 Hz), 8.00 (m, 1H), 8.03 (s, 1H), 8.50 (dd, 1H, J=1, 5 Hz), 11.04 (br, 1H).

EXAMPLE 25

Synthesis of 3-[4-(3,5-Difluorophenyl)-1-piperazinyl]-1-[1-(3-hydroxy-2-pyridyl)-5-methyl-4-pyrazolyl]-1-trans-propene Hydrochloride

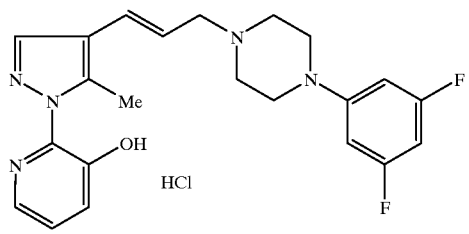

1) Preparation of 2-Chloro-3-(4-methoxybenzyloxy) pyridine

2-Chloro-3-pyridinol (1.3 g), 1.88 g of p-methoxybenzyl chloride, and 1.4 g of potassium carbonate were added to 10 ml of dimethylformamide, followed by stirring at 60° C. for 17 hours. The reaction mixture was diluted with ethyl acetate and washed successively with water and a saturated sodium chloride aqueous solution. After drying, the solvent was removed by evaporation, and the residue was subjected to silica gel column chromatography using a 1:4 (by volume) mixture of ethyl acetate and hexane as a developing solution. The fraction containing the desired compound was concentrated to afford 2.18 g of the title compound.

$^1$H-NMR (CDCl$_3$) δ: 3.82 (s, 3H), 5.11 (s, 2H), 6.92 (brd, 2H, J=8 Hz), 7.15 (dd, 1H, J=5, 8 Hz), 7.23 (dd, 1H, J=2, 8 Hz), 7.37 (brd, 2H, J=8 Hz), 7.99 (dd, 1H, J=2, 5 Hz).

2) Preparation of 2-Hydrazino-3-(4-methoxybenzyloxy)pyridine

The procedure of Example 12-(1) was repeated, except for replacing 2-chloro-3-methoxypyridine with 2.15 g of the compound obtained in (1) above, to obtain 359 mg of the title compound.

$^1$H-NMR (CDCl$_3$) δ: 3.83 (s, 3H), 3.8–4.0 (br, 2H), 4.99 (s, 2H), 6.61 (dd, 1H, J=5, 8 Hz), 6.92 (d, 2H, J=8 Hz), 6.93 (d, 1H, J=8 Hz), 7.32(d, 2H, J=8 Hz), 7.79 (d, 1H, J=5 Hz).

3) Preparation of 4-Acetyl-1-{3-(4-methoxybenzyloxy)-2-pyridyl}-5-methylpyrazole The procedure of Example 5-(2) was repeated, except for replacing 3-chloro-2-hydrazinopyridine with 359 mg of the compound obtained in (2) above, to obtain 431 mg of the title compound.

$^1$H-NMR (CDCl$_3$) δ: 2.44 (s, 3H), 2.50 (s, 3H), 3.79 (s, 3H), 5.05 (s, 2H), 6.85 (d, 2H, J=9 Hz), 7.18 (d, 2H, J=9 Hz), 7.39 (dd, 1H, J=5, 8 Hz), 7.46 (dd, 1H, J=1, 8 Hz), 8.07 (s, 1H), 8.23 (dd, 1H, J=1, 5 Hz).

4) Preparation of 3-[4-(3,5-Difluorophenyl)-1-piperazinyl]-1-[1-[3-(4-methoxybenzyloxy)-2-pyridyl]-5-methyl-4-pyrazolyl]-1-propanone The compound obtained in (3) above (430 mg), 288 mg of 1-(3,5-difluorophenyl)piperazine hydrochloride, and 383 mg of p-formaldehyde were reacted and worked up in the same manner as in Example 6-(1) to give 224 mg of the title compound.

$^1$H-NMR (CDCl$_3$) δ: 2.42 (s, 3H), 2.65 (t, 4H, J=5 Hz), 2.88 (t, 2H, J=7 Hz), 3.06 (t, 2H, J=7 Hz), 3.20 (t, 4H, J=5 Hz), 3.79 (s, 3H), 5.05 (s, 2H), 6.24 (tt, 1H, J=2, 9 Hz), 6.36 (dd, 2H, J=2, 11 Hz), 6.85 (d, 2H, J=9 Hz), 7.18 (d, 2H, J=9 Hz), 7.39 (dd, 1H, J=5, 8 Hz), 7.47 (dd, 1H, J=1, 8 Hz), 8.11 (s, 1H), 8.23 (dd, 1H, J=1, 5 Hz).

5) Preparation of 3-[4-(3,5-Difluorophenyl)-1-piperazinyl]-1-[1-(3-hydroxy-2-pyridyl)-5-methyl-4-pyrazolyl]-1-trans-propene Hydrochloride The compound obtained in (4) above (224 mg) was reacted and worked up in the same manner as in Example 5-(5) to afford 38 mg of the title compound.

Melting point: 162–164° C. (decomposition)

$^1$H-NMR (DMSO-d$_6$) δ: 2.25 (s, 3H), 3.05–3.30 (m, 4H), 3.45–3.55 (m, 2H), 3.85–4.05 (m, 4H), 6.13 (dt, 1H, J=16, 7 Hz), 6.56 (t, 1H, J=9 Hz), 6.72 (d, 2H, J=9 Hz), 6.78 (d, 1H, J=16 Hz), 7.39 (dd, 1H, J=4, 8 Hz), 7.54 (d, 1H, J=8 Hz), 7.93 (s, 1H), 8.03 (d, 1H, J=4 Hz), 11.04 (br, 1H).

EXAMPLE 26

Synthesis of 3-[4-(3,5-Difluorophenyl)-1-piperazinyl]-1-[5-methyl-1-(3-methylthio-2-pyridyl)-4-pyrazolyl]-1-trans-propene Hydrochloride

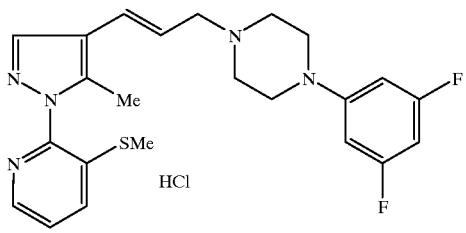

1) Preparation of 2-Fluoro-3-methylthiopyridine

To 140 ml of an anhydrous THF solution of 7.7 g of diisopropylamine was added 50 ml (1.6 M solution in hexane) of n-butyllithium at −78° C., and the mixture was stirred at that temperature for 30 minutes. To the reaction mixture was added 10 ml of a THF solution of 7.4 g of 2-fluoropyrimidine, followed by stirring at the same temperature for 30 minutes. To the reaction mixture was further added a THF solution of 8.61 g of dimethyl disulfide, followed by stirring at the same temperature for 20 minutes. The reaction mixture was poured into about 200 ml of water, and the aqueous layer was extracted twice with ethyl acetate. The organic layers were combined and washed with a saturated sodium chloride aqueous solution and dried over anhydrous sodium sulfate. The solvent was evaporated, and the residue was subjected to silica gel column chromatography using a mixture of ethyl acetate and hexane (1:19 by volume) as a developing solution. The fraction containing the desired compound was concentrated to yield 6.11 g of the title compound.

$^1$H-NMR (CDCl$_3$) δ: 2.49 (s, 3H), 7.16 (ddd, 1H, J=8, 5, 2 Hz), 7.62 (ddd, 1H, J=9, 8, 2 Hz), 7.98 (dm, 1H, J=5 Hz).

2) Preparation of 2-Hydrazino-3-methylthiopyridine

The procedure of Example 12-(1) was repeated, except for replacing 2-chloro-3-methoxypyridine with 6.1 g of the compound obtained in (1) above, to yield 6.35 g of the title compound.

$^1$H-NMR (CDCl$_3$) δ: 4.00 (brs, 2H), 6.54 (brs, 1H), 6.66 (dd, 1H, J=7, 5 Hz), 7.54 (dd, 1H, J=7, 1.5 Hz), 8.11 (dm, 1H, J=5 Hz).

3) Preparation of 4-Acetyl-1-(3-methylthio-2-pyridyl)-5-methylpyrazole

The procedure of Example 5-(2) was repeated, except for replacing 3-chloro-2-hydrazinopyridine with 6.35 g of the compound obtained in (2) above, to yield 9.78 g of the title compound.

$^1$H-NMR (CDCl$_3$) δ: 2.42 (s, 3H), 2.51 (s, 3H), 2.52 (s, 3H), 7.43 (dd, 1H, J=8, 4.5 Hz), 7.73 (dd, 1H, J=8, 1.5 Hz), 8.07 (s, 1H), 8.36 (dd, 1H, J=4.5, 1.5 Hz).

4) Preparation of 3-[4-(3,5-Difluorophenyl)-1-piperazinyl]-1-[5-methyl-1-(3-methylthio-2-pyridyl)-4-pyrazolyl]-1-propanone The compound obtained in (3) above (1.0 g), 946 mg of 1-(3,5-difluorophenyl)piperazine hydrochloride, and 4.8 g of p-formaldehyde were reacted, and the product was worked up in the same manner as in Example 6-(1) to afford 759 mg of the title compound.

$^1$H-NMR (CDCl$_3$) δ: 2.42 (s, 3H), 2.52 (s, 3H), 2.65 (m, 4H), 2.88 (t, 2H, J=7 Hz), 3.07 (t, 2H, J=7 Hz), 3.21 (m, 4H), 6.25 (tt, 1H, J=9, 2 Hz), 6.36 (dd, 2H, J=11, 2 Hz), 7.43 (dd, 1H, J=8, 5 Hz), 7.73 (dd, 1H, J=8, 1.5 Hz), 8.11 (s, 1H), 8.37 (dd, 1H, J=5, 1.5 Hz).

5) Preparation of 3-[4-(3,5-Difluorophenyl)-1-]piperazinyl]-1-[5-methyl-1-(3-methylthio-2-pyridyl)-4-pyrazolyl]-1-trans-propene Hydrochloride The compound obtained in (4) above (759 mg) was reacted and worked up in the same manner as in Example 5-(5) to furnish 540 mg of the title compound.

Melting point: 198–212° C. (decomposition)

$^1$H-NMR (DMSO-d$_6$) δ: 2.22 (s, 3H), 2.43 (s, 3H), 3.0–3.30 (m, 4H), 3.54 (m, 2H), 3.85–4.05 (m, 4H), 6.13 (dt, 1H, J=16, 7 Hz), 6.57 (tm, 1H, J=9 Hz), 6.73 (dm, 2H, J=9 Hz), 6.78 (d, 1H, J=16 Hz), 7.57 (dd, 1H, J=8, 4.5 Hz), 7.96 (s, 1H), 7.90–8.05 (m, 1H), 8.34 (dd, 1H, J=4.5, 1.5 Hz), 10.62 (brs, 1H).

EXAMPLE 27

Synthesis of 3-[4-(3,5-Difluorophenyl)-1-piperazinyl]-1- [5-methyl-1-(3-methylsulfonyl-2-pyridyl)-4-pyrazolyl]-1-trans-propene Hydrochloride

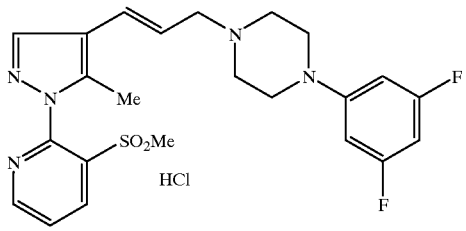

To a solution of 385 mg of the compound obtained in Example 26-(5) in a mixed solvent of 10 ml of water and 20 ml of methanol was added 405 mg of sodium periodate, followed by stirring at room temperature for 65 hours. Chloroform was added thereto, and the mixture was washed with water. The aqueous layer was extracted with a 9:1 (by volume) mixture of chloroform and methanol three times. The combined organic layer was washed with a saturated sodium chloride aqueous solution and dried over anhydrous sodium sulfate. The solvent was removed by evaporation, and the residue was subjected to silica gel column chromatography using a 13:1 (by volume) mixture of chloroform and methanol as a developing solution. The fraction containing the desired compound was concentrated. A 1N hydrochloric acid/ethanol solution was added to the residue, followed by concentration. Recrystallization of the residue from ethyl acetate-ethanol yielded 154 mg of the title compound.

Melting point: 139–144° C. (decomposition)

$^1$H-NMR (DMSO-d$_6$) δ: 2.58 (s, 3H), 2.84 (s, 3H), 3.35–3.50 (m, 2H), 3.79 (m, 4H), 3.90–4.00 (m, 2H), 4.57 (dm, 2H, J=7 Hz), 6.34 (dt, 1H, J=16, 8 Hz), 6.60 (tt, 1H, J=9, 2 Hz), 6.77 (dd, 2H, J=11, 2 Hz), 6.92 (d, 1H, J=16 Hz), 7.76 (dd, 1H, J=8, 5 Hz), 8.20 (s, 1H), 8.56 (dd, 1H, J=8, 1.5 Hz), 8.68 (dd, 1H, J=5, 1.5 Hz), 12.57 (brs, 1H).

EXAMPLE 28

Synthesis of 1-[1-(3-Chloro-4-pyridyl)-5-methyl-4-pyrazolyl]-3-[4-(3,5-difluorophenyl)-1-piperazinyl]-1-trans-propene Hydrochloride

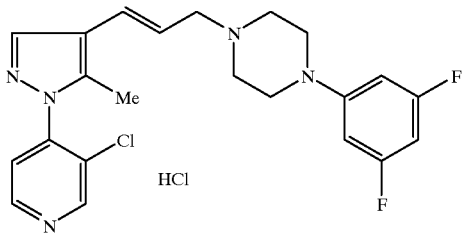

1) Preparation of 3-Chloro-4-iodopyridine

To 76 ml of an anhydrous THF solution of 10 ml of diisopropylamine was added 48.6 ml (1.57 M hexane solution) of n-butyllithium at −78° C., and the mixture was stirred at that temperature for 30 minutes. To the reaction mixture was added 10 ml of a THF solution of 8.66 g of 3-chloropyridine, followed by stirring at −78° C. for 30 minutes. To the reaction mixture was further added 30 ml of a THF solution of 19.4 g of iodine, followed by stirring at the same temperature for 30 minutes. The temperature was raised to 0° C., at which the mixture was stirred for 2.5 hours. The reaction mixture was poured into 300 ml of a 8% sodium sulfite aqueous solution and extracted with diethyl ether. The organic layer was washed successively with a 10% sodium hydrogencarbonate aqueous solution, water, and a saturated sodium chloride aqueous solution and dried. The solvent was evaporated, and the residue was subjected to silica gel column chromatography using a mixture of ethyl acetate and hexane (1:9 by volume) as a developing solution. The fraction containing the desired compound was concentrated to give 4.54 g of the title compound.

$^1$H-NMR (CDCl$_3$) δ: 7.80 (d, 1H, J=5 Hz), 8.07 (d, 1H, J=5 Hz), 8.56 (s, 1H).

2) Preparation of 4-Acetyl-1-(3-iodo-4-pyridyl)-5-methylpyrazole

To 20 ml of a butanol solution of 4.54 g of the compound obtained in (1) above were added 2.93 ml of hydrazine monohydrate and 2.78 g of potassium carbonate, followed by heating under reflux for 9 hours. After cooling, the reaction mixture was poured into 100 ml of water and extracted with chloroform four times. The organic layer was washed with a saturated sodium chloride aqueous solution and dried. The solvent was removed by evaporation, and the resulting residue was subjected to silica gel column chromatography using a mixture of 2 to 5% methanol and chloroform as a developing solution. The resulting colorless solid weighing 1.58 g was added to 10 ml of a solution of 2.07 g of ethoxymethyleneacetylalcetone in 13.2 ml of ethanol, and the mixture was stirred at room temperature for 30 minutes and at 60° C. for 2 hours. After cooling, the solvent was removed by evaporation, and the residue was recrystallized from diethyl ether/hexane to give 1.93 g of the title compound.

$^1$H-NMR (CDCl$_3$) δ: 2.47 (s, 3H), 2.52 (s, 3H), 7.37 (d, 1H, J=5 Hz), 8.08 (s, 1H), 8.70 (d, 1H, J=5 Hz), 8.84 (s, 1H).

3) Preparation of 1-[1-(3-Chloro-4-pyridyl)-5-methyl-4-pyrazolyl]-3-[4-(3,5-difluorophenyl)-1-piperazinyl]-1-propanone The compound obtained in (2) (783 mg), 1-(3,5-difluorophenyl)piperazine hydrochloride (500 mg), and p-formaldehyde (665 mg) were reacted, and the product was worked up in the same manner as in Example 6-(1) to obtain 759 mg of the title compound.

$^1$H-NMR (CDCl$_3$) δ: 2.47 (s, 3H), 2.67 (t, 4H, J=5 Hz), 2.90 (t, 2H, J=7 Hz), 3.09 (t, 2H, J=7 Hz), 3.22 (t, 4H, J=5 Hz), 6.25 (tt, 1H, J=2, 9 Hz), 6.36 (dd, 2H, J=2, 9 Hz), 7.37 (d, 1H, J=5 Hz), 8.13 (s, 1H), 8.70 (d, 1H, J=5 Hz), 8.84 (s, 1H).

4) Preparation of 1-[1-(3-Chloro-4-pyridyl)-5-methyl-4-pyrazolyl]-3-[4-(3,5-difluorophenyl)-1-piperazinyl]-1-trans-propene Hydrochloride The compound obtained in (3) (358 mg) was reacted and worked up in the same manner as in Example 5-(5) to afford 192 mg of the title compound.

Melting point: 120–124° C. (decomposition)

$^1$H-NMR (DMSO-d$_6$) δ: 2.21 (s, 3H), 3.05–3.15 (m, 2H), 3.20–3.30 (m, 2H), 3.50–3.55 (m, 2H), 3.90–4.00 (m, 4H), 6.18 (dt, 1H, J=16, 7 Hz), 6.57 (t, 1H, J=9 Hz), 6.73 (d, 2H, J=9 Hz), 6.79 (d, 1H, J=16 Hz), 7.66 (d, 1H, J=5 Hz), 8.05 (s, 1H), 8.75 (d, 1H, J=5 Hz), 8.93 (s, 1H), 11.19 (br, 1H).

EXAMPLE 29

Synthesis of 1-[1-(3,5-Dichloro-4-pyridyl)-5-methyl-4-pyrazolyl]-3-[4-(3,5-difluorophenyl)-1-piperazinyl]-1-trans-propene Hydrochloride

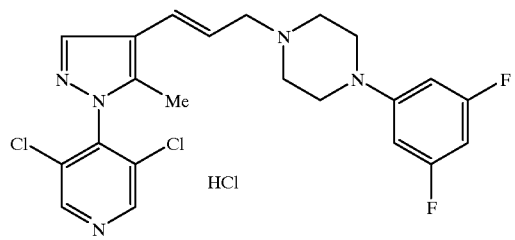

1) Preparation of 3,5-Dichloro-4-hydrazinopyridine

The procedure of Example 12-(1) was repeated, except for replacing 2-chloro-3-methoxypyridine with 5.0 g of 3,4,5-trichloropyridine, to give 2.85 g of the title compound.

$^1$H-NMR (CDCl$_3$) δ: 4.16 (brs, 2H), 6.09 (brs, 1H), 8.23 (s, 2H).

2) Preparation of 4-Acetyl-1-(3,5-dichloro-4-pyridyl)-5-methylpyrazole

The procedure of Example 5-(2) was repeated, except for replacing 3-chloro-2-hydrazinopyridine with 2.85 g of the compound obtained in (1) above, to yield 1.21 g of the title compound.

$^1$H-NMR (CDCl$_3$) δ: 2.41 (s, 3H), 2.53 (s, 3H), 8.14 (s, 1H), 8.73 (s, 2H).

3) Preparation of 1-[1-(3,5-Dichloro-4-pyridyl)-5-methyl-4-pyrazolyl]-3-[4-(3,5-difluorophenyl)-1-piperazinyl]-1-propanone Hydrochloride The compound obtained in (2) above (540 mg), 468 mg of 1-(3,5-difluorophenyl)piperazine hydrochloride, and 2.4 g of p-formaldehyde were reacted, and the product was worked up in the same manner as in Example 3-(1) to afford 247 mg of the title compound.

Melting point: 183–187° C. (decomposition)

¹H-NMR (CDCl₃) δ: 2.37 (s, 3H), 3.20 (m, 4H), 3.45–3.60 (m, 4H), 3.64 (m, 2H), 3.98 (m, 2H), 6.56 (tm, 1H, J=9 Hz), 6.75 (dm, 2H, J=10 Hz), 8.51 (s, 1H), 8.99 (s, 2H), 10.58 (brs, 1H).

4) Preparation of 1-[1-(3,5-Dichloro-4-pyridyl)-5-methyl-4-pyrazolyl]-3-[4-(3,5-difluorophenyl)-1-piperazinyl]-1-trans-propene Hydrochloride The compound obtained in (3) (235 mg) was reacted and worked up in the same manner as in Example 5-(5) to furnish 80 mg of the title compound.

Melting point: 195–207° C. (decomposition)

¹H-NMR (DMSO-d₆) δ: 2.15 (s, 3H), 3.05–3.25 (m, 4H), 3.50–3.60 (m, 2H), 3.85–4.05 (m, 4H), 6.18 (dt, 1H, J=16, 7 Hz), 6.56 (tm, 1H, J=9 Hz), 6.72 (dm, 2H, J=9 Hz), 6.79 (brd, 1H, J=16 Hz), 8.12 (s, 1H), 8.95 (s, 2H), 10.56 (brs, 1H).

EXAMPLE 30

Synthesis of 3-[4-(3,5-Difluorophenyl)-1-piperazinyl]-1-[5-methyl-1-(2-methylphenyl)-4-pyrazolyl]-1-trans-propene Hydrochloride

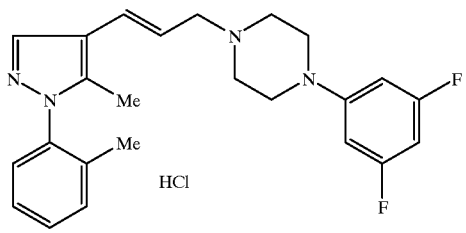

1) Preparation of 3-[4-(3,5-Difluorophenyl)-1-piperazinyl]-1-[5-methyl-1-(2-methylphenyl)-4-pyrazolyl]-1-propanone 4-Acetyl-5-methyl-1-(2-methylphenyl)pyrazole (712 mg), 1-(3,5-difluorophenyl)piperazine hydrochloride (500 mg), and p-formaldehyde (665 mg) were reacted, and the product was worked up in the same manner as in Example 6-(1) to afford 447 mg of the title compound.

¹H-NMR (CDCl₃) δ: 2.03 (s, 3H), 2.38 (s, 3H), 2.66 (t, 4H, J=5 Hz), 2.89 (t, 2H, J=7 Hz), 3.08 (t, 2H, J=7 Hz), 3.22 (t, 4H, J=5 Hz), 6.25 (tt, 1H, J=2, 9 Hz), 6.37 (dd, 2H, J=2, 10 Hz), 7.20 (d, 1H, J=7 Hz), 7.33 (t, 1H, J=7 Hz), 7.36 (d, 1H, J=7 Hz), 7.41 (t, 1H, J=7 Hz), 8.06 (s, 1H).

2) Preparation of 3-[4-(3,5-Difluorophenyl)-1-piperazinyl]-1-[5-methyl-1-(2-methylphenyl)-4-pyrazolyl]-1-trans-propene Hydrochloride The compound obtained in (1) above (440 mg) was reacted and worked up in the same manner as in Example 5-(5) to give 352 mg of the title compound.

Melting point: 112–116° C. (decomposition)

¹H-NMR (DMSO-d₆) δ: 1.98 (s, 3H), 2.10 (s, 3H), 3.05–3.15 (m, 2H), 3.20–3.30 (m, 2H), 3.45–3.55 (m, 2H), 3.85–4.00 (m, 4H), 6.12 (dt, 1H, J=16, 7 Hz), 6.56 (tt, 1H, J=2, 9 Hz), 6.72 (dd, 2H, J=2, 11 Hz), 6.77 (d, 1H, J=16 Hz), 7.27 (d, 1H, J=8 Hz), 7.30–7.50 (m, 3H), 7.90 (s, 1H), 11.30 (br, 1H).

EXAMPLE 31

Synthesis of 3-[4-(3,5-Difluorophenyl)-1-piperazinyl]-1-[1-(3-methoxy-2-pyrazinyl)-5-methyl-4-pyrazolyl]-1-trans-propene Hydrochloride

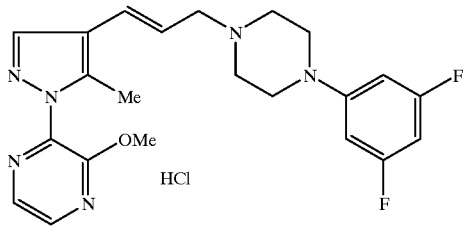

1) Preparation of 2-Iodo-3-methoxypyrazine

To 20 ml of an anhydrous THF solution of 1.3 g of diisopropylamine was added 4.8 ml (2.5 M hexane solution) of n-butyllithium at −78° C., and the mixture was stirred at that temperature for 20 minutes. To the reaction mixture was added 10 ml of a THF solution of 1.1 of 2-methoxypyrazine, followed by stirring at −78° C. for 1 hour. To the reaction mixture was further added 10 ml of a THF solution of 4.0 g of iodine, followed by stirring for 4 hours while gradually elevating the temperature to room temperature. The reaction mixture was diluted with ethyl acetate, washed successively with a saturated sodium thiosulfate aqueous solution and a saturated sodium chloride aqueous solution, and dried over anhydrous sodium sulfate. The solvent was evaporated, and the residue was subjected to silica gel column chromatography using chloroform as a developing solution. The fraction containing the desired compound was concentrated to give 0.49 g of the title compound.

¹H-NMR (CDCl₃) δ: 4.02 (s, 3H), 7.94 (d, 1H, J=2.5 Hz), 7.99 (d, 1H, J=2.5 Hz).

2) Preparation of 2-Hydrazino-3-methoxypyrazine

To 10 ml of a THF solution of 0.49 g of the compound obtained in (1) above was added 0.5 g of hydrazine monohydrate, followed by heating under reflux for 3 days. The reaction mixture was diluted with chloroform, washed with a saturated sodium chloride aqueous solution, and dried over anhydrous sodium sulfate. The solvent was evaporated off to yield 0.3 g of the title compound.

¹H-NMR (CDCl₃) δ: 3.8–3.6 (m, 2H), 3.98 (s, 3H), 6.20 (bs, 1H), 7.39 (d, 1H, J=3.4 Hz), 7.63 (d, 1H, J=3.4 Hz).

3) Preparation of 4-Acetyl-1-(3-methoxy-2-pyrazinyl)-5-methylpyrazole

The procedure of Example 5-(2) was repeated, except for replacing 3-chloro-2-hydrazinopyridine with 300 mg of the compound obtained in (2) above, to yield 350 mg of the title compound.

¹H-NMR (CDCl₃) δ: 2.51 (s, 6H), 4.01 (s, 3H), 8.08 (s, 1H), 8.19 (d, 1H, J=2.9 Hz), 8.30 (d, 1H, J=2.9 Hz).

4) Preparation of 3-[4-(3,5-Difluorophenyl)-1-piperazinyl]-1-[1-(3-methoxy-2-pyrazinyl)-5-methyl-4-pyrazolyl]-1-propanone The compound obtained in (3) (350 mg), 1-(3,5-difluorophenyl)piperazine hydrochloride (350 mg), and p-formaldehyde (1.2 g) were reacted, and the product was worked up in the same manner as in Example 6-(1) to afford 340 mg of the title compound.

$^1$H-NMR (CDCl$_3$) δ: 2.52 (s, 3H), 2.65 (t, 4H, J=5.3 Hz), 2.88 (t, 2H, J=7.3 Hz), 3.08 (t, 2H, J=7.3 Hz), 3.21 (t, 4H, J=5.3 Hz), 4.04 (s, 3H), 6.25 (tt, 1H, J=10.7, 2.5 Hz), 6.36 (dd, 1H, J=10.7, 2.5 Hz), 8.13 (s, 1H), 8.19 (d, 1H, J=2.5 Hz), 8.30 (d, 1H, J=2.5 Hz).

5) Preparation of 3-[4-(3,5-Difluorophenyl)-1-piperazinyl]-1-[1-(3-methoxy-2-pyrazinyl)-5-methyl-4-pyrazolyl]-1-trans-propene Hydrochloride The compound obtained in (4) above (340 mg) was reacted and worked up in the same manner as in Example 5-(5) to give 250 mg of the title compound.

Melting point: 198–205° C. (decomposition)

$^1$H-NMR (DMSO-d$_6$) δ: 2.22 (s, 3H), 3.1–3.2 (m, 2H), 3.2–3.3 (m, 2H), 3.4–3.6 (m, 4H), 3.8–3.9 (m, 2H), 3.95 (s, 3H), 6.15 (dt, 1H, J=15.6, 7.3 Hz), 6.5–6.6 (m, 1H), 6.7–6.8 (m, 2H), 7.99 (s, 1H), 8.28 (d, 1H, J=3.0 Hz), 8.45 (d, 1H, J=3.0 Hz).

EXAMPLE 32

Synthesis of 3-[4-(3,5-Difluorophenyl)-1-piperazinyl]-1-[1-(6-methoxy-2-pyrazinyl)-5-methyl-4-pyrazolyl]-1-trans-propene Hydrochloride

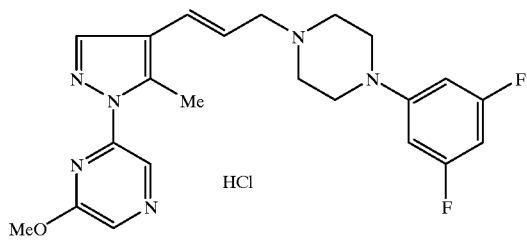

1) Preparation of 2-Hydrazino-6-methoxypyrazine

To 20 ml of methanol was added 3.3 g of sodium t-butoxide, followed by stirring at room temperature for 1 hour. The mixture was cooled to 0° C., and 5.0 g of 2,6-dichloropyrimidine was added thereto, and the mixture was stirred for 18 hours while slowly warming to room temperature. The reaction mixture was diluted with chloroform, washed with a saturated sodium chloride aqueous solution, and dried over anhydrous sodium sulfate. The solvent was evaporated, and the residue was dissolved in 20 ml of ethanol. The solution was added to 20 ml of an ethanolic solution of 15 g of hydrazine monohydrate, and 5.0 g of potassium carbonate was added thereto, followed by heat-refluxing for 24 hours. Water was added to the reaction mixture, and the mixture was extracted with chloroform. The organic layer was dried over anhydrous sodium sulfate, and the solvent was removed by evaporation. Recrystallization of the residue from chloroform-hexane yielded 1.8 g of the title compound.

$^1$H-NMR (CDCl$_3$) δ: 3.8–3.6 (m, 2H), 3.98 (s, 3H), (6.20 (brs, 1H), 7.42 (s, 1H), 8.29 (s, 1H).

2) Preparation of 4-Acetyl-1-(6-methoxy-2-pyrazinyl)-5-methylpyrazole

The procedure of Example 5-(2) was repeated, except for replacing 3-chloro-2-hydrazinopyridine with 1.5 g of the compound obtained in (1) above, to give 2.3 g of the title compound.

$^1$H-NMR (CDCl$_3$) δ: 2.51 (s, 3H), 2.97 (s, 3H), 4.01 (s, 3H), 8.04 (s, 1H), 8.25 (s, 1H), 8.73 (s, 1H).

3) Preparation of 3-[4-(3,5-Difluorophenyl)-1-piperazinyl]-1-[1-(6-methoxy-2-pyrazinyl)-5-methyl-4-pyrazolyl]-1-propanone The compound obtained in (2) (2.3 g), 1-(3,5-difluorophenyl)piperazine hydrochloride (2.4 g), and p-formaldehyde (10 g) were reacted, and the reaction mixture was worked up in the same manner as in Example 6-(1) to give 1.3 g of the title compound.

$^1$H-NMR (DMSO-d$_6$) δ: 2.7–2.9 (m, 4H), 2.93 (s, 3H), 3.0–3.2 (m, 6H), 3.5–3.6 (m, 2H), 4.01 (s, 3H), 6.18 (tt, 1H, J=10.3, 2.0 Hz), 6.35 (dd, 1H, J=10.3, 2.0 Hz), 8.00 (s, 1H), 8.06 (s, 1H), 8.28 (s, 1H).

4) Preparation of 3-[4-(3,5-Difluorophenyl)-1-piperazinyl]-1-[1-(6-methoxy-2-pyrazinyl)-5-methyl-4-pyrazolyl]-1-trans-propene Hydrochloride The compound obtained in (3) (1.3 g) was reacted and worked up in the same manner as in Example 5-(5) to yield 650 mg of the title compound.

Melting point: 220–227° C. (decomposition)

$^1$H-NMR (DMSO-d$_6$) δ: 2.6–2.7 (m, 4H), 2.74 (s, 3H), 3.3–3.4 (m, 6H), 4.00 (s, 3H), 6.09 (dt, 1H, J=16.1, 7.3 Hz), 6.26 (tt, 1H, J=10.3, 2.0 Hz), 6.3–6.5 (m, 3H), 8.23 (s, 1H), 8.14 (s, 1H), 8.80 (s, 1H).

EXAMPLE 33

Synthesis of 1-[1-(2-Benzyloxy-6-methyl-4-pyrimidinyl)-5-methyl-4-pyrazolyl]-3-[4-(3,5-difluorophenyl)-1-piperazinyl]-1-trans-propene

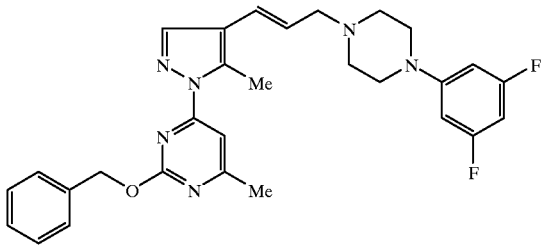

1) Preparation of 4-Acetyl-1-(2-benzyloxy-6-methyl-4-pyrimidinyl)-5-methylpyrazole Sodium t-butoxide (3.5 g) was added to a mixture consisting of 5.0 g of 2,4-dichloro-6-methylpyrimidine, 3.8 ml of benzyl alcohol, and 75 ml of t-butanol, and the mixture was stirred at room temperature for 16 hours. The reaction mixture was poured into ice-water and extracted with chloroform. The organic layer was washed with a saturated sodium chloride aqueous solution and dried over anhydrous sodium sulfate. The solvent was removed by evaporation, and to the residue were added 40 ml of ethanol and 0.57 ml of water. To the mixture were further added 3.8 g of hydrazine monohydrate and 6.35 g of potassium carbonate, followed by heating under reflux for 2 hours. After cooling to room temperature, the reaction mixture was concentrated, chloroform was added to the residue, and the mixture was washed with water. The aqueous layer was extracted three times with chloroform-methanol (9:1 by volume). The combined organic layer was washed with a saturated sodium chloride aqueous solution and dried over anhydrous sodium sulfate. The solvent was removed by evaporation. To the residue were added 4.8 g of ethoxymethyleneacetylacetone and 75 ml of ethanol. After the mixture was stirred at room temperature for 40 minutes, the liquid temperature was slowly raised up to about 70° C., at which the mixture was stirred until the insoluble matter dissolved. Thereafter, the stirring was continued at about 60° C. for 1 hour. After cooling the reaction mixture to room temperature, the solvent was removed by evaporation, and the residue was subjected to silica gel column chromatography using a 2:1 (by volume) mixture of hexane and ethyl acetate as a developing solution. The fraction containing a low-polar compound was concentrated to give 2.31 g of the title compound. From the fraction containing a high-polar compound was obtained 4.99 g of 4-acetyl-1-(4-benzyloxy-6-methyl-2-pyrimidinyl)-5-methylpyrazole, the main reaction product.

$^1$H-NMR (CDCl$_3$) δ: 2.50 (s, 3H), 2.55 (s, 3H), 3.00 (s, 3H), 5.46 (s, 2H), 7.30–7.50 (m, 6H), 8.01 (s, 1H).

2) Preparation of 1-[1-(2-Benzyloxy-6-methyl-4-pyrimidinyl)-5-methyl-4-pyrazolyl]-3-[4-(3,5-difluorophenyl)-1-piperazinyl]-1-propanone The compound obtained in (1) (3.1 g), 1-(3,5-difluorophenyl)piperazine hydrochloride (2.26 g), and p-formaldehyde (12.2 g) were reacted, and the product was worked up in the same manner as in Example 6-(1) to afford 1.12 g of the title compound.

$^1$H-NMR (CDCl$_3$) δ: 2.55 (s, 3H), 2.60–2.70 (m, 4H), 2.86 (t, 2H, J=7 Hz), 3.01 (s, 3H), 3.05 (t, 2H, J=7 Hz), 3.15–3.25 (m, 4H), 5.46 (s, 2H), 6.25 (tt, 1H, J=9, 2 Hz), 6.35 (dm, 2H, J=10 Hz), 7.30–7.50 (m, 6H), 8.05 (s, 1H).

3) Preparation of 1-[1-(2-Benzyloxy-6-methyl-4-pyrimidinyl)-5-methyl-4-pyrazolyl]-3-[4-(3,5-difluorophenyl)-1-piperazinyl]-1-trans-propene The compound obtained in (2) above (1.1 g) was reacted in the same manner as in Example 1-(2), and the reaction mixture was concentrated. Chloroform was added to the concentrate, and the mixture was washed successively with a saturated sodium hydrogencarbonate aqueous solution and a saturated sodium chloride aqueous solution, and dried over anhydrous sodium sulfate. The solvent was evaporated, and the residue was subjected to silica gel column chromatography using a 99:1 (by volume) mixture of chloroform and methanol as a developing solution. The fraction containing the desired compound was concentrated to yield 476 mg of the title compound.

$^1$H-NMR (CDCl$_3$) δ: 2.51 (s, 3H), 2.60–2.65 (m, 4H), 2.71 (s, 3H), 3.15–3.25 (m, 6H), 5.45 (s, 2H), 6.09 (dt, 1H, J=16, 7 Hz), 6.25 (tt, 1H, J=9, 2 Hz), 6.37 (dd, 2H, J=11, 2 Hz), 6.39 (d, 1H, J=16 Hz), 7.30–7.50 (m, 6H), 7.81 (s, 1H).

EXAMPLE 34

Synthesis of 3-[4-(3,5-Difluorophenyl)-1-piperazinyl]-1-[1-(2-hydroxy-6-methyl-4-pyrimidinyl)-5-methyl-4-pyrazolyl]-1-trans-propene

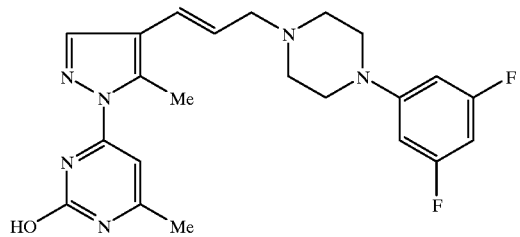

To 475 mg of the compound obtained in Example 33-(3) were added 3 ml of trifluoroacetic acid and 0.12 ml of thioanisole, followed by heating at 50° C. for 2.5 hours while stirring. The reaction mixture was concentrated, a saturated sodium hydrogencarbonate aqueous solution was added to the concentrate, and the mixture was extracted with chloroform three times. The combined organic layer was washed with a saturated sodium chloride aqueous solution and dried over anhydrous sodium sulfate. The solvent was evaporated off, and the residue was subjected to silica gel column chromatography using a 39:1 (by volume) mixture of chloroform and methanol as a developing solution. The fraction containing the desired compound was concentrated to give 193 mg of the title compound.

$^1$H-NMR (CDCl$_3$) δ: 2.45 (s, 3H), 2.60–2.65 (m, 4H), 2.81 (s, 3H), 3.20 (dm, 2H, J=7 Hz), 3.20–3.25 (m, 4H), 6.10 (dt, 1H, J=16, 7 Hz), 6.26 (tm, 1H, J=9 Hz), 6.35–6.40 (m, 2H), 6.40 (d, 1H, J=16 Hz), 7.08 (s, 1H), 7.84 (s, 1H).

EXAMPLE 35

Synthesis of 1-[1-(2-Chloro-6-methyl-4-pyrimidinyl)-5-methyl-4-pyrazolyl]-3-[4-(3,5-Difluorophenyl)-1-piperazinyl]-1-trans-propene

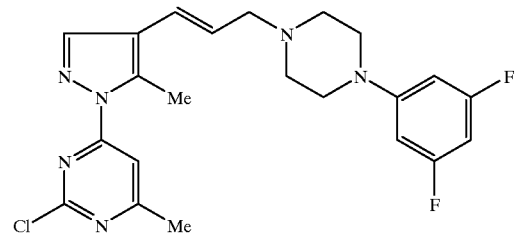

To 250 mg of the compound obtained in Example 34 was added 5 ml of phosphorus oxychloride. The mixture was stirred at 60° C. for 2.5 hours, followed by concentration. A mixture of the concentrate and water was neutralized with sodium hydrogencarbonate and extracted with chloroform three times. The combined organic layer was washed with a saturated sodium chloride aqueous solution and dried over anhydrous sodium sulfate. The solvent was evaporated, and the residue was subjected to silica gel column chromatography using chloroform was a developing solution. Concentration of the fraction containing the desired compound gave 180 mg of the title compound.

$^1$H-NMR (CDCl$_3$) δ: 2.56 (s, 3H), 2.60–2.65 (m, 4H), 2.75 (s, 3H), 3.15–3.25 (m, 6H), 6.11 (dt, 1H, J=16, 7 Hz), 6.26 (tt, 1H, J=9, 2 Hz), 6.35–6.45 (m, 3H), 7.73 (s, 1H), 7.84 (s, 1H).

EXAMPLE 36

Synthesis of 3-[4-(3,5-Difluorophenyl)-1-piperazinyl]-[1-[2-(2-methoxybenzylamino)-6-methyl-4-pyrimidinyl]-5-methyl-4-pyrazolyl]-1-trans-propene

EXAMPLE 37

Synthesis of 1-[1-(2-amino-6-methyl-4-pyrimidinyl)-5-methyl-4-pyrazolyl]-3-[4-(3,5-difluorophenyl)-1-piperazinyl]-1-trans-propene Hydrochloride

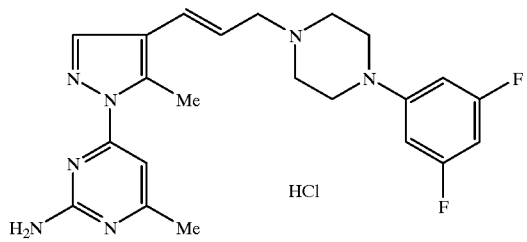

To 212 mg of the compound obtained in Example 36 were added 5 ml of trifluoroacetic acid and 50 μl of anisole, followed by heating under reflux for 4 hours. The reaction mixture was concentrated, chloroform was added to the concentrate, and the mixture was washed successively with a saturated sodium hydrogencarbonate aqueous solution and a saturate sodium chloride aqueous solution and dried over anhydrous sodium sulfate. The solvent was evaporated off, and the residue was subjected to silica gel column chromatography using a 66:1 (by volume) mixture of chloroform and methanol as a developing solution. The fraction containing the desired compound was concentrated, and 2 ml of a 1N hydrochloric acid/ethanol solution to the residue, followed by concentration. Recrystallization from ethanol afforded 134 mg of the title compound.

Melting point: 210–217° C. (decomposition)

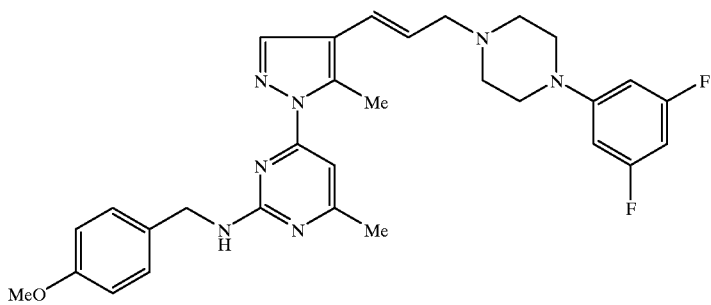

To 15 ml of a THF solution of 155 mg of the compound obtained in Example 35 were added 240 mg of p-methoxybenzylamine and 50 mg (0.362 mmol) of potassium carbonate, followed by refluxing for 60 hours. Chloroform was added to the reaction mixture, and the mixture was washed with a saturated sodium chloride aqueous solution. The combined organic layer was dried over anhydrous sodium sulfate, and the solvent was evaporated. The residue was subjected to silica gel column chromatography using a 99:1 mixture (by volume) of chloroform and methanol as a developing solution. The fraction containing the desired compound was concentrated to give 183 mg of the title compound.

$^1$H-NMR (CDCl$_3$) δ: 2.39 (s, 3H), 2.55–2.70 (m, 7H), 3.18 (d, 2H, J=7 Hz), 3.20–3.25 (m, 4H), 3.80 (s, 3H), 4.58 (d, 2H, J=6 Hz), 5.39 (br, 1H), 6.05 (dt, 1H, J=16, 7 Hz), 6.25 (tt, 1H, J=9, 2 Hz), 6.30–6.40 (m, 3H), 6.87 (d, 2H, J=9 Hz), 7.07 (s, 1H), 7.20–7.30 (m, 2H), 7.78 (s, 1H).

$^1$H-NMR (DMSO-d$_6$) δ: 2.30 (s, 3H), 2.72 (s, 3H), 3.05–3.25 (m, 4H), 3.50–3.60 (m, 2H), 3.90–4.00 (m, 4H), 6.20 (dt, 1H, J=16, 7 Hz), 6.56 (tm, 1H, J=9 Hz), 6.72 (dm, 2H, J=9 Hz), 6.80 (d, 1H, J=16 Hz), 6.92 (s, 1H), 8.06 (s, 1H), 10.74 (br, 1H).

EXAMPLE 38

Synthesis of 3-[4-(3,5-Difluorophenyl-1-piperazinyl]-1-[1-[2-(4-methoxybenzylamino)-4-pyrimidinyl]-5-methyl-4-pyrazolyl]-1-trans-propene

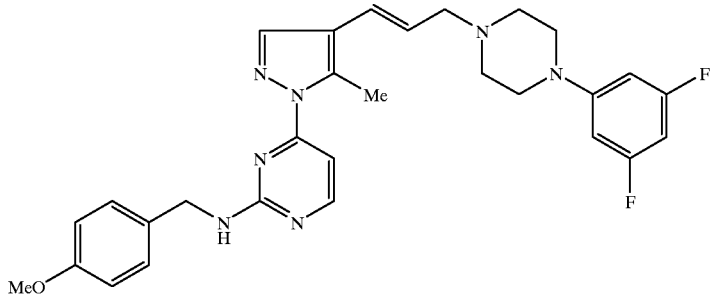

1) Preparation of Ethyl 1-(2-Benzyloxy-4-pyrimidinyl)-5-methyl-4-pyrazolecarboxylate Sodium t-butoxide (24.5 g) was added to a mixture consisting of 25 g of 2,4-dichloropyrimidine, 20 g of benzyl alcohol, and 300 ml of t-butanol, and the mixture was stirred at room temperature for 24 hours. The reaction mixture was poured into ice-water and extracted with chloroform. The organic layer was washed with a saturated sodium chloride aqueous solution and dried over anhydrous sodium sulfate. The solvent was removed by evaporation. To the residue was added 200 ml of ethanol. To the mixture were further added 40 g of hydrazine monohydrate and 25 g of potassium carbonate, followed by heating under reflux for 24 hours. After cooling to room temperature, the reaction mixture was concentrated, chloroform was added to the residue, and the mixture was washed with water. The aqueous layer was extracted three times with chloroform-methanol (9:1 by volume). The combined organic layer was washed with a saturated sodium chloride aqueous solution and dried over anhydrous sodium sulfate. The solvent was removed by evaporation. To the residue were added 200 ml of ethanol and then 100 ml of an ethanolic solution of 48.5 g of ethyl ethoxymethyleneacetoacetate. The mixture was stirred at room temperature for 1 hour and then refluxed for 5 hours. After cooling to room temperature, the solvent was removed by evaporation, and the residue was subjected to silica gel column chromatography using a 2:1 (by volume) mixture of hexane and ethyl acetate as a developing solvent. The fraction containing a low-polar compound was concentrated to give 9.4 g of the title compound. Prom the fraction containing a high-polar compound was obtained 40.5 g of 1-4-benzyloxy-2-pyrimidinyl)-4-ethoxycarbonyl-5-methylpyrazole, the main reaction product.

$^1$H-NMR (CDCl$_3$) δ: 1.38 (t, 3H, J=7 Hz), 3.04 (s, 3H), 4.33 (q, 2H, J=7 Hz), 5.48 (s, 2H), 7.3–7.5 (m, 5H), 7.60 (d, 3H, J=5 Hz), 8.04 (s, 1H), 8.60 (d, 1H, J=5 Hz).

2) Preparation of Ethyl 1-(2-Hydroxy-4-pyrimidinyl)-5-methyl-4-pyrazolecarboxylate A mixture consisting of 6.18 g of the compound obtained in (1) above, 4.3 ml of thioanisole, and 60 ml of trifluoroacetic acid was stirred at room temperature for 15 hours. The trifluoroacetic acid was removed by evaporation, and 100 ml of ethyl ether was added to the residue. The mixture was stirred at room temperature for 2 hours, and the precipitate was collected by filtration to obtain 4.27 g of the title compound.

$^1$H-NMR (CDCl$_3$) δ: 1.38 (t, 3H, J=7 Hz), 3.10 (s, 3H), 4.34 (q, 2H, J=7 Hz), 7.20 (d, 1H, J=7 Hz), 7.77 (d, 1H, J=7 Hz), 8.06 (s, 1H).

3) Preparation of Ethyl 1-(2-Chloro-4-pyrimidinyl)-5-methyl-4-pyrazolecarboxylate To 4.27 g of the compound obtained in (2) above was added 30 ml of phosphorus oxychloride, followed by heating under reflux for 4.5 hours. After cooling to room temperature, the reaction mixture was slowly poured into ice-water. The resulting suspension was stirred at room temperature for 30 minutes, and any insoluble matter was collected by filtration to yield 4.29 g of the title compound.

$^1$H-NMR (CDCl$_3$) δ: 1.39 (t, 3H, J=7 Hz), 3.09 (s, 3H), 4.35 (q, 2H, J=7 Hz), 7.93 (d, 1H, J=5 Hz), 8.08 (s, 1H), 8.66 (d, 1H, J=5 Hz).

4) Preparation of Ethyl 1-[2-(4-Methoxybenzylamino)-4-pyrimidinyl]-5-methyl-4-pyrazolecarboxylate A mixture consisting of 2.21 g of the compound obtained in (3), 2.2 ml of 4-methoxybenzylamine, 1.15 g of potassium carbonate, and 50 ml of THF was heat-refluxed for 14 hours. After cooling the reaction mixture to room temperature, 100 ml of grater was added thereto, followed by stirring for 2 hours. The precipitate was collected by filtration to yield 3.01 g of the title compound.

$^1$H-NMR (CDCl$_3$) δ: 1.37 (t, 3H, J=7 Hz), 2.95 (s, 3H), 3.80 (s, 3H), 4.32 (q, 2H, J=7 Hz), 4.59 (d, 2H, J=6 Hz), 5.55 (br, 1H), 6.88 (d, 2H, J=8 Hz), 7.18 (d, 1H, J=5 Hz), 7.27 (d, 2H, J=8 Hz), 8.01 (s, 1H), 8.37 (brd, 1H, J=5 Hz).

5) preparation of 1-[2-(4-Methoxybenzylamino)-4-pyrimidinyl]-5-methyl-4-pyrazolecarbaldehyde A methylene chloride solution (80 ml) containing 2.99 g of the compound obtained in (4) was cooled to −78° C. in a nitrogen atmosphere, and 32 ml of diisobutylaluminum hydride (1M hexane solution) was added thereto over 30 minutes, followed by stirring at the same temperature for 4 hours. A potassium tartrate aqueous solution was added to the reaction mixture, and the mixture was stirred at room temperature for 3 hours. Any insoluble matter was removed by filtration, and the filtrate was washed successively with water and a saturated sodium chloride aqueous solution. The organic layer was dried, and the solvent was removed by Evaporation. To the residue were added 50 ml of dioxane and 6.37 g of activated manganese dioxide, and the mixture was stirred at room temperature for 24 hours. The insoluble matter was removed by filtration through Celite, and the filtrate was concentrated. The concentrate was subjected to silica gel column chromatography using a 1:9 (by volume) mixture of ethyl acetate and chloroform as a developing solvent. The fraction containing the desired compound was concentrated to give 1.87 g of the title compound.

$^1$H-NMR (CDCl$_3$) δ: 3.10 (s, 3H), 3.81 (s, 3H), 4.59 (d, 2H, J=6 Hz), 5.79 (br, 1H), 6.89 (d, 2H, J=8 Hz), 7.21 (d, 1H, J=5 Hz), 7.27 (d, 2H, J=8 Hz), 8.05 (s, 1H), 8.36 (brd, 1H, J=5 Hz), 9.99 (s, 1H).

6) Preparation of Ethyl (E)-3-[1-[2-(4-Methoxybenzylamino)-4-pyrimidinyl]-5-methyl-4-pyrazolyl]-2-propenoate A mixture of 1.62 g of the compound obtained in (5), 2.09 g of (carboethoxymethylene)triphenylphospholane, and 50 ml of toluene was stirred at 80° C. for 15 hours and then at room temperature for 5 hours. The precipitate was collected by filtration to yield 1.78 g of the title compound.

$^1$H-NMR (CDCl$_3$) δ: 1.33 (t, 3H, J=7 Hz), 2.72 (s, 3H), 3.81 (s, 3H), 4.25 (q, 2H, J=7 Hz), 4.58 (d, 2H, J=6 Hz), 5.55 (br, 1H), 6.25 (d, 1H, J=16 Hz), 6.88 (d, 2H, J=8 Hz), 7.18 (d, 1H, J=6 Hz), 7.27 (d, 2H, J=8 Hz), 7.58 (d, 1H, J=16 Hz), 7.88 (s, 1H), 8.34 (d, 1H, J=6 Hz).

7) Preparation of (E)-3-[1-[2-(4-Methoxybenzylamino)-4-pyrimidinyl]-5-methyl-4-pyrazolyl]-2-propenal A methylene chloride solution (32 ml) containing 1.25 g of the compound obtained in (6) was cooled to −78° C. in a nitrogen atmosphere, and 12.7 ml of diisobutylaluminum hydride (1M hexane solution) was added thereto over 30 minutes, followed by stirring at the same temperature for 4 hours. A potassium tartrate aqueous solution was added to the reaction mixture, and the mixture was stirred at room temperature for 2 hours. Any insoluble matter was removed by filtration, and the filtrate was washed successively with water and a saturated sodium chloride aqueous solution. The organic layer was dried, and the solvent was removed by evaporation. To the residue were added 50 ml of dioxane and 2.76 g of activated manganese dioxide, and the mixture was stirred at room temperature for 24 hours. The insoluble matter was removed by filtration through Celite, and the filtrate was concentrated. Diethyl ether was added to the concentrate, and the precipitate was collected by filtration to give 799 mg of the title compound.

$^1$H-NMR (CDCl$_3$) δ: 2.75 (s, 3H), 3.81 (s, 3H), 4.59 (d, 2H, J=6 Hz), 5.53 (br, 1H), 6.54 (dd, 1H, J=8 Hz, 16 Hz), 6.89 (d, 2H, J=8 Hz), 7.21 (d, 1H, J=5 Hz), 7.28 (d, 2H, J=8 Hz), 7.37 (d, 1H, J=16 Hz), 7.91 (s, 1H), 8.37 (d, 1H, J=5 Hz), 9.64 (d, 1H, J=8 Hz).

8) Preparation of 3-[4-(3,5-Difluorophenyl)-1-piperazinyl]-1-[1-[2-(4-methoxybenzylamino)-4-pyrimidinyl]-5-methyl-4-pyrazolyl]-1-trans-propene A mixture consisting of 350 mg of the compound obtained in (7), 280 mg of 1-(3,5-difluorophenyl)piperazine hydrochloride, and 20 ml of ethanol was stirred at room temperature for 1 hour. To the reaction mixture were added 0.45 ml of acetic acid and 200 mg of sodium cyanoborohydride, followed by stirring at room temperature for 1 hour. To the reaction mixture was further added 200 mg of sodium cyanoborohydride, and the stirring was continued at room temperature for an additional 48 hour period. A 1N sodium hydroxide aqueous solution was added to the reaction mixture, and the mixture was extracted with a 9:1 (by volume) mixture of chloroform and methanol. The organic layer was washed with a saturated sodium chloride aqueous solution and dried. The solvent was removed by evaporation. The residue was subjected to silica gel column chromatography using a 29:1 (by volume) mixture of chloroform and methanol as a developing solvent. The fraction containing the desired compound was concentrated to afford 370 mg of the title compound.

$^1$H-NMR (CDCl$_3$) δ: 2.5–2.6 (m, 4H), 2.64 (s ,3H), 3.1–3.3 (m, 6H), 3.80 (s, 3H), 4.58 (d, 2H, J=5.4 Hz), 5.4–5.6 (m, 1H), 6.06 (dt, 1H, J=16, 7 Hz), 6.25 (dt, 1H, J=9, 2 Hz), 6.37 (d, 1H, J=16 Hz), 6.3–6.4 (m, 2H), 6.87 (d, 2H, J=8 Hz), 7.17 (d, 1H, J=5 Hz), 7.27 (d, 2H, J=8 Hz), 7.79 (s, 1H), 8.30 (d, 1H, J=5 Hz).

EXAMPLE 39

Synthesis of 1-[1-(2-Amino-4-pyrimidinyl)-5-methyl-4-pyrazolyl]-3-[4-(3,5-difluorophenyl)-1-piperazinyl]-1-trans-propene Hydrochloride

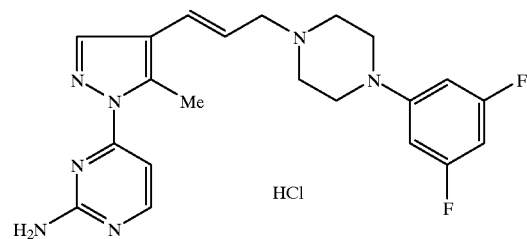

A mixture of 370 mg of the compound obtained in Example 38, 10 ml of trifluoroacetic acid, and 0.23 ml of anisole was treated in the same manner as in Example 37 to give 200 mg of the title compound.

Melting point: 206–209° C. (decomposition)

$^1$H-NMR (DMSO-d$_6$) δ: 2.73 (s, 3H), 3.0–3.2 (m, 4H), 3.5–3.6 (m, 2H), 3.9–4.0 (m, 4H), 6.20 (dt, 1H, J=16, 7 Hz), 6.60 (tt, 1H, J=9, 2 Hz), 6.76 (dd, 2H, J=9, 2 Hz), 6.70 (d, 1H, J=16 Hz), 7.00 (d, 1H, J=5 Hz), 8.10 (s, 1H), 8.30 (d, 1H, J=5 Hz).

EXAMPLE 40

Synthesis of 3-[4-[3-Fluoro-5-(4-methoxybenzyloxy)-phenyl]-1-piperazinyl]-1-[1-[2-(4-methoxybenzylamino)-4-pyrimidinyl]-5-methyl-4-pyrazolyl]-1-trans-propene

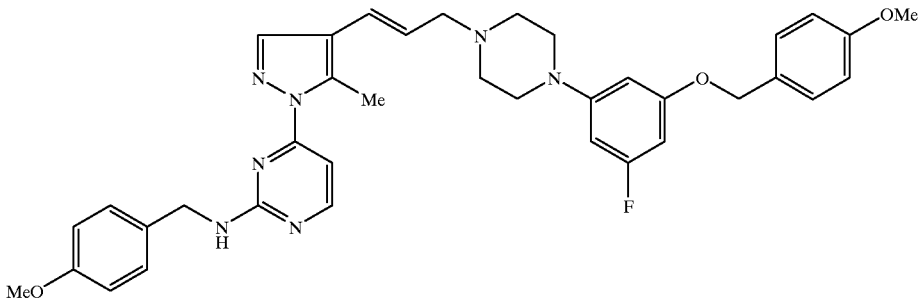

1) Preparation of 1-Bromo-3-fluoro-5-(4-methoxybenzyloxy)-benzene

To a mixture of 2.2 ml of p-methoxybenzyl alcohol and 50 ml of N-methylpyrrolidone was added 840 mg of sodium hydride (60% oil dispersion), and the resulting mixture was stirred at room temperature for 45 minutes in a nitrogen atmosphere. To the reaction mixture was added 2 ml of 1-bromo-3,5-difluorobenzene, followed by stirring at 50° C. for 1.5 hours. The reaction mixture was poured into 50 ml of ice-diluted hydrochloric acid and extracted three times with diethyl ether-hexane (1:1 by volume). The organic layer was washed with a saturated sodium chloride aqueous solution and dried over anhydrous sodium sulfate. The solvent was evaporated, and the residue was purified by silica gel column chromatography using a hexane-ethyl acetate (19:1 by volume) mixed solvent. The fraction containing the desired compound was concentrated to furnish 4.88 g of the title compound.

$^1$H-NMR (CDCl$_3$) δ: 3.82 (s, 2H), 4.95 (s, 2H), 6.62 (dt, 1H, J=10, 2 Hz), 6.85 (dt, 1H, J=8, 2 Hz), 6.90–6.95 (m, 1H), 6.92 (d, 2H, J=8 Hz), 7.33 (d, 2H, J=8 Hz).

2) Preparation of 1-[3-Fluoro-5-(4-methoxybenzyloxy)phenyl]-piperazine

A mixture consisting of 4.88 g of the compound obtained in (1) above, 316 mg of PdCl$_2$[(o-tolyl)$_3$P]$_2$, 2.1 g of sodium t-butoxide, and 80 ml of toluene was heated at 100° C. for 17 hours while stirring in a nitrogen atmosphere. After cooling to room temperature, the reaction mixture was filtered using Celite, and the filtrate was concentrated. The concentrate was purified by silica gel column chromatography using chloroform-methanol (19:1 by volume) as a developing solvent. The fraction containing the desired compound was concentrated to afford 2.30 g of the title compound.

$^1$H-NMR (CDCl$_3$) δ: 3.00 (m, 4H), 3.12 (m, 4H), 3.82 (s, 3H), 4.93 (s, 2H), 6.19 (dt, 1H, J=10, 2 Hz), 6.23 (dt, 1H, J=12, 2 Hz), 6.28 (d, 1H, J=2 Hz), 6.91 (d, 2H, J=9 Hz), 7.34 (d, 2H, J=9 Hz).

3) Preparation of 3-[4-[3-Fluoro-5-(4-methoxybenzyloxy)phenyl]-1-piperazinyl]-1-[1-[2-(4-methoxybenzylamino)-4-pyrimidinyl]-5-methyl-4-pyrazolyl]-1-trans-propene The compound obtained in Example 38-(7) (350 mg) and 1-[3-fluoro-5-(4-methoxybenzyloxy)phenyl]piperazine (380 mg) were reacted and worked up in the same manner as in Example 38-(8) to obtain 580 mg of the title compound.

$^1$H-NMR (CDCl$_3$) δ: 2.5–2.6 (m, 4H), 2.64 (s, 3H), 3.1–3.2 (m, 6H), 3.80 (s, 3H), 3.82 (s, 3H), 4.58 (d, 2H, J=6 Hz), 4.93 (s, 2H), 5.3–5.4 (m, 1H), 6.06 (dt, 1H, J=16, 7 Hz), 6.19 (dt, 1H, J=11, 2 Hz), 6.24 (dt, 1H, J=11, 2 Hz), 6.28 (d, 1H, J=2 Hz), 6.36 (d, 1H, J=16 Hz), 6.88 (d, 2H, J=8 Hz), 6.91 (d, 2H, J=8 Hz), 7.18 (d, 1H, J=5 Hz), 7.27 (d, 2H, J=8 Hz), 7.33 (d, 2H, J=8 Hz), 7.79 (1H, s), 8.31 (d, 1H, J=5 Hz).

EXAMPLE 41

Synthesis of 1-[1-(2-Amino-4-pyrimidinyl)-5-methyl-4-pyrazolyl]-3-[4-(3-fluoro-5-hydroxyphenyl)-1-piperazinyl]-1-trans-propene Hydrochloride

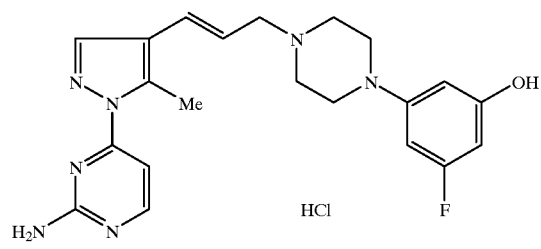

A mixture consisting of 580 mg of the compound obtained in Example 40-(3), 15 ml of trifluoroacetic acid, and 0.24 ml of anisole was treated in the same manner as in Example 37 to give 270 mg of the title compound.

Melting point: 171–179° C. (decomposition)

$^1$H-NMR (DMSO-d$_6$) δ: 2.74 (s, 3H), 3.0–3.2 (m, 4H), 3.5–3.6 (m, 2H), 3.8–3.9 (m, 2H), 3.9–4.0 (m, 2H), 6.06 (d, 1H, J=10 Hz), 6.19 (s, 1H), 6.3–6.4 (m, 2H), 6.83 (d, 1H, J=16 Hz), 7.23 (d, 1H, J=5 Hz), 8.22 (s, 1H), 8.36 (d, 1H, J=5 Hz), 9.7–9.9 (m, 1H), 10.9–11.0 (m, 1H).

EXAMPLE 42

Synthesis of 3-[4-[3-Chloro-5-(4-methoxybenzyloxy)phenyl]-1-piperazinyl]-1-[1-[2-(4-methoxybenzylamino)-4-pyrimidinyl]-5-methyl-4-pyrazolyl]-1-trans-propene 3) Preparation of 3-[4-[3-Chloro-5-(4-methoxybenzyloxy)phenyl]-1-piperazinyl]-1-[1-[2-(4-methoxybenzylamino)-4-pyrimidinyl]-5-methyl-4-pyrazolyl]-1-trans-propene The compound obtained in Example 38-(7) (350 mg) and 1-[3-chloro-5-(4-methoxybenzyloxy)phenyl]piperazine

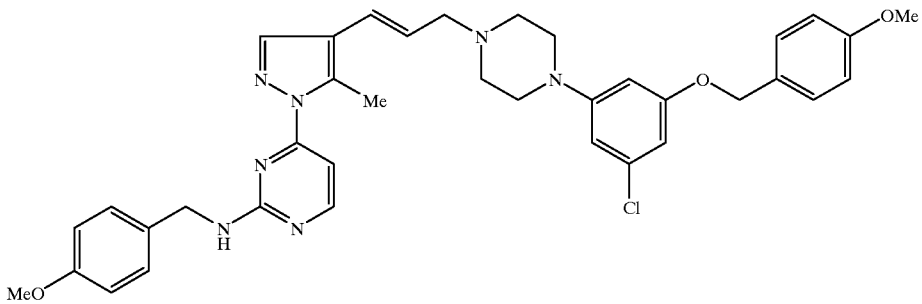

1) Preparation of 1-Bromo-3-chloro-5-(4-methoxybenzyloxy)-benzene

To a mixture of 5.8 ml of p-methoxybenzyl alcohol and 90 ml of N-methylpyrrolidone was added 2.13 g of sodium hydride (60% oil dispersion), and the resulting mixture was stirred at room temperature for 45 minutes in a nitrogen atmosphere. To the reaction mixture was added 9.3 g of 1-bromo-3-chloro-5-fluorobenzene, followed by stirring at 50° C. for 3 hours. The reaction mixture was poured into 50 ml of ice-diluted hydrochloric acid and extracted three times with diethyl ether-hexane (1:1 by volume). The organic layer was washed with a saturated sodium chloride aqueous solution and dried over anhydrous sodium sulfate. The solvent was evaporated, and the residue was purified by silica gel column chromatography using a hexane-ethyl acetate (19:1 by volume) mixed solvent. The fraction containing the desired compound was concentrated to furnish 13.2 g of the title compound.

$^1$H-NMR (CDCl$_3$) δ: 3.82 (s, 3H), 4.94 (s, 2H), 6.90 (t, 1H, J=2 Hz), 6.92 (d, 2H, J=8 Hz), 7.02 (t, 1H, J=2 Hz), 7.11 (t, 1H, J=2 Hz), 7.32 (d, 2H, J=8 Hz).

2) Preparation of 1-[3-Chloro-5-(4-methoxybenzyloxy)phenyl]piperazine

A mixture consisting of 13.2 g of the compound obtained in (1), 13.9 g of piperazine, 810 mg of PdCl$_2$[(o-tolyl)$_3$P]$_2$, 5.4 g of sodium t-butoxide, and 200 ml of toluene was heated at 100° C. for 14 hours while stirring in a nitrogen atmosphere. After cooling to room temperature, the reaction mixture was filtered using Celite, and the filtrate was concentrated. The concentrate was purified by silica gel column chromatography using chloroform-methanol (19:1 by volume) as a developing solvent. The fraction containing the desired compound was concentrated to afford 6.01 g of the title compound.

$^1$H-NMR (CDCl$_3$) δ: 3.00 (m, 4H), 3.13 (m, 4H), 3.82 (s, 3H), 4.93 (s, 2H), 6.38 (t, 1H, J=2 Hz), 6.47 (t, 1H, J=2 Hz), 6.52 (t, 1H, J=2 Hz), 6.92 (d, 2H, J=8 Hz), 7.34 (d, 2H, J=8 Hz).

(400 g) were reacted and worked up in the same manner as in Example 38-(8) to yield 628 mg of the title compound.

$^1$H-NMR (CDCl$_3$) δ: 2.55–2.65 (m, 4H), 2.64 (s, 3H), 3.15–3.25 (m, 6H), 3.80 (s, 3H), 3.82 (s, 3H), 4.58 (d, 2H, J=6 Hz), 4.93 (s, 2H), 5.50 (br, 1H), 6.06 (dt, 1H, J=16, 7 Hz), 6.37 (d, 1H, J=16 Hz), 6.38 (t, 1H, J=2 Hz), 6.47 (t, 1H, J=2 Hz), 6.52 (t, 1H, J=2 Hz), 6.88 (d, 2H, J=9 Hz), 6.91 (d, 2H, J=9 Hz), 7.17 (d, 1H, J=5 Hz), 7.25–7.30 (m, 2H), 7.33 (d, 2H, J=9 Hz), 7.79 (s, 1H), 8.30 (d, 1H, J=5 Hz).

EXAMPLE 43

Synthesis of 1-[1-(2-Amino-4-pyrimidinyl)-5-methyl-4-pyrazolyl]-3-[4-(3-chloro-5-hydroxy-phenyl)-1-piperazinyl]-1-trans-propene Hydrochloride

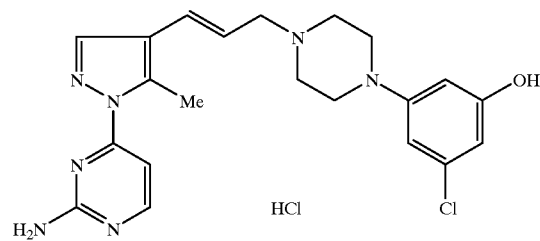

A mixture consisting of 625 g of the compound obtained in Example 42-(3), 7 ml of triflfuoroacetic acid, and 0.225 ml of anisole was treated in the same manner as in Example 37 to yield 166 mg of the title compound.

Melting point: 218–231° C. (decomposition)

$^1$H-NMR (DMSO-d$_6$) δ: 2.74 (s, 3H), 3.05–3.15 (m, 4H), 3.45–3.55 (m, 2H), 3.75–3.85 (m, 2H), 3.90–3.95 (m, 2H), 6.22 (dt, 1H, J=16, 7 Hz), 6.32 (d, 2H, J=2 Hz), 6.50 (t, 1H, J=2 Hz), 6.82 (d, 1H, J=16 Hz), 7.07 (d, 1H, J=5 Hz), 7.22 (br, 1H), 8.13 (s, 1H), 8.32 (d, 1H, J=5 Hz), 9.78 (br, 1H), 10.69 (br, 1H).

EXAMPLE 44

Synthesis of 3-[4-[3-t-Butoxycarbonylaminomethyl)-5-fluorophenyl]-1-piperazinyl]-1-[1-[2-(4-methoxybenzylamino)-4-pyrimidinyl]-5-methyl-4-pyrazolyl]-1-trans-propene

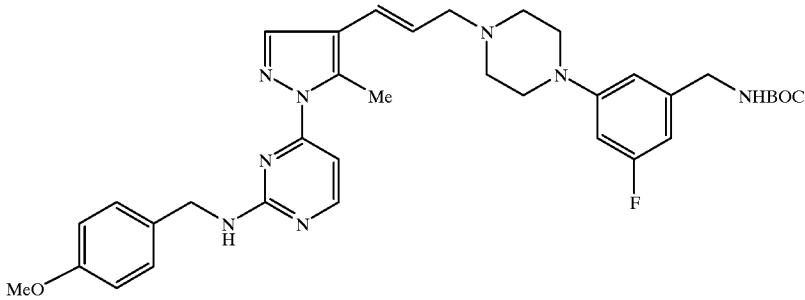

1) Preparation of 1-(3-Cyano-5-fluorophenyl)-4-(2,2,2-trichloroethoxycarbonyl)piperazine In 30 ml of dichloromethane was suspended 2.54 g of 1-(3-cyano-5-fluorophenyl)piperazine hydrochloride, and the suspension was cooled to 0° C. To the suspension were added 7.3 ml of triethylamine and 3 ml of 2,2,2-trichloroethyl chloroformate, followed by stirring at room temperature for 2 hours. The reaction mixture was washed with water and then with a saturated sodium chloride aqueous solution and dried over anhydrous sodium sulfate. The solvent was evaporated, and the residue was subjected to silica gel column chromatography using chloroform as a developing solvent. The fraction containing the desired compound was concentrated to give 4.79 g of the title compound.

$^1$H-NMR (CDCl$_3$) δ: 3.20–3.30 (m, 4H), 3.65–3.80 (m, 4H), 4.79 (s, 2H), 6.79 (dt, 1H, J=11, 2 Hz), 6.80–6.85 (m, 1H), 6.90–6.95 (m, 1H).

2) Preparation of 1-[3-(t-Butoxycarbonylaminomethyl)-5-fluorophenyl]-4-(2,2,2-trichloroethoxycarbonyl)piperazine To 4.79 g of the compound obtained in (1) were added 100 ml of ethanol, 11 ml of a 1N hydrochloric acid/ethanol solution, and 4.0 g of 10% palladium-on-carbon, and catalytic hydrogenation was carried out under a pressure of 4 kg/cm$^2$ for 72 hours. The insoluble matter was removed by filtration, and the filtrate was concentrated. To the residue was added 50 ml of dichloromethane, and the mixture was cooled to 0° C. To the mixture was added 4.3 g of di-t-butyl dicarbonate, followed by stirring at 0° C. for 2 hour. The reaction mixture was washed with a saturated sodium chloride aqueous solution and dried over anhydrous sodium sulfate. The solvent was removed by evaporation, and the residue was subjected to silica gel column chromatography using a 4:1 (by volume) mixture of hexane and ethyl acetate as a developing solvent. The fraction containing the desired compound was concentrated to give 2.1 g of the title compound.

$^1$H-NMR (CDCl$_3$) δ: 1.46 (s, 9H), 3.15–3.25 (m, 4H), 3.65–3.75 (m, 4H), 4.25 (d, 2H, J=6 Hz), 4.79 (s, 2H), 4.85 (br, 1H), 6.45–6.55 (m, 2H), 6.60 (brs, 1H).

3) Preparation of 1-[3-(t-Butoxycarbonylaminomethyl)-5-fluorophenyl]piperazine In a mixture of 100 ml of ethyl acetate and 10 ml of acetic acid was dissolved 2.1 g of the compound obtained in (2), and 10 g of zinc powder was added to the solution over a 30 minute period. After the addition, the mixture was stirred at room temperature for 5 hours. Any insoluble matter was removed by filtration, and the filtrate was washed successively with a saturated sodium hydrogencarbonate aqueous solution and a saturated sodium chloride aqueous solution and dried over anhydrous sodium sulfate. The solvent was removed by evaporation to yield 1.4 g of the title compound.

$^1$H-NMR (CDCl$_3$) δ: 1.46 (s, 9H), 3.05–3.15 (m, 4H), 3.20–3.25 (m, 4H), 4.84 (br, 1H), 6.45–6.55 (m, 2H), 6.58 (brs, 1H).

4) Preparation of 3-[4-[3-(t-Butoxycarbonylaminomethyl)-5-fluorophenyl]-1-piperazinyl]-1-[1-[2-(4-methoxybenzylamino)-4-pyrimidinyl]-5-methyl-4-pyrazolyl]-1-trans-propene The compound obtained in Example 38-(7) (350 mg) and 1-[3-(t-butoxycarbonylaminomethyl)-5-fluorophenyl]piperazine (290 mg) were reacted and worked up in the same manner as in Example 38-(8) to obtain 510 mg of the title compound.

$^1$H-NMR (CDCl$_3$) δ: 1.55 (s, 9H), 2.5–2.6 (m, 4H), 2.64 (s, 3H), 3.1–3.2 (m, 6H), 3.80 (s, 3H), 4.2–4.3 (m, 2H), 4.58 (d, 2H, J=6 Hz), 6.08 (dt, 1H, J=16, 7 Hz), 6.38 (d, 1H, J=16 Hz), 6.4–6.5 (m, 2H), 6.59 (s, 1H), 6.88 (d, 2H, J=8 Hz), 7.18 (d, 1H, J=5 Hz), 7.27 (d, 2H, J=8 Hz), 7.79 (1H, 2), 8.32 (d, 1H, J=5 Hz).

EXAMPLE 45

Synthesis of 1-[1-(2-Amino-4-pyrimidinyl)-5-methyl-4-pyrazolyl]-3-[4-(3-aminomethyl-5-fluorophenyl)-1-piperazinyl]-1-trans-propene Hydrochloride

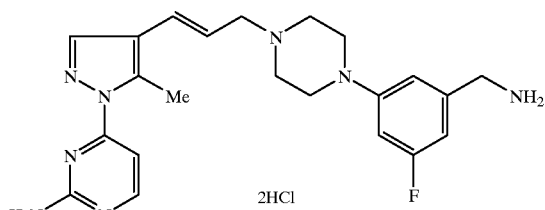

A mixture consisting of 510 mg of the compound obtained in Example 44-(4), 10 ml of trifluoroacetic acid, and 0.23 ml of anisole was treated in the same manner as in Example 37 to afford 200 mg of the title compound.

Melting point: 200–208° C. (decomposition)

¹H-NMR (DMSO-d₆) δ: 2.74 (s, 3H), 3.1–3.2 (m, 2H), 3.2–3.3 (m, 2H), 3.5–3.6 (m, 2H), 3.9–4.0 (m, 6H), 6.30 (dt, 1H, J=16, 7 Hz), 6.80 (d, 1H, J=12 Hz), 6.84 (d, 1H, J=16 Hz), 6.88 (d, 1H, J=12 Hz), 7.06 (s, 1H), 7.19 (d, 1H, J=5 Hz), 8.21 (s, 1H), 8.35 (d, 1H, J=5 Hz).

EXAMPLE 46

Synthesis of 3-[4-(3-Fluoro-5-methoxycarbonylphenyl)-1-piperazinyl]-1-[1-[2-(4-methoxybenzylamino)-4-pyrimidinyl]-5-methyl-4-pyrazolyl]-1-trans-propene

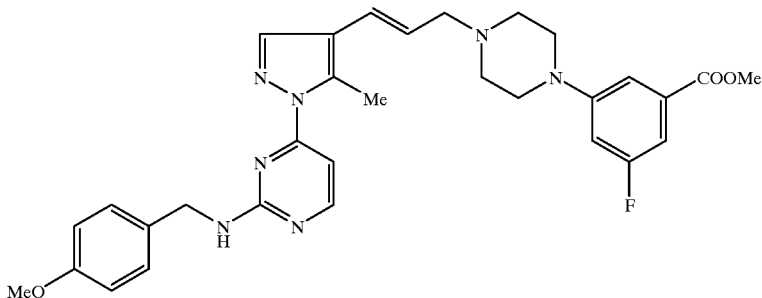

1) Preparation of 1-[3-Fluoro-5-(trifluoromethyl)phenyl]-piperazine

To 60 ml of n-butanol were added 5.0 g of 3-fluoro-5-(trifluoromethyl)aniline and 5.0 g of bis(2-chloroethyl)amine hydrochloride, and the mixture was heated under reflux for 47 hours. To the reaction mixture was added 3.85 g of potassium carbonate, followed by heating under reflux for 24 hours. After cooling to room temperature, the solvent was removed by evaporation. The residue was dissolved in an 1N sodium hydroxide aqueous solution and extracted with chloroform-methanol (19:1 by volume). The extract was washed with a saturated sodium chloride aqueous solution and dried over anhydrous sodium sulfate. The solvent was removed by evaporation, and the residue was subjected to silica gel column chromatography using a 9:1 (by volume) mixed solvent of chloroform and methanol as a developing solvent. The fraction containing the desired compound was concentrated to yield 2.1 g of the title compound.

¹H-NMR (CDCl₃) δ: 3.02 (m, 4H), 3.20 (m, 4H), 6.71 (dm, 1H, J=12 Hz), 6.74 (dm, 1H, J=10 Hz), 6.89 (brs, 1H).

2) Preparation of Methyl 3-Fluoro-5-piperazinobenzoate

To 1.0 g of the compound obtained in (1) above was added 5 ml of concentrated sulfuric acid, followed by stirring at 120° C. for 24 hours. After cooling to room temperature, 20 ml of methanol was slowly added thereto, followed by stirring under reflux for 24 hours. The reaction mixture was poured into a saturated sodium hydrogencarbonate aqueous solution and extracted with ethyl acetate. The organic layer was dried over anhydrous sodium sulfate, and the solvent was evaporated off to furnish 0.86 g of the title compound.

¹H-NMR (CDCl₃) δ: 3.03 (t, 4H, J=5 Hz), 3.20 (t, 4H, J=5 Hz), 3.91 (s, 3H), 6.76 (dm, 1H, J=12 Hz), 7.15 (dm, 1H, J=9 Hz), 7.38 (s, 1H).

3) Preparation of 3-[4-(3-Fluoro-5-methoxycarbonylphenyl)-1-piperazinyl]-1-[1-[2-(4-methoxybenzylamino)-4-pyrimidinyl]-5-methyl-4-pyrazolyl]-1-trans-propene The compound obtained in Example 38-(7) (350 mg) and methyl 3-fluoro-5-piperazinobenzoate (290 mg) were reacted and worked up in the same manner as in Example 38-(8) to afford 590 mg of the title compound.

¹H-NMR (CDCl₃) δ: 2.64 (s, 3H), 2.6–2.7 (4H, m), 3.19 (d, 2H, J=7 Hz), 3.2–3.3 (m, 4H), 3.81 (s, 3H), 3.90 (s, 3H), 4.59 (d, 2H, J=6 Hz), 5.3–5.5 (m, 1H), 6.07 (dt, 1H, J=16, 7 Hz), 6.38 (d, 1H, J=16 Hz), 6.75 (d, 1H, J=9 Hz), 6.88 (d, 2H, J=8 Hz), 7.15 (d, 1H, J=9 Hz), 7.18 (d, 1H, J=5 Hz), 7.27 (d, 2H, J=8 Hz), 7.37 (s, 1H) 7.80 (1H, s), 8.31 (d, 1H, J=5 Hz).

EXAMPLE 47

Synthesis of 1-[1-(2-Amino-4-pyrimidinyl)-5-methyl-4-pyrazolyl]-3-[4-(3-fluoro-5-methoxycarbonylphenyl)-1-piperazinyl]-1-trans-propene Hydrochloride

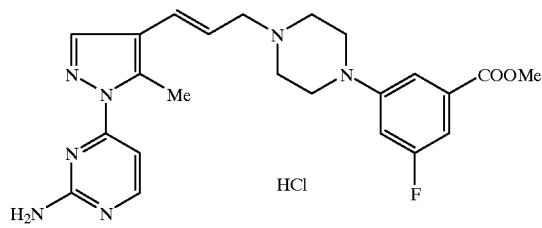

A mixture consisting of 590 mg of the compound obtained in Example 46, 10 ml of trifluoroacetic acid, and 0.3 ml of anisole was treated in the same manner as in Example 37 to give 300 mg of the title compound.

Melting point: 234–237° C. (decomposition)

¹H-NMR (DMSO-d₆) δ: 2.74 (s, 3H), 3.0–3.2 (4H, m), 3.55 (d, 2H, J=7 Hz), 3.86 (s, 3H), 3.9–4.1 (m, 4H), 6.23 (dt, 1H, J=16, 7 Hz), 6.82 (d, 1H, J=16 Hz), 7.09 (d, 1H, J=5 Hz), 7.13 (d, 1H, J=9 Hz), 7.19 (d, 1H, J=9 Hz), 7.36 (s, 1H), 8.32 (s 1H), 8.32 (d, 1H, J=5 Hz).

EXAMPLE 48

Synthesis of 3-[4-(3-Fluoro-5-methoxyphenyl)-1-piperazinyl]-1-[1-[2-(4-methoxybenzylamino)-4-pyrimidinyl]-5-methyl-4-pyrazolyl]-1-trans-propene

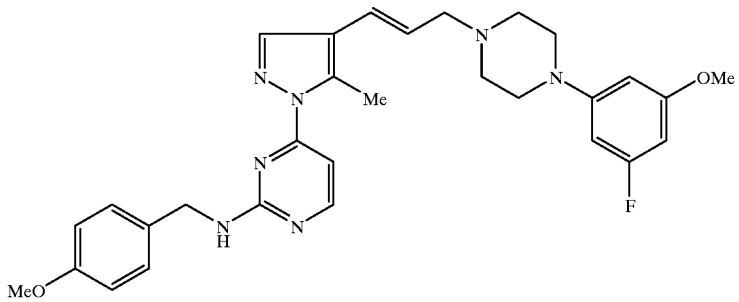

The compound obtained in Example 38-(7) (350 mg) and 1-(3-fluoro-5-methoxyphenyl)piperazine hydrochloride (300 mg) were reacted and worked up in the same manner as in Example 38-(8) to obtain 163 mg of the title compound.

$^1$H-NMR (CDCl$_3$) δ: 2.60–2.65 (m, 4H), 2.64 (s, 3H) 3.18 (d, 2H, J=7 Hz), 3.20–3.25 (m, 4H), 3.76 (s, 3H), 3.80 (s, 3H), 4.58 (d, 2H, J=6 Hz), 5.51 (br, 1H), 6.07 (dt, 1H, J=16, 7 Hz), 6.12 (dt, 1H, J=10, 2 Hz), 6.20–6.30 (m, 2H), 6.37 (d, 1H, J=16 Hz), 6.88 (d, 2H, J=8 Hz), 7.17 (d, 1H, J=5 Hz), 7.25–7.30 (m, 2H), 7.79 (s, 1H), 8.29 (d, 1H, J=5 Hz).

EXAMPLE 49

Synthesis of 1-[1-(2-Amino-4-pyrimidinyl)-5-methyl-4-pyrazolyl]-3-[4-(3-fluoro-5-methoxyphenyl)-1-piperazinyl]-1-trans-propene Hydrochloride

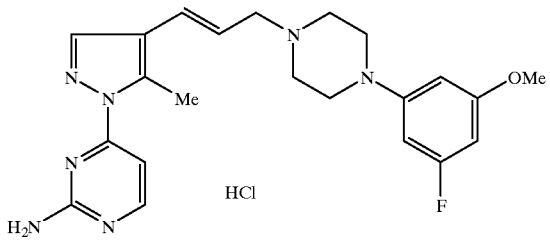

A mixture consisting of 163 mg of the compound obtained in Example 48, 3 ml of trifluoroacetic acid, and 0.036 ml of anisole was treated in the same manner as in Example 37 to give 52 g of the title compound.

Melting point: 205–217° C. (decomposition)

$^1$H-NMR (DMSO-d$_6$) δ: 2.73 (s, 3H), 3.05–3.20 (m, 4H), 3.45–3.55 (m, 2H), 3.74 (s, 3H), 3.85–3.95 (m, 4H), 6.21 (dt, 1H, J=16, 7 Hz), 6.29 (dt, 1H, J=11, 2 Hz), 6.35 (s, 1H), 6.45 (dt, 1H, J=12, 2 Hz), 6.81 (d, 1H, J=16 Hz), 6.96 (br, 2H), 7.01 (d, 1H, J=5 Hz), 8.09 (s, 1H), 8.30 (d, 1H, J=5 Hz), 10.83 (br, 1H).

EXAMPLE 50

Synthesis of 1-[1-(2-Amino-6-benzyloxy-4-pyrimidinyl)-5-methyl-4-pyrazolyl]-3-[4-(3,5-diflurophenyl)-1-piperazinyl]-1-trans-propene

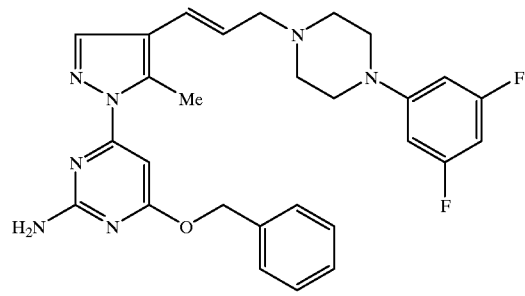

1) Preparation of Ethyl 1-(2-Amino-6-benzyloxy-4-pyrimidinyl)-5-methyl-4-pyrazolecarboxylate To 30 ml of a THF solution of 1.35 ml of benzyl alcohol cooled to 0° C. was added 480 mg of sodium hydride (60% oil dispersion) in a nitrogen atmosphere. After the mixture was stirred at the same temperature for 25 minutes, 1.64 g of 2-amino-4,6-dichloropyrimidine was added thereto, followed by stirring at room temperature for 15 hours. The reaction mixture was concentrated to dryness, and 100 ml of water was added to the residue. The precipitate was collected by filtration to obtain 2.36 g of 2-amino-4-benzyloxy-6-chloropyrimidine as white powder. To the powder was added 30 ml of ethanol, and 3.11 ml of hydrazine monohydrate and 1.38 g of potassium carbonate were added thereto, followed by heat-refluxing for 21 hours. After cooling to room temperature, the reaction mixture was concentrated. Water was added to the residue, and the precipitate was collected by filtration to give 1.95 g of white powder. To the powder were added 30 ml of ethanol and then 1.57 g of ethyl ethoxymethyleneacetoacetate, and the mixture was stirred at room temperature for 1 hour and then refluxed for 5 hours. The reaction mixture was cooled to room temperature, and the solvent was removed by evaporation. The residue was purified by silica gel column chromatography using hexane-ethyl acetate (1:1 by volume) as a developing solvent. The fraction containing the desired compound was concentrated to give 1.72 g of the title compound.

$^1$H-NMR (CDCl$_3$) δ: 1.36 (t, 3H, J=7 Hz), 2.93 (s, 3H), 4.31 (q, 2H, J=7 Hz), 5.01 (brs, 2H), 5.38 (s, 2H), 6.64 (s, 1H), 7.31–7.43 (m, 5H), 7.99 (s, 1H).

2) Preparation of 1-(2-Amino-6-benzyloxy-4-pyrimidinyl)-5-methyl-4-pyrazolecarbaldehyde A methylene chloride solution (50 ml) containing 1.72 g of the compound obtained in (1) was cooled to −78° C. in a nitrogen atmosphere, and 19.5 ml of diisobutylaluminum hydride (1M hexane solution) was added thereto over 30 minutes, followed by stirring at the same temperature for 3 hours. A potassium tartrate aqueous solution was added to the reaction mixture, and the mixture was stirred at room temperature. Any insoluble matter was removed by filtration, and the filtrate was washed with water. The organic layer was dried, and the solvent was removed by evaporation. To the residue were added 50 ml of dioxane and 4.1 g of activated manganese dioxide, and the mixture was stirred at room temperature for 16.5 hours. The insoluble matter was removed by filtration through Celite. Concentration of the filtrate yielded 1.43 g of the title compound.

$^1$H-NMR (CDCl$_3$) δ: 2.96 (s, 3H), 5.02 (br, 2H), 5.39 (s, 2H), 6.70 (s, 1H), 7.30–7.50 (m, 5H), 8.03 (s, 1H), 9.99 (s, 1H).

3) Preparation of Ethyl (E)-3-[1-(2-Amino-6-benzyloxy-4-pyrimidinyl)-5-methyl-4-pyrazolyl]-2-propenoate The procedure of Example 38-(6) was repeated, except for using a mixture of 1.43 g of the compound obtained in (2), 1.93 g of (carboethoxymethylene)triphenylphospholane, and 50 ml of toluene, to give 1.02 g of the title compound.

$^1$H-NMR (CDCl$_3$) δ: 1.33 (t, 3H, J=7 Hz), 2.75 (s, 3H), 4.26 (q, 2H, J=7 Hz), 4.97 (br, 2H), 5.38 (s, 2H), 6.24 (d, 1H, J=16 Hz), 6.68 (s, 1H), 7.30–7.50 (m, 5H), 7.60 (d, 1H, J=16 Hz), 7.86 (s, 1H).

4) Preparation of (E)-3-[1-(2-Amino-6-benzyloxy-4-pyrimidinyl)-5-methyl-4-pyrazolyl]-2-propenal A methylene chloride solution (25 ml) containing 1.02 g of the compound obtained in (3) was cooled to −78° C. in a nitrogen atmosphere, and 11 ml of diisobutylaluminum hydride (1M hexane solution) was added thereto over 20 minutes, followed by stirring at the same temperature for 2.5 hours. A potassium tartrate aqueous solution was added to the reaction mixture, and the mixture was stirred at room temperature for 2 hours. Any insoluble matter was removed by filtration, and the filtrate was washed with water. The organic layer was dried, and the solvent was removed by evaporation. To the residue were added 20 ml of dioxane and 2.5 g of activated manganese dioxide, and the mixture was stirred at room temperature for 24.5 hours. The insoluble matter was removed by filtration through Celite, and the filtrate was concentrated. To the residue were added diethyl ether and hexane, and the precipitate was collected by filtration to yield 787 mg of the title compound.

$^1$H-NMR (CDCl$_3$) δ: 2.79 (s, 3H), 4.99 (br, 2H), 5.39 (s, 2H), 6.54 (dd, 1H, J=16, 8 Hz), 6.70 (s, 1H), 7.30–7.50 (m, 6H), 7.89 (s, 1H), 9.64 (d, 1H, J=8 Hz).

5) Preparation of 1-[1-(2-Amino-6-benzyloxy-4-pyrimidinyl)-5-methyl-4-pyrazolyl]-3-[4-(3,5-difluorophenyl)-1-piperazinyl]-1-trans-propene The compound obtained in (4) (787 mg) and 1-(3,5-difluorophenyl)piperazine hydrochloride (1.10 g) were reacted and worked up in the same manner as in Example 38-(8) to afford 574 mg of the title compound.

$^1$H-NMR (CDCl$_3$) δ: 2.60–2.65 (m, 4H), 2.66 (s, 3H), 3.18 (d, 2H, J=7 Hz), 3.20–3.25 (m, 4H), 4.93 (br, 2H), 5.37 (s, 2H), 6.05 (dt, 2H, J=16, 7 Hz), 6.25 (tt, 1H, J=9, 2 Hz), 6.37 (dd, 2H, J=11, 2 Hz). 6.38 (d, 1H, J=16 Hz), 6.67 (s, 1H), 7.30–7.50 (m, 5H), 7.76 (s, 1H).

EXAMPLE 51

Synthesis of 1-[1-(2-Amino-6-hydroxy-4-pyrimidinyl)-5-methyl-4-pyrazolyl]-3-[4-(3,5-difluorophenyl)-1-piperazinyl]-1-trans-propene Hydrochloride

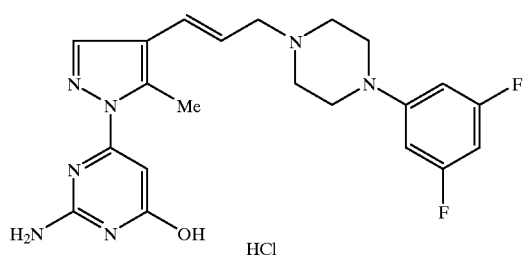

A mixture consisting of 25 mg of the compound obtained in Example 50-(5), 1 ml of trifluoroacetic acid, and 0.025 ml of thioanisole was treated in the same manner as in Example 37 to give 5 mg of the title compound.

Melting point: >300° C.

$^1$H-NMR (DMSO-d$_6$) δ: 2.64 (s, 3H), 3.05–3.15 (m, 4H), 3.50–3.60 (m, 2H), 3.90–4.00 (m, 4H), 5.87 (s, 1H), 6.13 (dt, 1H, J=16, 7 Hz), 6.57 (t 1H, J=9 Hz), 6.70–6.80 (m, 3H), 8.00 (s, 1H), 10.31 (br, 1H), 10.99 (br, 1H).

EXAMPLE 52

Synthesis of 3-[4-(3,5-Difluorophenyl)-1-piperazinyl]-1-[1-[4,6-di(4-methoxybenzylamino)-1,3,5-triazin-2-yl]-5-methyl-4-pyrazolyl]-1-trans-propene

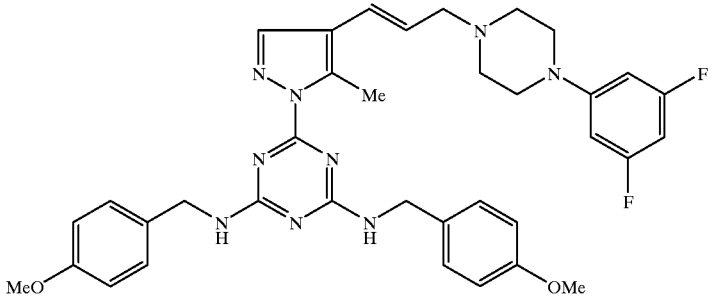

1) Preparation of Ethyl 1-[4,6-Di(4-methoxybenzylamino)-1,3,5-triazin-2-yl]-5-methyl-4-pyrazolecarboxylate In 20 ml of acetone was suspended 1.85 g of cyanuric chloride, and 2.57 ml of 4-methoxybenzylamine was added to the suspension dropwise under cooling with ice. After the mixture was stirred at that temperature for 10 minutes, 20 mL of a 1N sodium hydroxide aqueous solution was added thereto dropwise at room temperature, followed by stirring at room temperature for 15 hours. The precipitate was collected by filtration to obtain 3.11 g of 2-chloro-4,6-di(4-methoxybenzylamino)-1,3,5-triazine as white solid. In 40 ml of ethanol was suspended 2.72 g of the resulting compound, and 2.19 ml of hydrazine monohydrate and 974 mg of potassium carbonate were added thereto, followed by heating under reflux for 15 hours. The reaction mixture was concentrated, and 200 ml of water was added to the residue. The precipitate was collected by filtration to yield 2.55 g of 2-hydrazino-4,6-di(4-methoxybenzylamino)-1,3,5-triazine as white solid. In 10 ml of ethanol was suspended 366 mg of the resulting compound, and 179 mg of ethyl ethoxymethyleneacetoacetate was added thereto at room temperature. The mixture was heated under reflux for 23 hours. The solvent was evaporated, and the residue was subjected to silica gel column chromatography using methanol-chloroform (3:97 by volume) as a developing solvent. The fraction containing the desired compound was concentrated to give 486 mg of the title compound.

$^1$H-NMR (CDCl$_3$) δ: 1.36 (t, 3H, J=Hz), 2.93 and 2.94 (s, 3H each), 3.79 (s, 6H), 4.30 (q, 2H, J=7 Hz), 4.53 and 4.59 (d, 4H, J=6 Hz each), 5.56 and 5.73 (brs, 2H each), 6.83–6.86 (m, 4H), 7.22 (d, 4H, J=9 Hz), 8.01 and 8.02 (s, 1H each).

2) Preparation of 1-[4,6-Di(4-methoxybenzylamino)-1,3,5-triazin-2-yl]-5-methyl-4-pyrazolecarbaldehyde A methylene chloride solution (50 ml) containing 2.82 of the compound obtained in (1) was cooled to −78° C. in a nitrogen atmosphere, and 19.6 ml of diisobutylaluminum hydride (1M hexane solution) was added thereto over 30 minutes, followed by stirring at the same temperature for 30 minutes. To the reaction mixture was added 200 ml of a 20% potassium sodium tartrate aqueous solution, and the mixture was stirred at room temperature for 1 hour. The reaction mixture was extracted with chloroform, the organic layer was dried, and the solvent was removed by evaporation. To the residue were added 60 ml of dioxane and 5.8 g of activated manganese dioxide, and the mixture was stirred at room temperature for 19 hours. The insoluble matter was removed by filtration through Celite, and the filtrate was concentrated to yield 2.11 g of the title compound.

$^1$H-NMR (CDCl$_3$) δ: 2.91 and 2.92 (s, 3H each), 3.79 (s, 6H), 4.52 and 4.59 (d, 1H, J=5 Hz each), 5.66 and 5.82 (brs, 2H each), 6.83–6.88 (m, 4H), 7.22 (d, 4H, J=19 Hz), 8.05 (d, 1H, J=9 Hz), 9.97 and 9.98 (s, 1H each), 10.03 (s, 1H).

3) Preparation of Ethyl (E)-3-[1-[4,6-Di(4-methoxybenzylamino)-1,3,5-triazin-2-yl]-5-methyl-4-pyrazolyl]-2-propenoate The same procedure of Example 38-(6) was repeated, except for using 2.11 g of the compound obtained in (2), 1.92 g of (carboethoxymethylene) triphenylpholane, and 50 ml of toluene, to afford 1.82 g of the title compound.

$^1$H-NMR (CDCl$_3$) δ: 1.32 (t, 3H, J=7 Hz), 2.70 and 2.71 (s, 3H each), 3.79 (s, 6H), 4.25 (q, 2H, J=7 Hz), 4.52 and 4.59 (d, 4H, J=6 Hz each), 5.54 and 5.68 (brs, 2H each), 6.24 and 6.25 (d, 1H, J=16 Hz each), 6.83–6.89 (m, 4H), 7.22 (d, 4H, J=9 Hz), 7.57 (d, 1H, J=16 Hz), 7.89 ad 7.91 (s, 1H each).

4) Preparation of (E)-3-[1-[4,6-Di(4-methoxybenzyl)amino-1,3,5-triazin-2-yl]-5-methyl-4-pyrazolyl]-2-propenal A methylene chloride solution (70 ml) containing 1.82 of the compound obtained in (3) was cooled to −78° C. in a nitrogen atmosphere, and 18.9 ml of diisobutylaluminum hydride (1M hexane solution) was added thereto over a 20 minute period, followed by stirring at the same temperature for 6 hours. To the reaction mixture was added a potassium sodium tartrate aqueous solution, and the mixture was stirred at room temperature for 1 hour. Any insoluble matter was removed by filtration, and the filtrate was washed with water. The organic layer was dried, and the solvent was removed by evaporation. To the residue were added 30 ml of dioxane and 2.99 g of activated manganese dioxide, and the mixture was stirred at room temperature for 12 hours. Chloroform was added to the reaction mixture, and any insoluble matter was removed by filtration through Celite. The filtrate was concentrated to yield 1.49 g of the title compound.

$^1$H-NMR (CDCl$_3$) δ: 2.73 and 2.75 (s, 3H each), 3.80 (s, 6H), 4.52 and 4.60 (d, 4H, J=5 Hz each), 5.58–5.84 (m, 2H), 6.51–6.56 (m, 1H), 6.83–6.89 (m, 4H), 7.22 (d, 4H, J=9 Hz), 7.36 (d, 1H, J=16 Hz), 7.91 and 7.93 (s, 1H each), 9.62 and 9.64 (s, 1H each).

5) preparation of 3-[4-(3,5-Difluorophenyl)-1-piperazinyl]-1-[1-[4,6-di(4-methoxybenzyl)amino-1,3,5-triazin-2-yl]-5-methyl-4-pyrazolyl]-1-trans-propene The procedure of Example 38-(8) was repeated, except for using 471 mg of the compound obtained in (4) above and 250 mg of 1-(3,5-difluorophenyl)piperazine hydrochloride, to obtain 484 mg of the title compound.

$^1$H-NMR (CDCl$_3$) δ: 2.61–2.63 (m, 7H), 3.17 (d, 2H, J=6 Hz), 3.20–3.22 (m, 4H), 3.78 (s, 6H), 4.50 and 4.56 (d, 4H, J=6 Hz each), 5.67 and 5.81 (brs, 2H each), 6.02–6.07 (m, 1H), 6.21–6.26 (m, 1H), 6.35 (d, 4H, J=11 Hz), 6.37 (d, 2H, J=7 Hz), 6.82–6.84 (m, 4H), 7.21 (d, 4H, J=8 Hz), 7.77 and 7.80 (s, 1H each).

EXAMPLE 53

Synthesis of 1-[1-(4,6-Diamino-1,3,5-triazin-2-yl)-5-methyl-4-pyrazolyl]-3-[4-(3,5-difluorophenyl)-1-piperazinyl]-1-trans-propene Hydrochloride

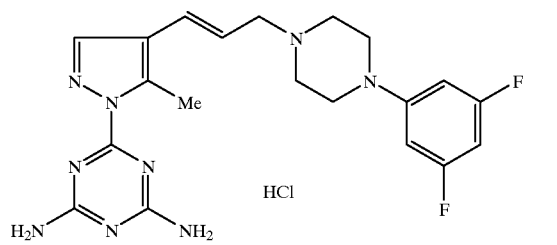

A mixture consisting of 111 mg of the compound obtained in Example 52-(5), 5 ml of triflfuoroacetic acid, and 0.045 ml of anisole was treated in the same manner as in Example 37 to furnish 19 mg of the title compound.

Melting point: 203–207° C. (decomposition)

$^1$H-NMR (DMSO-d$_6$) δ: 2.67 (s, 3H), 3.10 (d, 2H, J=10 Hz), 3.24 (t, 2H, J=13 Hz), 3.51 (d, 2H, J=11 Hz), 3.94–3.98 (m, 4H), 6.26 (dt, 1H, J=16, 8 Hz), 6.57 (t, 1H, J=9 Hz), 6.73 (d, 2H, J=10 Hz), 6.81 (d, 1H, J=16 Hz), 7.73–7.03 (m, 4H), 8.18 (s, 1H), 11.22 (brs, 1H).

EXAMPLE 54

Synthesis of 3-[4-(3-Chloro-5-fluorophenyl)-1-piperazinyl]-1-[1-(4,6-di(4-methoxybenzylamino)-1,3,5-triazine-2-yl]-5-methyl-4-pyrazolyl]-1-trans-propene The compound obtained in Example 52-(4) (1.0 g) and 1-(3-chloro-5-fluorophenyl)piperazine hydrochloride (531 mg) were reacted and worked up in the same manner as in Example 38-(8) to yield 1.26 g of the title compound.

$^1$H-NMR (CDCl$_3$) δ: 2.61–2.63 (m, 7H), 3.17 (d, 2H, J=6 Hz), 3.20–3.22 (m, 4H), 3.78 (s, 6H), 4.50 and 4.56 (d, 4H, J=6 Hz each), 5.67 and 5.81 (brs, 2H each), 6.02–6.07 (m, 1H), 6.21–6.26 (m, 1H), 6.35 (d, 4H, J=11 Hz), 6.37 (d, 2H, J=7 Hz), 6.82–6.84 (m, 4H), 7.21 (d, 4H, J=8 Hz), 7.77 and 7.80 (s, 1H each).

EXAMPLE 55

Synthesis of 1-[1-(4,6-Diamino-1,3,5-triazin-2-yl)-5-methyl-4-pyrazolyl]-3-[4-(3-chloro-5-fluorophenyl)-1-piperazinyl]-1-trans-propene Hydrochloride

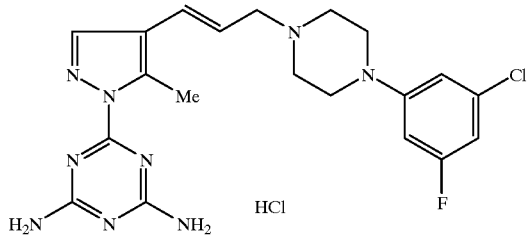

A mixture consisting of 1.26 g of the compound obtained in Example 54, 50 ml of trifluoroacetic acid, and 0.62 ml of anisole was treated in the same manner as in Example 37 to obtain 420 mg of the title compound.

Melting point: 226–232° C. (decomposition)

$^1$H-NMR (DMSO-d$_6$) δ: 2.66 (s, 3H), 3.05–3.13 (m, 2H), 3.22 (t, 2H, J=12 Hz), 3.51 (d, 2H, J=11 Hz), 3.91–3.99 (m, 4H), 6.26 (dt, 1H, J=16, 7 Hz), 6.72–6.92 (m, 4H), 7.58–7.92 (m, 4H), 8.15 (s, 1H), 11.05 (brs, 1H).

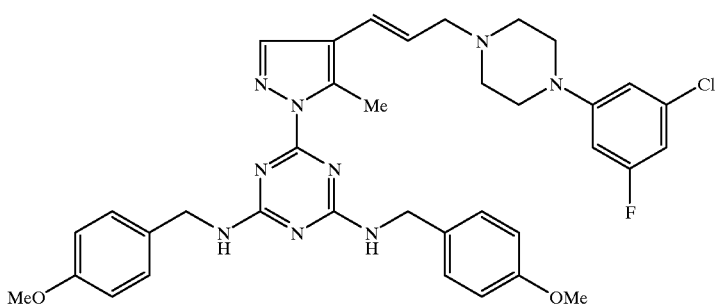

EXAMPLE 56

Synthesis of 1-[1-(2-Amino-4-pyrimidinyl)-5-methyl-4-pyrazolyl]-3-[4-(3-chloro-5-fluorophenyl)-1-piperazinyl]-1-trans-propene Hydrochloride

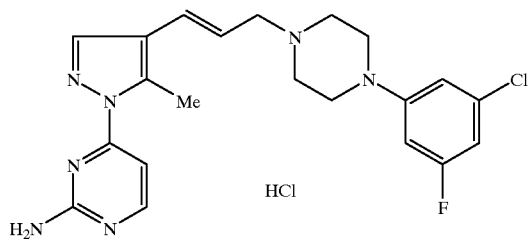

1) Preparation of 1-[1-[2-(4-Methoxybenzylamino)-4-pyrimidinyl]-5-methyl-4-pyrazolyl]-3-[4-(3-chloro-5-fluorophenyl)-1-piperazinyl]-1-trans-propene To a suspension of 0.31 g of 3-[1-[2-(4-methoxybenzylamino-4-pyrimidinyl]-5-methyl-4-pyrazolyl]-2-trans-propenal in 20 ml of ethanol was added 0.30 g of 1-(3-chloro-5-fluorophenyl)piperazine at room temperature. After stirring for 1 hour, 0.45 ml of acetic acid and 0.4 g of sodium cyanoborohydride were added thereto, followed by stirring for 2 days. To the reaction mixture was added 20 ml of a 1N sodium hydroxide aqueous solution, followed by extraction with a 9:1 mixture of chloroform and methanol. The organic layer was washed with a saturated sodium chloride aqueous solution and dried over anhydrous sodium sulfate, and the solvent was removed by evaporation. The residue was subjected to chromatography on a silica gel column using a 99:1 mixture of chloroform and methanol as a developing solvent. The fraction containing the desired compound was concentrated to give 0.47 g of the title compound as colorless syrup.

$^1$H-NMR (CDCl$_3$) δ: 2.5–2.6 (m, 4H), 2.64 (s, 3H), 3.18 (d, 2H, J=7 Hz), 3.2–3.3 (m, 4H), 3.80 (s, 3H), 4.58 (d, 2H, J=6 Hz), 5.51 (brs, 1H), 6.06 (dt, 1H, J=16 Hz, 7 Hz), 6.37 (d, 1H, J=16 Hz), 6.46 (d, 1H, J=8 Hz), 6.53 (d, 1H, J=8 Hz), 6.64 (s, 1H), 6.87 (d, 2H, J=8 Hz), 7.18 (d, 1H, J=6 Hz), 7.27 (d, 2H, J=8 Hz), 7.79 (s, 1H), 8.31 (d, 1H, J=6 Hz).

2) Preparation of 1-[1-(2-Amino-4-pyrimidinyl)-5-methyl-4-pyrazolyl]-3-[4-(3-chloro-5-fluorophenyl)-1-piperazinyl]-1-trans-propene Hydrochloride To 0.47 g of the compound obtained in (1) above were added 10 ml of trifluoroacetic acid and 0.23 ml of anisole, and the mixture was heated under reflux for 4 days. A saturated sodium hydrogencarbonate aqueous solution was added to the reaction mixture, and the mixture was extracted with a 9:1 mixed solvent of chloroform and methanol. The organic layer combined was washed with a saturated sodium chloride aqueous solution and dried over anhydrous sodium sulfate. The solvent was removed by evaporation. The residue was subjected to silica gel column chromatography using a 99:1 mixture of chloroform and methanol as a developing solvent. The fraction containing the desired compound was concentrated, and the concentrate was treated with a 1N ethanolic solution of hydrochloric acid. Recrystallization from ethanol gave 0.23 g of the title compound as a white powder.

$^1$H-NMR (DMSO-d$_6$) δ: 2.64 (s, 3H), 3.0–3.2 (m, 4H), 3.5–3.6 (m, 2H), 3.9–4.0 (m, 4H), 6.28 (dt, 1H, J=16 Hz, 7 Hz), 6.80 (d, 1H, J=16 Hz), 6.81 (d, 1H, J=10 Hz), 6.88 (d, 1H, J=10 Hz), 6.92 (s, 1H), 7.25 (d, 1H, J=6 Hz), 8.22 (s, 1H), 8.36 (d, 1H, J=6 Hz), 10.9–11.0 (m, 1H)

EXAMPLE 57

Synthesis of 1-[1-(2-Amino-6-dimethylamino-4-pyrimidinyl)-5-methyl-4-pyrazolyl]-3-[4-(3,5-difluorophenyl)-1-piperazinyl]-1-trans-propene Hydrochloride

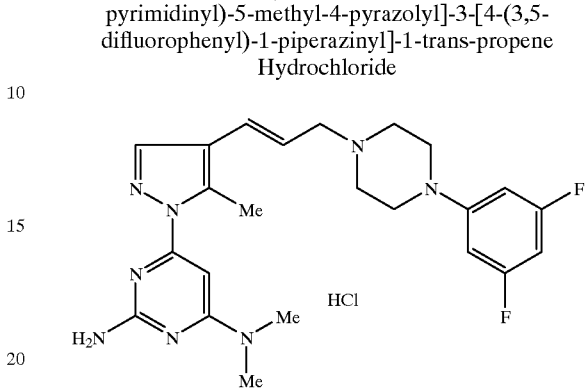

1) Preparation of Ethyl 1-(2-Amino-6-chloro-4-pyrimidinyl)-5-methyl-4-pyrazolecarboxylate To 16.4 g of 2-amino-4,6-dichloropyrimidine was added 300 ml of ethanol, and 25 ml of hydrazine monohydrate and 13.8 g of potassium carbonate were added thereto, followed by heating under reflux for 2 hours. After cooling to room temperature, the reaction mixture was concentrated. Water was added to the concentrate, and the precipitate formed was collected by filtration. To the resulting white powder, which weighed 14.0 g, were added 300 ml of ethanol and 16.3 g of ethyl ethoxymethyleneacetoacetate, and the mixture was stirred at room temperature for 40 minutes and then heat-refluxed for 2 hours. The reaction mixture was cooled to room temperature and filtered to collect 21.9 g of the precipitate as a white powder.

$^1$H-NMR (CDCl$_3$) δ: 1.38 (t, 3H, J=7 Hz), 3.00 (s 3H), 4.33 (q, 2H, J=7 Hz), 5.26 (brs, 2H), 7.33 (s, 1H), 8.02 (s, 1H)

2) Preparation of 1-(2-Amino-6-chloro-4-pyrimidinyl)-5-methyl-4-pyrazolecarbaldehyde A methylene chloride solution (200 ml) containing 5.00 g of the compound obtained in (1) above was cooled to −78° C. in a nitrogen atmosphere, and 84 ml of a 1M hexane solution of diisobutylaluminum hydride was added thereto over 55 minutes, followed by stirring at that temperature for 2.5 hours. Aqueous potassium tartrate was added to the reaction mixture, followed by stirring at room temperature. Any insoluble matter was filtered off, and the filtrate was washed with water. The organic layer was dried, and the solvent was evaporated off. To the residue were added 150 ml of dioxane and 15.5 g of activated manganese dioxide, and the mixture was stirred at room temperature for 66 hours. The insoluble matter was filtered out using Celite, and the filtrate was concentrated to yield 3.90 g of the title compound as a white solid.

$^1$H-NMR (CDCl$_3$) δ: 3.01 (s, 3H), 5.61 (brs, 2H), 7.32 (s, 1H), 8.08 (s, 1H), 10.00 (s, 1H)

3) Preparation of Ethyl 3-[1-(2-Amino-6-chloro-4-pyrimidinyl)-5-methyl-4-pyrazolyl]-2-trans-propenoate A mixture consisting of 3.90 g of the compound obtained in (2) above, 6.86 g of (carboethoxymethylene)

triphenylphospholane, and 150 ml of toluene was stirred at 80° C. for 19 hours. The reaction mixture was cooled to room temperature, and the precipitate formed was collected by filtration to yield 4.11 g of the title compound as a white solid.

$^1$H-NMR (CDCl$_3$) δ: 1.34 (t, 3H, J=7 Hz), 2.79 (s, 3H), 4.26 (q, 2H, J=7 Hz), 5.58 (brs, 2H), 5.38 (s, 2H), 6.27 (d, 1H, J=16 Hz), 7.31 (s, 1H), 7.59 (d, 1H, J=16 Hz), 7.91 (s, 1H)

4) Preparation of Ethyl 3-[1-(2-Amino-6-dimethylamino-4-pyrimidinyl)-5-methyl-4-pyrazolyl]-2-trans-propenoate A mixture consisting of 1.0 g of the compound obtained in (3) above, 1.2 ml of a 50% dimethylamine aqueous solution, and 30 ml of ethanol was stirred at 50° C. for 16.5 hours. While being stirred, the mixture was supplemented with 0.6 ml of a 50% dimethylamine aqueous solution. The reaction mixture was concentrated, water was added to the residue, and the precipitate formed was collected by filtration to afford 999 mg of the title compound as a white powder.

$^1$H-NMR (CDCl$_3$) δ: 1.33 (t, 3H, J=7 Hz), 2.73 (s, 3H), 3.10 (s, 6H), 4.25 (q, 2H, J=7 Hz), 4.76 (brs, 2H), 6.23 (d, 1H, J=16 Hz), 6.37 (s, 1H), 7.60 (d, 1H, J=16 Hz), 7.84 (s, 1H)

5) Preparation of 3-[1-(2-Amino-6-dimethylamino-4-pyrimidinyl)-5-methyl-4-pyrazolyl]-2-trans-propenal A methylene chloride solution (35 ml) of 1.00 g of the compound obtained in (4) above was cooled to −78° C. in a nitrogen atmosphere, and 13 ml of a 1M hexane solution of diisobutylaluminum hydride was added thereto over 10 minutes, followed by stirring at that temperature for 1.5 hours. A potassium tartrate aqueous solution was added to the reaction mixture, and the mixture was stirred at room temperature. The organic layer was separated, and the aqueous layer was extracted 5 times with a 9:1 mixture of chloroform and methanol. The organic layers were combined and dried over anhydrous sodium sulfate. The solvent was evaporated, and 50 ml of dioxane and 2.75 g of activated manganese dioxide were added to the residue, followed by stirring at room temperature for 19 hours. Any insoluble matter was removed by Celite filtration, and the filtrate was concentration. The residue was subjected to silica gel column chromatography using a 99:1 mixture of chloroform and methanol as a developing solution. The fraction containing the desired compound was concentrated to give 756 mg of the title compound as a white powder.

$^1$H-NMR (CDCl$_3$) δ: 2.78 (s, 3H), 3.12 (s, 6H), 4.75 (brs, 2H), 6.40 (s, 1H), 6.53 (dd, 1H, J=16 Hz, 8 Hz), 7.40 (d, 1H, J=16 Hz), 7.88 (s, 1H), 9.63 (d, 1H, J=8 Hz)

6) Preparation of 1-[1-(2-Amino-6-dimethylamino-4-pyrimidinyl)-5-methyl-4-pyrazolyl]-3-[4-(3,5-difluorophenyl)-1-piperazinyl]-1-trans-propene Hydrochloride A mixture consisting of 500 mg of the compound obtained in (5) above, 520 mg of 1-(3,5-difluorophenyl)piperazine hydrochloride, and 50 ml of ethanol was stirred at room temperature for 1 hour and then at 60° C. for 40 minutes. After the reaction mixture was cooled to room temperature, 230 mg of sodium cyanoborohydride was added thereto, followed by stirring at room temperature for 18.5 hours. The reaction mixture was concentrated, a saturated aqueous solution of sodium hydrogencarbonate was added to the residue, and the mixture was extracted three times with a 9:1 mixture of chloroform and methanol. The organic layers combined were washed with a saturated sodium chloride aqueous solution and dried over anhydrous sodium sulfate. The solvent was evaporated, and the residue was subjected to silica gel column chromatography using a 96:4 mixture of chloroform and methanol as a developing solvent. The fraction containing the desired product was concentrated. To the residue was added a 1N ethanolic solution of hydrochloric acid. Concentration followed by recrystallization from ethanol yielded 433 mg of the title compound.

$^1$H-NMR (DMSO-d$_6$) δ: 2.67 (s, 3H), 3.10 (s, 6H), 3.05–3.25 (m, 4H), 3.50–3.55 (m, 2H), 3.90–4.00 (m, 4H), 6.19 (dt, 1H, J=16 Hz, 7 Hz), 6.32 (s, 1H), 6.57 (tm, 1H, J=9 Hz), 6.73 (dm, 2H, J=9 Hz), 6.79 (d, 1H, J=16 Hz), 8.05 (s, 1H), 10.86 (brs, 1H)

EXAMPLE 58

Synthesis of 1-[1-(2,6-Diamino-4-pyrimidinyl)-5-methyl-4-pyrazolyl]-3-[4-(3,5-difluorophenyl)-1-piperazinyl]-1-trans-propene Hydrochloride

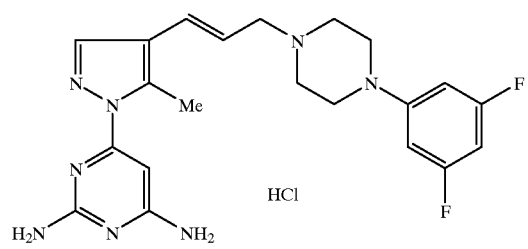

1) Preparation of Ethyl 1-[2-Amino-6-(4-methoxybenzylamino)-4-pyrimidinyl]-5-methyl-4-pyrazolecarboxylate A mixture consisting of 3.0 g of ethyl 1-(2-amino-6-chloro-4-pyrimidinyl)-5-methyl-4-pyrazolecarboxylate, 3.5 ml of 4-methoxybenzylamine, and 150 ml of tetrahydrofuran was heated under reflux for 99 hours. The reaction mixture was cooled to room temperature and concentrated. Water was added to the residue, and the mixture was extracted three times with chloroform. The combined organic layers were washed with a saturated sodium chloride aqueous solution and dried over anhydrous sodium sulfate. The solvent was removed by evaporation, and the residue was purified by silica gel column chromatography using a 49:1 mixture of chloroform and methanol as a developing solvent. The fraction containing the desired product was concentrated to afford 4.08 g of the title compound (amorphous).

$^1$H-NMR (CDCl$_3$) δ: 1.36 (t, 3H, J=7 Hz), 2.91 (s, 3H), 3.80 (s, 3H), 4.31 (q, 2H, J=7 Hz), 4.88 (d, 2H, J=4 Hz), 4.81 (s, 2H), 5.09 (brs, 1H), 6.28 (s, 1H), 6.88 (d, 2H, J=9 Hz), 7.25 (d, 2H, J=9 Hz), 7.96 (s, 1H).

2) Preparation of 1-[2-Amino-6-(4-methoxybenzylamino)-4-pyrimidinyl]-5-methyl-4-pyrazolecarbaldehyde The compound obtained in (1) above weighing 4.08 g was allowed to react and worked up in the same manner as in Example 57-(2) to yield 3.50 g of the title compound as a white powder.

$^1$H-NMR (CDCl$_3$) δ: 2.94 (s, 3H), 3.80 (s, 3H), 4.49 (brs, 2H), 4.83 (s, 2H), 5.13 (brs, 1H), 6.33 (s, 1H), 6.88 (d, 2H, J=9 Hz), 7.25 (d, 2H, J=9 Hz), 8.00 (s, 1H), 9.97 (s, 1H).

3) Preparation of Ethyl 3-[1-[2-Amino-6-(4-methoxybenzylamino)-4-pyrimidinyl]-5-methyl-4-pyrazolyl]-2-trans-propenoate The compound obtained in (2) above weighing 3.50 g and 4.3 g of (carboethoxymethylene)triphenylphospholane were allowed to react and worked up in the same manner as in Example 57-(3) to give 3.22 g of the title compound as a white solid.

$^1$H-NMR (CDCl$_3$) δ: 1.33 (t, 3H, J=7 Hz), 2.73 (s, 3H), 3.80 (s, 3H), 4.25 (q, 2H, J=7 Hz), 4.48 (d, 2H, J=5 Hz), 4.76 (s, 2H), 5.04 (brs, 1H), 6.22 (d, 1H, J=16 Hz), 6.32 (s, 1H), 6.88 (d, 2H, J=8 Hz), 7.20–7.30 (m, 2H), 7.59 (d, 1H, J=16 Hz), 7.83 (s, 1H).

4) Preparation of 3-[1-[2-Amino-6-(4-methoxybenzylamino)-4-pyrimidinyl]-5-methyl-4-pyrazolyl]-2-trans-propenal The compound obtained in (3) above (3.2 g) was allowed to react and worked up in the same manner as in Example 57-(5) to furnish 2.65 g of the title compound as a white powder.

$^1$H-NMR (CDCl$_3$) δ: 2.77 (s, 3H), 3.77 (s, 3H), 4.48 (d, 2H, J=4 Hz), 4.78 (s, 2H), 5.08 (brs, 1H), 6.34 (s, 1H), 6.52 (dd, 1H, J=16 Hz, 8 Hz), 6.88 (d, 2H, J=8 Hz), 7.20–7.30 (m, 2H), 7.39 (d, 1H, J=16 Hz), 7.86 (s, 1H), 9.63 (d, 1H, J=8 Hz).

5) Preparation of 1-[1-[2-Amino-6-(4-methoxybenzylamino)-4-pyrimidinyl]-5-methyl-4-pyrazolyl]-3-[4-(3,5-difluorophenyl)-1-piperazinyl]-1-trans-propene The compound obtained in (4) above (730 mg) and 1-(35-difluorophenyl)piperazine hydrochloride (565 mg) were allowed to react and worked up in the same manner as in Example 57-(6) to afford 881 mg of the title compound as a white solid.

$^1$H-NMR (CDCl$_3$) δ: 2.60–2.65 (m, 4H), 2.65 (s, 3H), 3.18 (d, 2H, J=6 Hz), 3.20–3.25 (m, 4H), 3.80 (s, 3H), 4.47 (d, 2H, J=5 Hz), 4.73 (s, 2H), 5.01 (brs, 1H), 6.03 (dt, 1H, J=16 Hz, 7 Hz), 6.25 (tt, 1H, J=9 Hz, 2 Hz), 6.32 (s, 1H), 6.37 (dd, 2H, J=11 Hz, 2 Hz), 6.38 (d, 1H, J=16 Hz), 6.87 (d, 2H, J=9 Hz), 7.20–7.30 (m, 2H), 7.73 (s, 1H).

6) Preparation of 1-[1-(2,6-Diamino-4-pyrimidinyl)-5-methyl-4-pyrazolyl]-3-[4-(3,5-difluorophenyl)-1-piperazinyl]-1-trans-propene Hydrochloride The compound obtained in (5) above (880 mg) was allowed to react and worked up in the same manner as in Example 56-(2) to afford 82 mg of the title compound.

$^1$H-NMR (DMSO-d$_6$) δ: 2.66 (s, 3H), 3.05–3.25 (m, 2H), 3.30–3.40 (m, 2H), 3.45–3.55 (m, 2H), 3.85–4.00 (m, 4H), 6.15 (dt, 1H, J=16 Hz, 7 Hz), 6.19 (s, 1H), 6.57 (t, 1H, J=9 Hz), 6.65–6.80 (m, 3H), 7.97 (s, 1H), 10.71 (brs, 1H)

EXAMPLE 59

Synthesis of 1-[1-(2-Amino-6-methylamino-4-pyrimidinyl)-5-methyl-4-pyrazolyl]-3-[4-(3,5-difluorophenyl)-1-piperazinyl]-1-trans-propene Hydrochloride

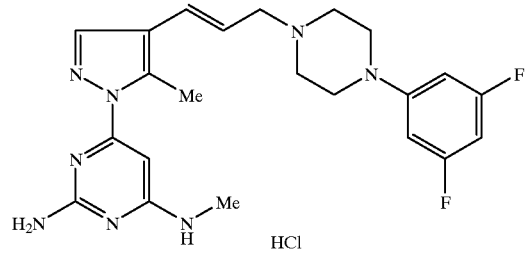

A mixture consisting of 300 mg of 1-[1-(2-amino-6-chloro-4-pyrimidinyl)-5-methyl-4-pyrazolyl]-3-[4-(3,5-difluorophenyl)-1-piperazinyl]-1-trans-propene, 10.2 ml of a 40% methylamine aqueous solution, and 15 ml of ethanol was stirred at 60° C. for 4.5 hours. The reaction mixture was concentrated, and a saturated sodium hydrogencarbonate aqueous solution was added to the residue. The mixture was extracted three times with chloroform. The organic layer was washed with a saturated sodium chloride aqueous solution and dried over anhydrous sodium sulfate. The solvent was removed by evaporation, and the residue was subjected to silica gel column chromatography using a 19:1 mixture of chloroform and methanol as a developing solvent. The fraction containing the desired product was concentrated, and a 1N ethanolic solution of hydrochloric acid was added to the residue. Concentration followed by recrystallization from ethanol gave 95 mg of the title compound as a white powder.

$^1$H-NMR (DMSO-d$_6$) δ: 2.65 (s, 3H), 2.94 (s, 3H), 3.05–3.15 (m, 2H), 3.20–3.30 (m, 2H), 3.40–3.55 (m, 4H), 3.90–4.00 (m, 4H), 6.24 (dt, 1H, J=16 Hz, 7 Hz), 6.41 (brs, 1H), 6.57 (tm, 1H, J=9 Hz), 6.72 (dm, 2H, J=9 Hz), 6.80 (d, 1H, J=16 Hz), 8.14 (s, 1H), 11.12 (brs, 1H).

EXAMPLE 60

Synthesis of 1-[1-(2-Amino-4-dimethylamino-1,3,5-triazin-6-yl)-5-methyl-4-pyrazolyl]-3-[4-(3,5-difluorophenyl)-1-piperazinyl]-1-trans-propene Hydrochloride

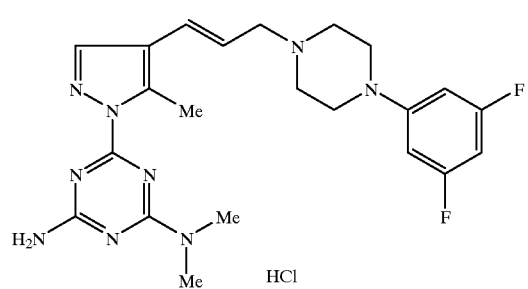

1) Preparation of Ethyl 1-[2-(4-Methoxybenzylamino)-4-dimethylamino-1,3,5-triazin-6-yl]-5-methyl-4-pyrazolecarboxylate In 40 ml of acetone was suspended 2.65 g of 4,6-dichloro-2-(4-methoxybenzylamino)-1,3,5-triazine, and 2.51 ml of a 50% dimethylamine aqueous solution was added to the suspension, followed by stirring at room temperature for 2 days. The solvent was removed by evaporation under reduced pressure, and the residue was suspended in 20 ml of ethanol. To the suspension were added 2.89 ml of hydrazine monohydrate and 1.28 g of potassium carbonate, and the mixture was heated under reflux for 20 hours. The solvent was evaporated off under reduced pressure, water was added to the residue, and the mixture was extracted with chloroform. The organic layer was dried over anhydrous sodium sulfate, and the solvent was evaporated under reduced pressure. The residue was dissolved in 50 ml of ethanol. To the solution was added 1.72 g of ethyl (2-ethoxymethylene) acetoacetate, and the mixture was stirred at room temperature for 2 hours and then heat-refluxed for 16 hours. The solvent was removed by evaporation under reduced pressure, and the residue was subjected to silica gel column chromatography and developed with ethyl acetate. The fraction containing the desired product was concentrated to give 1.01 g of the title compound as a reddish brown solid.

$^1$H-NMR (CDCl$_3$) δ: 1.36 (t, 3H, J=7 Hz), 2.98 (s, 3H), 3.17 (s, 3H), 3.19 (s, 6H), 3.77 (s, 3H), 4.30 (q, 2H, J=7 Hz), 4.54 (d, 2H, J=5 Hz), 6.83 (d, 2H, J=9 Hz), 7.23 (d, 2H, J=8 Hz), 8.00 (2, 1H).

2) Preparation of 1-[2-(4-Methoxybenzylamino)-4-dimethylamino-1,3,5-triazin-6-yl]-5-methyl-4-pyrazolecarbaldehyde The compound obtained in (1) above weighing 1.01 g was allowed to react and worked up in the same manner as in Example 57-(2) to give 847 mg of the title compound as a white solid.

$^1$H-NMR (CDCl$_3$) δ: 2.99 (s, 3H), 3.20 (s, 3H), 3.21 (s, 3H), 3.80 (s, 3H), 4.58 (d, 2H, J=6 Hz), 5.75 (brs, 1H), 6.86 (d, 2H, J=9 Hz), 7.25 (d, 2H, J=7 Hz), 8.07 (s, 1H), 10.02 (s, 1H).

3) Preparation of Ethyl 1-[1-[2-(4-Methoxybenzylamino)-4-dimethylamino-1,3,5-triazin-6-yl]-5-methyl-4-pyrazolyl]-2-trans-propenoate The compound obtained in (2) above weighing 847 mg and 842 mg of (carboethoxymethylene) triphenylphospholane were allowed to react and worked up in the same manner as in Example 57-(3) to yield 491 mg of the title compound as a white solid.

$^1$H-NMR (CDCl$_3$) δ: 1.32 (t, 3H, J=7 Hz), 2.77 (m, 3H), 3.19 (s, 6H), 3.79 (m, 3H), 4.25 (q, 2H, J=7 Hz), 4.58 (d, 2H, J=6 Hz), 5.68 (brs, 1H), 6.26 (d, 1H, J=16 Hz), 6.86 (d, 2H, J=9 Hz), 7.25 (d, 2H, J=8 Hz), 7.60 (d, 1H, J=16 Hz), 7.90 (s, 1H).

4) Preparation of 1-[1-[2-(4-Methoxybenzylamino)-4-dimethylamino-1,3,5-triazin-6-yl]-5-methyl-4-pyrazolyl]-2-trans-propenal The compound obtained in (3) above weighing 491 mg was allowed to react and worked up in the same manner as in Example 57-(5) to yield 438 mg of the title compound as a white solid.

$^1$H-NMR (CDCl$_3$) δ: 2.81 (s, 3H), 3.20 (s, 6H), 3.79 (s, 3H), 4.59 (brs, 2H), 5.71 (brs, 1H), 6.55 (dd, 1H, J=16 Hz, 8 Hz), 6.86 (d, 2H, J=9 Hz), 7.25 (d, 2H, J=9 Hz), 7.39 (d, 1H, J=16 Hz), 7.93 (s, 1H), 9.64 (d, 1H, J=8 Hz).

5) Preparation of 1-[1-[4-Dimethylamino-2-(4-methoxybenzylamino)-1,3,5-triazin-6-yl]-5-methyl-4-pyrazolyl]-3-[4-(3,5-difluorophenyl)-1-piperazinyl]-1-trans-propene The compound obtained in (4) above weighing 438 mg and 313 mg of 1-(3,5-difluorophenyl)piperazine hydrochloride were allowed to react and worked up in the same manner as in Example 57-(6) to afford 498 mg of the title compound as a white powder.

$^1$H-NMR (CDCl$_3$) δ: 2.61–2.69 (m, 7H), 3.18–3.23 (m, 12H), 3.79 (s, 3H), 4.57–4.58 (m, 2H), 5.65–5.66 (m, 1H), 6.06 (dt, 1H, J=16 Hz, 7 Hz), 6.24 (dt, 1H, J=9 Hz, 2 Hz), 6.34–6.40 (m, 2H), 6.85 (d, 2H, J=8 Hz), 7.25 (d, 2H, J=8 Hz), 7.80 (s, 1H).

6) Preparation of 1-[1-(2-Amino-4-dimethylamino-1,3,5-triazin-6-yl)-5-methyl-4-pyrazolyl]-3-[4-(3,5-difluorophenyl)-1-piperazinyl]-1-trans-propene Hydrochloride The compound obtained in (5) above weighing 498 mg was allowed to react and worked up in the same manner as in Example 56-(2) to furnish 209 mg of the title compound as a white powder.

$^1$H-NMR (DMSO-d$_6$) δ: 2.68 (s, 3H), 3.06–3.29 (m, 10H), 3.51 (d, 2H, J=12 Hz), 3.94–3.98 (m, 4H), 5.35 (brs, 2H), 6.30 (dt, 1H, J=16 Hz, 8 Hz), 6.56 (dt, 1H, J=9 Hz, 2 Hz), 6.72 (d, 2H, J=9 Hz), 6.83 (d, 1H, J=16 Hz), 8.21 (s, 1H), 11.34 (brs, 1H).

EXAMPLE 61

Synthesis of 1-[1-(2-Amino-6-dimethylamino-4-pyrimidinyl)-5-methyl-4-pyrazolyl]-3-(4-phenyl-1-piperazinyl)-1-trans-propene Hydrochloride

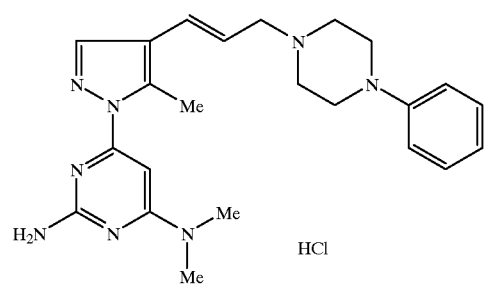

3-[1-(2-Amino-6-dimethylamino-4-pyrimidinyl)-5-methyl-4-pyrazolyl]-2-trans-propenal (50 mg), 36 mg of N-phenylpiperazine, and 15 μl of acetic acid were allowed to react and worked up in the same manner as in Example 56-(1) to give 40 mg of the title compound as a white powder.

$^1$H-NMR (DMSO-d$_6$) δ: 2.65 (s, 3H), 2.9–3.0 (m, 4H), 3.4–3.5 (m, 2H), 3.8–3.9 (m, 2H), 3.9–4.0 (m, 2H), 6.18 (dt, 1H, J=16 Hz, 7 Hz), 6.28 (s, 1H), 6.79 (d, 1H, J=16 Hz), 6.86 (t, 1H, J=8 Hz), 6.99 (d, 2H, J=8 Hz), 7.26 (t, 2H, J=8 Hz), 8.02 (s, 1H), 10.76 (brs, 1H).

EXAMPLE 62

Synthesis of 1-[1-(2-Amino-6-dimethylamino-4-pyrimidinyl)-5-methyl-4-pyrazolyl]-3-[4-(3-pyridyl)-1-piperazinyl]-1-trans-propene Hydrochloride

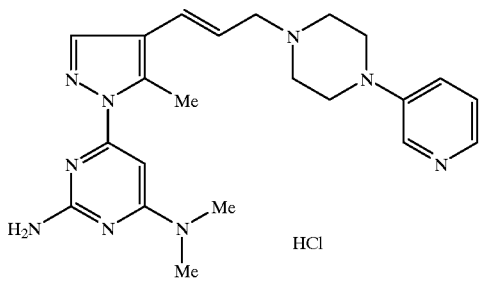

1) Preparation of N-(3-Pyridyl)piperazine

A mixture of 1.0 g (6.3 mmol) of 3-bromopyridine, 2.2 g (25 mmol) of piperazine, 16 mg of tris(dibenzylideneacetone)-dipalladium(0), 32 mg of (S)-(−)-2,2'-bis(diphenylphosphino)-1,1'-binaphthyl, 1.3 g (13.4 mmol) of sodium t-butoxide, and 50 ml of toluene was heated under reflux for 24 hours in a nitrogen atmosphere. The reaction mixture was diluted with water and extracted with chloroform. The combined organic layer was washed with a saturated sodium chloride aqueous solution and dried over anhydrous sodium sulfate. The solvent was evaporated off, and the residue was purified by silica gel column chromatography using a 9:1 mixture of chloroform and methanol as a developing solvent to give 0.27 g (29%) of the title compound.

$^1$H-NMR (CDCl$_3$) δ: 3.05 (t, 4H, J=5 Hz), 3.18 (t, 4H, J=5 Hz), 7.1–7.2 (m, 2H), 8.10 (dd, 1H, J=5 Hz, 2 Hz), 8.31 (d, 1H, J=2 Hz).

2) Preparation of 1-[1-(2-Amino-6-dimethylamino-4-pyrimidinyl)-5-methyl-4-pyrazolyl]-3-[4-(3-pyridyl)-1-piperazinyl]-1-trans-propene Hydrochloride 3-[1-(2-Amino-6-dimethylamino-4-pyrimidinyl)-5-methyl-4-pyrazolyl]-2-trans-propenal (50 mg), 36 mg of the compound obtained in (1) above, and 30 μl of acetic acid were allowed to react and worked up in the same manner as in Example 56-(1) to yield 59 mg of the title compound as a white powder.

$^1$H-NMR (DMSO-d$_6$) δ: 2.60 (s, 3H), 3.0–3.1 (m, 4H), 3.4–3.5 (m, 2H), 3.9–4.0 (m, 2H), 4.1–4.2 (m, 2H), 6.24 (dt, 1H, J=16 Hz, 7 Hz), 6.39 (s, 1H), 6.71 (d, 1H, J=16 Hz), 7.9–8.1 (m, 2H), 8.12 (s, 1H), 8.26 (d, 1H, J=5 Hz), 8.56 (s, 1H), 11.0–11.1 (m, 1H).

EXAMPLE 63

Synthesis of 1-[1-(2-Amino-6-dimethylamino-4-pyrimidin-yl)-5-methyl-4-pyrazolyl]-3-[4-(4-amino-3,5-difluoro)-1-piperazinyl]-1-trans-propene Hydrochloride

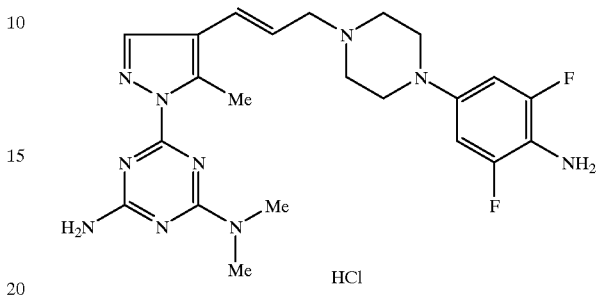

1) Preparation of N-(4-Amino-3,5-difluoro)piperazine

A mixture of 1.0 g (4.8 mmol) of 4-bromo-2,6-difluoroaniline, 50 mg (55 μmol) of tris(dibenzylideneacetone)dipalladium(0), 105 mg (165 μmol) of (S)-(−)-2,2'-bis(diphenylphosphino)-1,1'-binaphthyl, 3.5 g (36.4 mmol) of sodium t-butoxide, and 100 ml of toluene was heated under reflux for 5 hours in a nitrogen atmosphere. The reaction mixture was diluted with water and extracted with chloroform. The combined organic layer was washed with a saturated sodium chloride aqueous solution and dried over anhydrous sodium sulfate. The solvent was removed by evaporation, and the residue was purified by silica gel column chromatography (chloroform/methanol= 95:5) to give 0.26 g (25%) of the title compound.

$^1$H-NMR (CDCl$_3$) δ: 2.83 (t, 2H, J=5 Hz), 2.88 (t, 2H, J=5 Hz), 3.35 (t, 2H, J=5 Hz), 3.53 (t, 2H, J=5 Hz), 6.44 (d, 2H, J=10 Hz).

2) Preparation of 1-[1-(2-Amino-6-dimethylamino-4-pyrimidinyl)-5-methyl-4-pyrazolyl]-3-[4-(4-amino-3,5-difluoro)-1-piperazinyl]-1-trans-propene Hydrochloride 3-[1-(2-Amino-6-dimethylamino-4-pyrimidinyl)-5-methyl-4-pyrazolyl]-2-trans-propenal (50 mg), 0.11 g of the compound obtained in (1) above, and 0.1 ml of acetic acid were allowed to react and worked up in the same manner as in Example 56-(1) to give 44 mg of the title compound as a pale purple powder.

$^1$H-NMR (DMSO-d$_6$) δ: 2.65 (s, 3H), 3.0–3.1 (m, 4H), 3.4–3.5 (m, 2H), 3.9–4.0 (m, 2H), 4.1–4.2 (m, 2H), 6.16 (dt, 1H, J=16 Hz, 7 Hz), 6.26 (s, 1H), 6.66 (dd, 1H, J=10 Hz, 2 Hz), 6.77 (d, 1H, J=16 Hz), 10.73 (brs, 1H).

EXAMPLE 64

Synthesis of 3-[3-[1-(2-Amino-6-dimethylamino-4-pyrimidinyl)-5-methyl-4-pyrazolyl]-2-trans-propen-1-yl]-7,9-difluoro-2,3,4,4a,5,6-hexahydro-1H-pyrazino-[1,2-a]quinoline Hydrochloride (Isomer A)

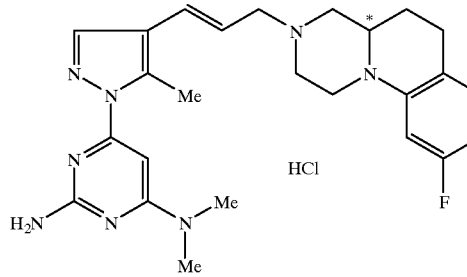

A mixture consisting of 101 mg of 7,9-difluoro-2,3,4,4a,5,6-hexahydro-1H-pyrazino[1,2-a]quinoline (enantiomer A), 122 mg of 3-[1-(2-amino-6-dimethylamino-4-pyrimidinyl)-5-methyl-4-pyrazolyl]-2-trans-propenal, and 20 ml of ethanol was stirred at 80° C. for 1 hour. After the reaction mixture was cooled to room temperature, 0.26 ml of acetic acid was added thereto, and 135 mg of sodium cyanoborohydride was further added in 3 divided portions every hour, followed by stirring at room temperature for 16 hours. Water and a saturated aqueous solution of sodium carbonate were added to the reaction mixture, and the mixture was extracted with chloroform. The organic layer was dried over anhydrous sodium sulfate, and the solvent was removed by evaporation under reduced pressure. The residue was subjected to silica gel column chromatography (270–400 mesh, 25 g) using a 2.5:97.5 mixture of methanol and chloroform as a developing solvent. The fraction containing the desired product was concentrated. The concentrate, which weighed 212 mg, was dissolved in 5 ml of isopropyl alcohol while heating, and 0.5 ml of a 1N ethanolic solution of hydrochloric acid was added thereto while hot. The reaction mixture was allowed to stand at room temperature for 3 hours, and the precipitate was collected by filtration to give 72 mg of the title compound as a white solid.

$^1$H-NMR (DMSO-$d_6$) δ: 1.55–1.75 (m, 1H), 2.0–2.1 (m, 1H), 2.67 (s, 3H), 3.11 (s, 6H), 2.4–3.6 (m, 9H), 3.8–4.0 (m, 2H), 4.13 (d, 1H, J=14 Hz), 6.21 (dt, 1H, J=16 Hz, 7 Hz), 6.32 (s, 1H), 6.50 (dt, 1H, J=9 Hz, 2 Hz), 6.69 (d, 1H, J=12 Hz), 6.79 (d, 1H, J=16 Hz), 8.04 (s, 1H), 11.24 (brs, 1H).

EXAMPLE 65

Synthesis of 3-[3-[1-(2-Amino-6-dimethylamino-methyl-4-pyrimidinyl)-5-methyl-4-pyrazolyl]-2-trans-propen-1-yl]-7,9-difluoro-2,3,4,4a,5,6-hexahydro-1H-pyrazino[1,2-a]quinoline Hydrochloride (Isomer B)

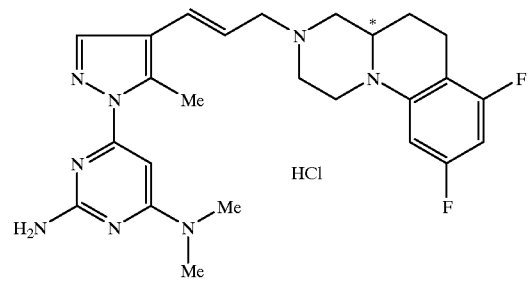

7,9-Difluoro-2,3,4,4a,5,6-hexahydro-1H-pyrazino[1,2-a]quinoline (enantiomer B) (104 mg) and 3-[1-(2-amino-6-dimethylamino-4-pyrimidinyl)-5-methyl-4-pyrazolyl]-2-trans-propenal (126 mg) were allowed to react and worked up in the same manner as in Example 64 to give 76 mg of the title compound as a white solid.

The $^1$H-NMR data of the resulting compound agreed with those of Example 64.

EXAMPLE 66

Synthesis of (+/−)-3-[3-[1-(2-Amino-6-methyl-4-pyrimidinyl)-5-methyl-4-pyrazolyl]-2-trans-propen-1-yl]-7,9-difluoro-2,3,4,4a,5,6-hexahydro-1H-pyrazino[2,1-c]-1,4-benzoxazine Hydrochloride

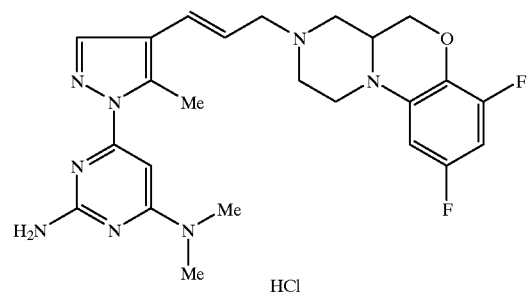

7,9-Difluoro-2,3,4,4a,5,6-hexahydro-1H-pyrazino[2,1-c]-1,4-benzoxazine (80 mg) and 3-[1-(2-amino-6-dimethylamino-4-pyrimidinyl)-5-methyl-4-pyrazolyl]-2-trans-propenal (96 mg) were allowed to react and worked up in the same manner as in Example 64 to yield 61 mg of the title compound.

$^1$H-NMR (DMSO-$d_6$) δ: 2.66 (s, 3H), 2.80–2.95 (m, 1H), 3.0–4.2 (m, 9H), 3.16 (s, 6H), 4.38 (d, 1H, J=9 Hz), 6.22 (dt, 1H, J=16 Hz, 7 Hz), 6.38 (s, 1H), 6.65 (t, 1H, J=9 Hz), 6.80 (d, 1H, J=16 Hz), 6.77–6.82 (m, 1H), 8.10 (s, 1H), 11.47 (brs, 1H).

EXAMPLE 67

Synthesis of 3-[3-[1-(2-Amino-6-dimethylamino-4-pyrimidinyl)-5-methyl-4-pyrazolyl]-2-trans-propen-1-yl]-2,3,4,4a,5,6-hexa-hydro-1H-pyrazino[1,2-a]quinoline Hydrochloride (Isomer A)

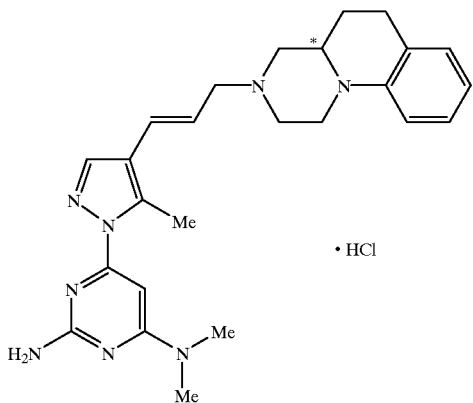

1) Preparation of Ethyl 1-(2-Amino-6-chloro-4-pyrimidinyl)-5-methyl-4-pyrazolecarboxylate A mixture of 16.4 g of 2-amino-4,6-dichloropyrimidine, 25 ml of hydrazine monohydrate, 13.8 g of potassium carbonate, and 300 ml of ethanol was heated under reflux for 2 hours. After cooling to room temperature, the reaction mixture was concentrated under reduced pressure. Water was added to the residue, and the precipitate thus formed was collected by filtration to give 14.0 g of white powder. To the powder were added 300 ml of ethanol and 16.3 g of ethyl ethoxymethyleneacetoacetate, and the mixture was stirred at room temperature for 40 minutes and then heat-refluxed for 2 hours. On cooling the reaction mixture to room temperature, crystals precipitated, which were collected by filtration to yield 21.9 g of the title compound as a colorless crystalline powder.

$^1$H-NMR (CDCl$_3$) δ: 1.38 (t, 3H, J=7 Hz), 3.00 (s, 3H), 4.33 (q, 2H, J=7 Hz), 5.26 (brs, 2H), 7.33 (s, 1H), 8.02 (s, 1H).

2) Preparation of 1-(2-Amino-6-chloro-4-pyrimidinyl)-5-methyl-4-pyrazolecarbaldehyde A dichloromethane solution (120 ml) containing 5.00 g of the compound obtained in (1) above was cooled to −78° C. in a nitrogen atmosphere, and 76 ml of a 1M hexane solution of diisobutylaluminum hydride was added thereto over 30 minutes, followed by stirring at that temperature for 5 hours. To the reaction mixture was added 100 ml of a 10% potassium tartrate aqueous solution, followed by stirring at room temperature for 15 hours. The reaction mixture was extracted with a 1:9 mixture of methanol and chloroform. The organic layer was dried, and the solvent was evaporated under reduced pressure. To the residue were added 120 ml of dioxane and 14.9 g of activated manganese dioxide, and the mixture was stirred at room temperature for 24 hours. The insoluble matter was removed by Celite filtration, and the filtrate was concentrated. Diethyl ether was added to the residue, followed by stirring at room temperature for 3 hours. The precipitate thus formed was collected by filtration to afford 3.90 g of the title compound as a white solid.

$^1$H-NMR (CDCl$_3$) δ: 3.01 (s, 3H, s, CH$_3$), 5.61 (br, 0.5H), 7.32 (s, 1H), 8.08 (s, 1H), 10.00 (s, 1H).

3) Preparation of Ethyl 3-[1-(2-Amino-6-chloro-4-pyrimidinyl)-5-methyl-4-pyrazolyl]-2-trans-propenoate A mixture consisting of 3.90 g of the compound obtained in (2) above, 6.95 g of (carboethoxymethylene)-triphenylphospholane, and 80 ml of toluene was stirred at 80° C. for 16 hours and then at room temperature for 24 hours. The precipitate formed was collected by filtration to give 4.11 g of the title compound as a white solid.

$^1$H-NMR (CDCl$_3$) δ: 1.34 (t, 3H, J=7 Hz), 2.79 (s, 3H), 4.26 (q, 2H, J=7 Hz), 5.58 (br, 0.5H), 5.38 (s, 2H), 6.27 (d, 1H, J=16 Hz), 7.31 (s, 1H), 7.59 (d, 1H, J=16 Hz), 7.91 (s, 1H).

4) Preparation of Ethyl 3-[1-(2-Amino-6-dimethylamino-4-pyrimidinyl)-5-methyl-4-pyrazolyl]-2-trans-propenoate A mixture consisting of 1.0 g of the compound obtained in (3) above, 1.2 ml of a 50% dimethylamine aqueous solution, and 30 ml of ethanol was stirred at 50° C. for 16.5 hours. While being stirred, the mixture was supplemented with 0.6 ml of a 50% dimethylamine aqueous solution. The reaction mixture was cooled to room temperature and concentrated to dryness under reduced pressure. Water was added to the residue, and the precipitate was collected by filtration to give 999 mg of the title compound as a white powder.

$^1$H-NMR (CDCl$_3$) δ: 1.33 (t, 3H, J=7 Hz), 2.73 (s, 3H), 3.10 (s, 6H), 4.25 (q, 2H, J=7 Hz), 4.76 (brs, 2H), 6.23 (d, 1H, J=16 Hz), 6.37 (s, 1H), 7.60 (d, 1H, J=16 Hz), 7.84 (s, 1H).

5) Preparation of 3-[1-(2-Amino-6-dimethylamino-4-pyrimidinyl)-5-methyl-4-pyrazolyl]-2-trans-propenal To 1.00 g of the compound obtained in (4) above was added 100 ml of dichloromethane, and 25 ml of a 1M hexane solution of diisobutylaluminum hydride was added thereto dropwise at −78° C. in a nitrogen atmosphere, followed by stirring at that temperature for 15 minutes and then for 30 minutes under ice-cooling. A saturated potassium tartrate aqueous solution was added to the reaction mixture, followed by stirring at room temperature. The mixture was extracted with 10% methanol-chloroform, and the organic layer was dried over anhydrous sodium sulfate. The solvent was removed by evaporation under reduced pressure. The aqueous layer was subjected to column chromatography on an HP-20 column and eluted with methanol. The eluate was combined with the extract and concentrated. To the residue were added 100 ml of 1,4-dioxane and 5.27 g of activated manganese dioxide, and the mixture was stirred at 50° C. for 16 hours. Any insoluble matter was removed by Celite filtration and washed with the organic layer of a 7:3:1 mixture of chloroform, methanol, and water, and the solvent was removed by evaporation. The residue was recrystallized from an ethanol-diethyl ether mixed solvent to give 756 mg of the title compound as a white powder.

$^1$H-NMR (CDCl$_3$) δ: 2.78 (s, 3H), 3.12 (s, 6H), 4.75 (brs, 2H), 6.40 (s, 1H), 6.53 (dd, 1H, J=16 Hz, 8 Hz), 7.40 (d, 1H, J=16 Hz), 7.88 (s, 1H), 9.63 (d, 1H, J=8 Hz).

6) Preparation of 3-[3-[1-(2-Amino-6-dimethylamino-4-pyrimidinyl)-5-methyl-4-pyrazolyl]-2-trans-propen-1-yl]-2,3,4,4a,5,6-hexahydro-1H-pyrazino[1,2-a]quinoline Hydrochloride (Isomer A)

In 10 ml of ethanol were suspended 206 mg of (+)-2,3,4,4a,5,6-hexahydro-1H-pyrazino[1,2-a]quinoline hydrochloride and 50 mg of the aldehyde obtained in (5) above, and 40 mg of sodium borohydride was added thereto. After stirring the mixture at room temperature for 24 hours, water and a saturated sodium carbonate aqueous solution were added thereto, and the mixture was extracted with chloroform. The organic layer was dried over anhydrous sodium sulfate, and the solvent was removed by evaporation under reduced pressure. The residue was purified by silica gel column chromatography using a 2:98 mixture of methanol and chloroform as a developing solvent. A 1N ethanolic solution of hydrochloric acid was added to the resulting compound (in a free form) weighing 10 mg, and the solvent was evaporated. The residue was recrystallized from isopropyl alcohol to yield 5 mg of the title compound.

Melting point: 198° C. or higher (with decomposition)

$^1$H-NMR (DMSO-$d_6$) δ: 1.60–1.80 (m, 1H), 1.95–2.10 (m, 1H), 2.67 (s, 3H), 2.60–3.00 (m, 3H), 3.00–3.20 (m, 2H), 3.19 (s, 6H), 3.30–3.70 (m, 4H), 3.85–4.00 (m, 1H), 4.10–4.20 (m, 1H), 6.26 (dt, 1H, J=16 Hz, 7 Hz), 6.41 (s, 1H), 6.70 (t, 1H, J=8 Hz), 6.82 (d, 1H, J=16 Hz), 6.90 (d, 1H, J=8 Hz), 6.98 (d, 1H, J=6 Hz), 7.04–7.08 (m, 1H), 8.12 (s, 1H).

EXAMPLE 68

Synthesis of 3-[3-[1-(2-Amino-6-dimethylamino-4-pyrimidinyl)-5-methyl-4-pyrazolyl]-2-trans-propen-1-yl]-2,3,4,4a,5,6-hexahydro-1H-pyrazino[1,2-a]quinoline Hydrochloride (Isomer B)

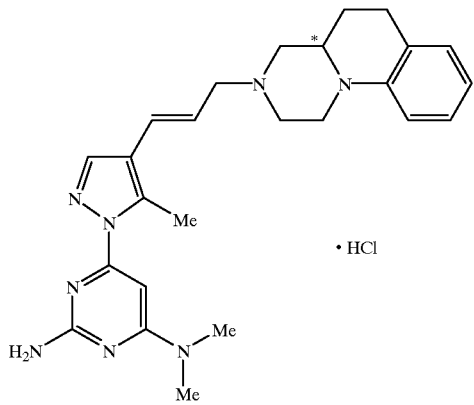

(−)-2,3,4,4a,5,6-Hexahydro-1H-pyrazino[1,2-a]quinoline hydrochloride (206 mg) and the aldehyde obtained in Example 67-(5) (50 mg) were allowed to react and worked up in the same manner as in Example 67-(6) to give 20 mg of the title compound.

Melting point: 191° C. or higher (with decomposition)

The $^1$H-NMR data of the product were in complete agreement with those of the compound obtained in Example 67-(6).

EXAMPLE 69

Synthesis of 3-[3-[1-(2-Amino-6-dimethyl-amino-4-pyrimidinyl)-5-methyl-4-pyrazolyl]-2-trans-propen-1-yl]-9-fluoro-2,3,4,4a,5,6-hexahydro-1H-pyrazin[1,2-a]quinoline Hydrochloride (Isomer A)

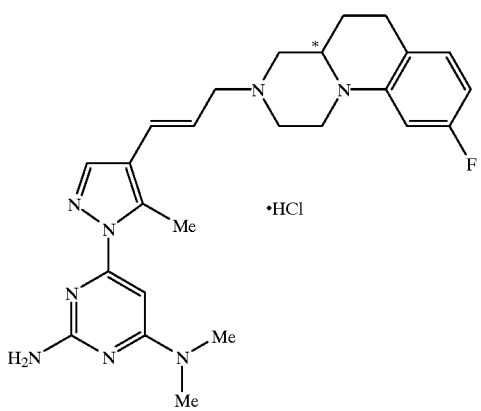

1) Preparation of 7-Fluoro-2-quinolinecarboxylic Acid

A mixture of 9.1 ml of bromine and 8 ml of acetic acid was added to a mixture of 9.64 g of 7-fluoroquinaldine, 30 g of sodium acetate, and 60 ml of acetic acid at 70° C. over a period of 20 minutes. The reaction mixture was stirred at 90° C. for 1 hour, cooled to room temperature, and concentrated under reduced pressure. Water was added to the residue, and the insoluble matter was collected by filtration and washed with water to give 20.0 g of 7-fluoro-2-tribromoquinoline. To the resulting compound was added 200 ml of concentrated sulfuric acid, followed by stirring at 125° C. for 20 hours. The reaction mixture was poured into about 600 ml of ice. The resulting acidic aqueous solution was made alkaline by addition of a 28% aqueous ammonia, adjusted to pH around 4 by addition of a 1N phosphoric acid aqueous solution, and extracted with chloroform. The organic layer was dried and concentrated. The residue was subjected to silica gel column chromatography using a 9:1 mixture of chloroform and methanol as a developing solvent. The fraction containing the desired compound was concentrated to yield 9.04 g of the title compound.

$^1$H-NMR (CDCl$_3$) δ: 7.52 (t, 1H, J=9 Hz), 7.80 (d, 1H, J=9 Hz), 7.97 (dd, 1H, J=6 Hz, 9 Hz), 8.27 (d, 1H, J=8 Hz), 8.43 (d, 1H, J=8 Hz).

2) Preparation of 7-Fluoro-2-[N-(1-phenylethyl) carbamoyl]-1,2,3,4-tetrahydroquinoline (Diastereomers A and B)

In 300 ml of acetic acid was dissolved 9.04 g of the compound obtained in (1) above, and 1.0 g of platinum oxide was added thereto to conduct catalytic hydrogenation for 6 hours. Any insoluble matter was removed by filtration, and the filtrate was concentrated to dryness. The solid was dissolved in ethyl acetate and washed successively with water and a saturated sodium chloride aqueous solution. The organic layer was dried over anhydrous sodium sulfate, and the solvent was removed by evaporation under reduced pressure. The residue was dissolved in 300 ml of dichloromethane, and 8.5 g of (S)-(−)-1-phenylethylamine, 8.6 g of dimethylaminopyridine, and 17 g of 1-ethyl-3-(3-dimethylaminopropyl) carbodiimide hydrochloride were added to the solution, followed by stirring at room temperature for 20 hours. The reaction mixture was washed successively with water, a 1N phosphoric acid aqueous solution, and a saturated sodium chloride aqueous solution and dried over anhydrous sodium sulfate. The solvent was evaporated off under reduced pressure. The residue was subjected to silica gel column chromatography using a 2:5 mixture of ethyl acetate and hexane as a developing solvent to furnish 5.78 g of a low polar isomer of the title compound (diastereomer A) and 5.17 g of a high polar isomer of the title compound (diastereomer B).

Diastereomer A $^1$H-NMR (CDCl$_3$) δ: 1.45 (d, 3H, J=7 Hz), 1.85–1.94 (m, 1H), 2.30–2.38 (m, 1H), 2.50–2.59 (m, 1H), 2.65–2.75 (m, 1H), 3.96 (q, 1H, J=5 Hz), 4.19 (d, 1H, J=5 Hz), 5.12–5.20 (m, 1H, 6.32 (dd, 1H, J=2 Hz, 10 Hz), 6.41 (dt, 1H, J=2 Hz, 8 Hz), 6.88 (d, 1H, J=8 Hz), 6.93 (t, 1H, J=8 Hz), 7.25–7.40 (m, 5H).

Diastereomer B $^1$H-NMR (CDCl$_3$) δ: 1.49 (d, 3H, J=7 Hz), 1.83–1.91 (m, 1H), 2.24–2.32 (m, 1H), 2.37–2.45 (m, 1H), 2.60–2.67 (m, 1H), 4.01 (q, 1H, J=5 Hz), 4.24 (d, 1H, J=5 Hz), 5.10–5.17 (m, 1H), 6.36 (dd, 1H, J=2 Hz, 10 Hz), 6.42 (dt, 1H, J=2 Hz, 8 Hz), 6.90 (d, 1H, J=8 Hz), 6.85–6.95 (br, 1H), 7.15–7.30 (m, 5H).

3) Preparation of 7-Fluoro-2-[N-(1-phenylethyl)-N-t-butoxycarbonylaminomethyl]-1,2,3,4-tetrahydroquinoline (Diastereomer A)

In 80 ml of tetrahydrofuran was dissolved 5.78 g of the diastereomer A obtained in (2) above, and 16 ml of a borane-dimethyl sulfide complex was added thereto while stirring at 0° C., followed by stirring at room temperature for 3 days. A 6N hydrochloric acid aqueous solution was added thereto, followed by stirring for 1 hour. The reaction mixture was neutralized with a saturated sodium hydrogencarbonate aqueous solution and extracted with chloroform. The organic layer was washed with a saturated sodium chloride aqueous solution and dried over anhydrous sodium sulfate. The solvent was evaporated under reduced pressure. The residue was dissolved in 56 ml of dioxane, and 5.5 g of di-t-butyl dicarbonate was added thereto, followed by stirring at room temperature for 40 hours. The solvent was evaporated under reduced pressure, and the residue was subjected to silica gel column chromatography using a 1:9 mixture of ethyl acetate and hexane as a developing solvent. The fraction containing the desired compound was concentrated to give 7.61 g of the title compound.

$^1$H-NMR (CDCl$_3$) δ: 1.20–1.30 (m, 1H), 1.53 (s, 9H), 1.54 (d, 3H, J=9 Hz), 1.79–1.82 (m, 1H), 2.50–2.70 (m, 2H), 2.95–3.10 (br, 1H), 3.18 (dd, 1H, J=14 Hz, 3 Hz), 3.25–3.45 (br, 1H), 5.70–5.85 (br, 1H), 6.19 (td, 1H, J=8 Hz, 2 Hz), 6.77 (dd, 1H, J=8 Hz, 7 Hz), 7.30–7.45 (m, 6H).

4) Preparation of 9-Fluoro-3-(1-phenylethyl)-2,3,4,4a,5,6-hexahydro-1-oxopyrazino[1,2-a]quinoline (Diastereomer A)

In 50 ml of tetrahydrofuran was dissolved 7.61 g of the compound obtained in (3) above, and 2.45 ml of pyridine and 1.75 ml of chloroacetyl chloride were added thereto while stirring at 0° C., followed by stirring at room temperature for 30 minutes. Ice-water was added to the reaction mixture, and the mixture was extracted with ethyl acetate. The organic layer was washed with a saturated sodium chloride aqueous solution and dried over anhydrous sodium sulfate. The solvent was removed by evaporation under reduced pressure, and the residue was dissolved in 20 ml of tetrahydrofuran. To the solution was added 25 ml of trifluoroacetic acid, and the solution was stirred at room temperature for 2 hours and then at 50° C. for 1 hour, followed by concentration to dryness under reduced pressure. The residue was dissolved in 50 ml of dimethylformamide, and 4.6 g of potassium carbonate was added thereto, followed by stirring at 50° C. for 1 hour. The reaction mixture was cooled to room temperature, diluted with water, and extracted with ethyl acetate. The organic layer was washed with a saturated sodium chloride aqueous solution and dried over anhydrous sodium sulfate. The solvent was removed by evaporation under reduced pressure, and the residue was subjected to silica gel column chromatography using a 1:9 mixture of ethyl acetate and hexane as a developing solvent. The fraction containing the desired compound was concentrated to afford 5.09 g of the title compound.

$^1$H-NMR (CDCl$_3$) δ: 1.40 (d, 3H, J=7 Hz), 1.75–1.9 (m, 2H), 2.25 (dd, 1H, J=12 Hz, 9 Hz), 2.80 (dd, 1H, J=8 Hz, 5 Hz), 2.96 (ddd, 1H, J=12 Hz, 5 Hz, 2 Hz), 3.07 (d, 1H, J=17 Hz), 3.37 (q, 1H, J=7 Hz), 3.58–3.65 (m, 1H), 3.78 (dd, 1H, J=17 Hz, 2 Hz), 6.77 (td, 1H, J=8 Hz, 2 Hz), 7.03 (dd, 1H, J=8 Hz, 6 Hz), 7.25–7.40 (m, 5H), 7.93 (dd, 1H, J=12 Hz, 2 Hz).

5) Preparation of 9-Fluoro-3-(1-phenylethyl)-2,3,4,4a,5,6-hexahydro-1H-pyrazino[1,2-a]quinoline (Diastereomer A)

In 20 ml of tetrahydrofuran was dissolved 5.9 g of sodium borohydride, and 25.6 ml of a boron trifluoride diethyl ether complex was added thereto. To the resulting diborane solution was added 30 ml of a tetrahydrofuran solution containing 5.09 g of the compound obtained in (4) above, followed by heating under reflux for 2 hours. The reaction mixture was cooled to 0° C., and a 6N hydrochloric acid aqueous solution was added thereto, followed by stirring at 80° C. for 1 hour and then at room temperature for 48 hours. The reaction mixture was neutralized by addition of a saturated sodium hydrogencarbonate aqueous solution and extracted with chloroform. The organic layer was dried over anhydrous sodium sulfate, and the solvent was evaporated under reduced pressure. The resulting residue was subjected to silica gel column chromatography using a 1:9 mixture of ethyl acetate and hexane as a developing solvent. The fraction containing the desired compound was concentrated to afford 2.52 g of the title compound.

$^1$H-NMR (CDCl$_3$) δ: 1.39 (d, 3H, J=6 Hz), 1.56–1.81 (m, 3H), 2.18–2.25 (m, 1H), 2.57–2.63 (m, 1H), 2.70–2.78 (m, 2H), 2.78–2.98 (m, 2H), 3.18 (dd, 1H, J=11 Hz, 3 Hz), 3.35 (q, 1H, J=7 Hz), 3.66 (d, 1H, J=11 Hz), 6.34 (td, 1H, J=8 Hz, 2 Hz), 6.46 (dd, 1H, J=13 Hz, 2 Hz), 6.85 (t, 1H, J=8 Hz), 7.23–7.33 (m, 5 Hz).

6) Preparation of 9-Fluoro-2,3,4,4a,5,6-hexahydro-1H-pyrazino[1,2-a]quinoline (Enantiomer A)

In 40 ml of methanol was dissolved 2.52 g of the compound obtained in (5) above, and 2.54 g of ammonium formate and 2.5 g of 10% palladium-on-carbon were added thereto, followed by heating under reflux for 1.5 hours. Any insoluble matter was removed by filtration, and the filtrate was concentrated under reduced pressure. To the residue was added a saturated sodium chloride aqueous solution, followed by extraction with chloroform. The organic layer was dried over anhydrous sodium sulfate, and the solvent was removed by evaporation under reduced pressure. The residue was subjected to silica gel column chromatography using a 7:10 mixture of methanol and chloroform as a developing solvent. The fraction containing the desired compound was concentrated to afford 1.56 g of the title compound.

$^1$H-NMR (CDCl$_3$) δ: 1.67–1.78 (m, 1H), 1.89–1.96 (m, 1H), 2.63–2.72 (m, 2H), 2.76–2.84 (m, 1H), 2.95–3.04 (m, 2H), 3.13–3.32 (m, 2H), 3.67–3.76 (m, 1H), 6.40 (td, 1H, J=8 Hz, 2 Hz), 6.47 (dd, 1H, J=12 Hz, 2 Hz), 6.90 (t, 1H, t=8 Hz).

7) Preparation of 3-[3-[1-(2-Amino-6-dimethylamino-4-pyrimidinyl)-5-methyl-4-pyrazolyl]-2-trans-propen-1-yl]-9-fluoro-2,3,4,4a,5, 6-hexahydro-1H-pyrazino[1,2-a]quinoline Hydrochloride (Isomer A)

A mixture consisting of 198 mg of the amine obtained in (6) above, 261 mg of the aldehyde obtained in Example 67-(5), and 20 ml of ethanol was stirred at 80° C. for 1 hour. After cooling to room temperature, 0.33 ml of acetic acid was added to the reaction mixture, and 110 mg of sodium cyanoborohydride was added thereto in 3 divided portions every hour. After the reaction mixture was stirred at room temperature for 13 hours, water and a saturated sodium carbonate aqueous solution were added thereto, and the mixture was extracted with chloroform. The organic layer was dried over an anhydrous sodium sulfate, and the solvent was removed by evaporation under reduced pressure. The resulting residue was subjected to silica gel column chromatography using a 2:98 mixture of methanol and chloroform as a developing solvent. The fraction containing the desired compound was concentrated. The residue weighing 166 mg was dissolved in 10 ml of isopropyl alcohol under heating, and 0.45 ml of a 1N ethanolic solution of hydrochloric acid was added thereto while hot. The reaction mixture was allowed to stand at room temperature for 10 hours, and the precipitate formed was collected by filtration to afford 120 mg of the title compound.

Melting point: 208° C. or higher (with decomposition)

$^1$H-NMR (DMSO-d$_6$) δ: 1.55–1.70 (m, 1H), 1.95–2.05 (m, 1H), 2.67 (s, 3H), 2.60–3.00 (m, 3H), 3.00–3.20 (m, 2H), 3.19 (s, 6H), 3.30–3.70 (m, 4H), 3.80–4.00 (m, 1H), 4.11 (d, 1H, J=13 Hz), 6.26 (dt, 1H, J=16 Hz, 7 Hz), 6.41 (s, 1H), 6.47 (td, 1H, J=8 Hz, 2 Hz), 6.76 (dd, 1H, J=13 Hz, 2 Hz), 6.81 (d, 1H, J=16 Hz), 6.98 (t, 1H, J=8 Hz), 8.15 (s, 1H), 11.10–11.25 (br, 1H).

EXAMPLE 70

Synthesis of 3-[3-(1-(2-Amino-6-dimethylamino)-4-pyrimidin-yl)-5-methyl-4-pyrazolyl)-2-trans-propen-1-yl]-9-fluoro-2,3,4,4a,5,6-hexahydro-1H-pyrazino[1,2-a]quinoline (Isomer B)

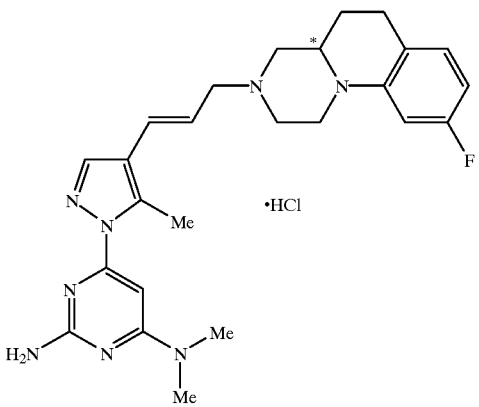

1) Preparation of 7-Fluoro-2-[N-(1-phenylethyl)-N-t-butoxycarbonylaminomethyl]-1,2,3,4-tetrahydroquinoline (Diastereomer B)

The diastereomer B obtained in Example 69-(2) (5.17 g) was allowed to react and worked up in the same manner as in Example 69-(3) to give 6.93 g of the title compound.

$^1$H-NMR (CDCl$_3$) δ: 1.30–1.60 (m, 1H), 1.47 (s, 9H), 1.54 (d, 3H, J=9 Hz), 2.50–2.55 (m, 2H), 3.00–3.20 (m, 3H), 5.25–5.45 (br, 1H), 6.10 (dd, 1H, J=11 Hz, 2 Hz), 6.23 (td, 1H, J=8 Hz, 2 Hz), 6.78 (dd, 1H, J=8 Hz, 7 Hz), 7.20–7.40 (m, 5H).

2) Preparation of 9-Fluoro-3-(1-phenylethyl)-2,3,4, 4a,5,6-hexahydro-1-oxopyrazino[1,2-a]quinoline (Diastereomer B)

The compound obtained in (1) above weighing 6.93 g was allowed to react and worked up in the same manner as in Example 69-(4) to give 5.28 g of the title compound.

$^1$H-NMR (CDCl$_3$) δ: 1.41 d, 3H, J=7 Hz), 1.83–1.90 (m, 2H), 2.02–2.15 (m, 1H), 2.50 (dd, 1H, J=12 Hz, 6 Hz), 2.79–2.94 (m, 2H), 3.33 (s, 2H), 3.42 (q, 1H, J=6 Hz), 3.50–3.62 (m, 1H), 6.78 (td, 1H, J=8 Hz, 2 Hz), 7.04 (dd, 1H, J=8 Hz, 7 Hz), 7.26–7.40 (m, 5H), 7.81 (dd, 1H, J=12 Hz, 2 Hz).

3) Preparation of 9-Fluoro-3-(1-phenylethyl)-2,3,4, 4a,5,6-hexahydro-1H-pyrazino[1,2-a]quinoline (Diastereomer B)

The compound obtained in (2) above weighing 5.28 g was allowed to react and worked up in the same manner as in Example 69-(5) to yield 2.45 g of the title compound.

$^1$H-NMR (CDCl$_3$) δ: 1.39 (d, 3H, J=6 Hz), 1.68–1.80 (m, 1H), 1.86–2.13 (m, 3H), 2.63–2.70 (m, 1H), 2.74–2.85 (m, 2H), 3.04–3.12 (m, 2H), 3.35–3.40 (m, 1H), 3.48–3.53 (m, 1H), 6.34 (td, 1H, J=8 Hz, 2 Hz), 6.40 (dd, 1H, J=13 Hz, 2 Hz), 6.87 (t, 1H, J=8 Hz), 7.24–7.33 (m, 5 Hz).

4) Preparation of 9-Fluoro-2,3,4,4a,5,6-hexahydro-1H-pyrazino[1,2-a]quinoline (Enantiomer B)

The compound obtained in (3) above weighing 2.45 g was allowed to react and worked up in the same manner as in Example 69-(6) to yield 1.57 g of the titled compound.

The $^1$H-NMR data of the product were in complete agreement with those of the compound obtained in Example 69-(6).

5) Preparation of 3-[3-[1-(2-Amino-6-dimethylamino-4-pyrimidinyl)-5-methyl-4-pyrazolyl]-2-trans-propen-1-yl]-9-fluoro-2,3,4,4a,5,6-hexahydro-1H-pyrazino[1,2-a]quinoline Hydrochloride (Isomer B)

The amine obtained in (4) above (210 mg) arid the aldehyde obtained in Example 67-(5) (277 mg) were allowed to react and worked up in the same manner as in Example 69- (7) to afford 140 mg of the title compound.

Melting point: 205° C. or higher (with decomposition)

The $^1$H-NMR data of the resulting compound were in complete agreement with those of the compound obtained in Example 69.

EXAMPLE 71

Synthesis of (+/−)-3-[3-[1-(2-Amino-6-dimethylamino-4-pyrimidinyl)-5-methyl-4-pyrazolyl]-2-trans-propen-1-yl]-9-fluoro-2,3,4,4a,5,6-hexahydro-1H-pyrazino[2,1-c]-1,4-benzoxazine Hydrochloride

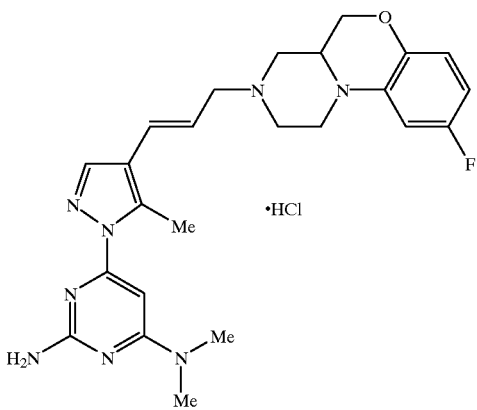

1) Preparation of 1-(4-Fluoro-2-nitrophenoxy)-2,3-epoxypropane

A mixture consisting of 31.4 g of 4-fluoro-2-nitrophenol, 100 ml of epichlorohydrin, 9.1 g of sodium hydroxide, 40 ml of water, and 900 ml of ethanol was stirred at 80° C. for 10 hours. The reaction mixture was cooled to room temperature, and any insoluble matter was removed by filtration. The filtrate was concentrated to dryness under reduced pressure. The residue was dissolved in a 1:1 mixed solvent of diethyl ether and hexane, washed with water and then with a saturated sodium chloride aqueous solution, and dried over anhydrous sodium sulfate. The solvent was evaporated under reduced pressure. The residue was subjected to silica gel column chromatography using a 3:1 mixture of chloroform and hexane as a developing solvent. The fraction containing the desired compound was concentrated to give 27.9 g of the title compound.

$^1$H-NMR (CDCl$_3$) δ: 2.84 (dd, 1H, J=5 Hz, 2 Hz), 2.93 (t, 1H, J=5 Hz), 3.36–3.40 (m, 1H), 4.10 (dd, 1H, J=11 Hz, 5 Hz), 4.41 (dd, 1H, J=11 Hz, 3 Hz), 7.14 (dd, 1H, J=9 Hz, 4 Hz), 7.24–7.30 (m, 1H), 7.60 (dd, 1H, J=8 Hz, 3 Hz).

2) Preparation of 1-(4-Fluoro-2-nitrophenoxy)-2-hydroxy-3-phthalimidopropane

A mixture consisting of 4.49 g of the compound obtained in (1) above, 3.10 g of phthalimide, 0.21 ml of pyridine, and 20 ml of butanol was heat-refluxed for 16 hours, and the solvent was removed by evaporation under reduced pressure. The residue was subjected to silica gel column chromatography using a 2:98 mixture of methanol and chloroform as a developing solvent. The fraction containing the desired compound was concentrated to furnish 3.90 g of the title compound.

$^1$H-NMR (CDCl$_3$) δ: 3.07 (d, 1H, J=6 Hz), 3.99 (dd, 1H, J=14 Hz, 5 Hz), 4.03 (dd, 1H, J=14 Hz, 6 Hz), 4.14 (dd, 1H, J=9 Hz, 5 Hz), 4.22 (dd, 1H, J=9 Hz, 4 Hz), 4.30–4.40 (m, 1H), 7.10 (dd, 1H, J=9 Hz, 4 Hz), 7.25–7.31 (m, 1H), 7.65 (dd, 1H, J=8 Hz, 3 Hz), 7.74 (2H, dd, J=5 Hz, 3 Hz), 7.87 (dd, 2H, J=5 Hz, 3 Hz).

3) Preparation of 6-Fluoro-3-phthalimidomethyl-1,4-benzoxazine

In 12 ml of acetone was dissolved 3.85 g of the compound obtained in (2) above, and 10 ml of a Jone's reagent (prepared from 4 g of chromic acid, 2 ml of concentrated sulfuric acid, and 8 ml of water) was added thereto while keeping the inner temperature between 15° C. and 20° C., followed by stirring at room temperature for 3 hours. The reaction mixture was diluted with water and filtered to collect the insoluble matter. The resulting compound was dissolved in 200 ml of ethanol and subjected to catalytic hydrogenation in the presence of Raney nickel for 24 hours. The insoluble matter was removed by filtration, and the filtrate was concentrated to dryness. The resulting crystalline residue was dissolved in 50 ml of ethanol under heating, followed by cooling to room temperature. To the reaction mixture were added 6.1 ml of acetic acid and 1.3 g of sodium cyanoborohydride, followed by stirring for 1 hour. Water and a saturated sodium hydrogencarbonate aqueous solution were added to the reaction mixture, and the mixture was extracted with chloroform. The organic layer was washed with a saturated sodium chloride aqueous solution and dried over anhydrous sodium sulfate. The solvent was evaporated under reduced pressure. The residue was subjected to silica gel column chromatography and developed with chloroform. The fraction containing the desired compound was concentrated to afford 1.79 g of the title compound.

$^1$H-NMR (CDCl$_3$) δ: 3.75–3.97 (m, 4H), 4.19–4.24 (m, 2H), 6.27–6.32 (m, 1H), 6.66–6.70 (m, 1H), 7.75 (dd, 2H, J=5 Hz, 3 Hz), 7.87 (dd, 2H, J=5 Hz, 3 Hz).

4) Preparation of 3-Aminomethyl-6-fluoro-1,4-benzoxazine

In 40 ml of ethanol was dissolved 1.79 g of the compound obtained in (3) above, and 0.9 ml of hydrazine monohydrate was added thereto, followed by heating under reflux for 3 hours. The solvent was evaporated off, and the residue was dissolved in water. To the solution was added 6 ml of acetic acid, and the mixture was stirred at room temperature for 30 minutes and then at 0° C. for 30 minutes. Any insoluble matter was removed by filtration, and the filtrate was rendered alkaline with a 10% sodium hydroxide aqueous solution and extracted with chloroform. The organic layer was dried over anhydrous sodium sulfate, and the solvent was removed by evaporation under reduced pressure to give 972 mg of the title compound.

$^1$H-NMR (CDCl$_3$) δ: 2.70 (dd, 1H, J=12 Hz, 8 Hz), 2.92 (dd, 1H, J=12 Hz, 5 Hz), 3.30 (m, 1H), 3.93 (dd, 1H, J=11 Hz, 7 Hz), 4.17 (dd, 1H, J=11 Hz, 4 Hz), 4.35 (brs, 1H), 6.28–6.35 (m, 2H), 6.68 (dd, 1H, J=8 Hz, 5 Hz).

5) Preparation of 3-Benzylaminomethyl-6-fluoro-1,4-benzoxazine

In 30 ml of ethanol were dissolved 972 mg of the compound obtained in (4) above and 553 mg of benzaldehyde. The solution was stirred at 50° C. for 1 hour, followed by concentration to dryness. The residue was dissolved in 30 ml of ethanol, 1.53 ml of acetic acid was added thereto, and 1.0 g of sodium cyanoborohydride was further added thereto, followed by stirring at room temperature for 2 hours. The reaction mixture was concentrated, and a 1N sodium hydroxide aqueous solution was added to the residue. The mixture was extracted with chloroform. The organic layer was dried over anhydrous sodium sulfate. The solvent was removed by evaporation under reduced pressure. The residue was subjected to silica gel column chromatography using a 2:98 mixture of methanol and chloroform as a developing solvent. The fraction containing the desired product was concentrated to afford 1.03 g of the title compound.

$^1$H-NMR (CDCl$_3$) δ: 2.61 (dd, 1H, J=12 Hz, 9 Hz), 2.80 (dd, 1H, J=12 Hz, 4 Hz), 3.40–3.48 (m, 1H), 3.80, 3.81 (ABq, 2H, J=13 Hz), 3.87 (dd, 1H, J=10 Hz, 7 Hz), 4.16 (ddd, J=10 Hz, 3 Hz, 1 Hz), 4.41 (brs, 1H), 6.25–6.32 (m, 2H), 6.64–6.70 (m, 1H), 6.64–6.70 (m, 1H), 7.20–7.36 (m, 5H).

6) Preparation of 3-Benzyl-1,2-dioxo-9-fluoro-2,3,4,4a,5,6-hexahydro-1H-pyrazino[2,1-c]-1,4-benzoxazine To 1.02 g of the compound obtained in (5) above was added 2 ml of diethyl oxalate, and the mixture was heated at 110° C. for 11 hours and then at 150° C. for 3 hours. The reaction mixture was concentrated under reduced pressure, and the residue was recrystallized from diethyl ether to give 777 mg of the title compound as a pale pink powder.

$^1$H-NMR (CDCl$_3$) δ: 3.28 (dd, 1H, J=4 Hz, 13 Hz), 3.45 (t, 1H, J=13 Hz), 3.82 (dd, 1H, J=10 Hz, 11 Hz), 4.24 (dd, 1H, J=3 Hz, 11 Hz), 4.29–4.37 (m, 1H), 4.64, 4.81 (ABq, 2H, J=15 Hz), 6.77 (ddd, 1H, J=3 Hz, 7 Hz, 9 Hz), 6.86 (dd, 1H, J=6 Hz, 9 Hz), 7.29–7.39 (m, 5H), 8.63 (dd, 1H, J=3 Hz, 12 Hz).

7) Preparation of 3-Benzyl-9-fluoro-2,3,4,4a,5,6-hexahydro-1H-pyrazino[2,1-c]-1,4-benzoxazine In 15 ml of tetrahydrofuran was suspended 942 mg of sodium borohydride, and a boron trifluoride diethyl ether complex was added thereto dropwise at room temperature, followed by stirring for 1 hour. To the reaction mixture was added 677 mg of the compound obtained in (6) above in several divided portions, and the mixture was heated under reflux for 2 hours. The reaction mixture was poured into 60 ml of concentrated hydrochloric acid under cooling with ice in small portions, followed by stirring overnight. A saturated sodium hydrogencarbonate aqueous solution was added to the reaction mixture to make it alkaline, followed by extraction with chloroform. The organic layer was washed with a saturated sodium chloride aqueous solution and dried over anhydrous sodium sulfate. The solvent was evaporated, and the residue was subjected to silica gel column chromatography using a mixed solvent of ethyl acetate and hexane in a mixing ratio varying from 1:6 to 1:5. The fraction containing the desired product was concentrated to give 575 mg of the title compound as a colorless oily substance.

$^1$H-NMR (CDCl$_3$) δ: 1.82 (t, 1H, J=11 Hz), 2.28 (dt, 1H, J=4 Hz, 12 Hz), 2.79–2.89 (m, 2H), 2.95–2.98 (m, 2H), 3.18–3.20 (m, 2H), 3.52–3.54 (m, 1H), 3.51, 3.59 (ABq, 2H, J=13 Hz), 3.92 (dd, 1H, J=9 Hz, 11 Hz), 4.10 (dd, 1H, J=3 Hz, 11 Hz), 6.36 (dt, 1H, J=3 Hz, 9 Hz), 6.47 (dd, 1H, J=3 Hz, 11 Hz), 6.66 (dd, 1H, J=5 Hz, 9 Hz), 7.33–7.34 (m, 5H).

8) Preparation of 9-Fluoro-2,3,4,4a,5,6-hexahydro-1H-pyrazino[2,1-c]-1,4-benzoxazine In 20 ml of methanol was dissolved 575 mg of the compound obtained in (7) above, and 608 mg of ammonium formate and 580 mg of 10% palladium-on-carbon were added thereto, followed by heating under reflux for 1 hour. The insoluble matter was separated by filtration, and the solvent was removed by evaporation. To the residue was added a saturated sodium chloride aqueous solution, and the mixture was extracted with chloroform. The extract was dried over anhydrous sodium sulfate, and the solvent was removed by evaporation to yield 369 mg of the title compound as a colorless oily substance.

$^1$H-NMR (CDCl$_3$) δ: 2.48 (dd, 1H, J=11 Hz, 12 Hz), 2.70 (dt, 1H, J=3 Hz, 12 Hz), 2.88–3.00 (m, 2H), 3.05–3.15 (m, 2H), 3.51 (ddd, 1H, J=2 Hz, 3 Hz, 12 Hz), 3.92 (dd, 1H, J=9 Hz, 11 Hz), 4.13 (dd, 1H, J=3 Hz, 11 Hz), 6.37 (ddd, 1H, J=3 Hz, 8 Hz, 9 Hz), 6.47 (dd, 1H, J=3 Hz, 11 Hz), 6.66 (dd, 1H, J=5 Hz, 9 Hz).

9) Preparation of (+/−)-3-[3-[1-(2-Amino-6-dimethylamino-4-pyrimidinyl)-5-methyl-4-pyrazolyl]-2-trans-propen-1-yl]-9-fluoro-2,3,4,4a,5,6-hexahydro-1H-pyrazino[2,1-c]-1,4-benzoxazine Hydrochloride The amine obtained in (8) above (175 mg) and the aldehyde obtained in Example 67-(5) (229 mg) were allowed to react and worked up in the same manner as in Example 69-(7) to yield 238 mg of the title compound.

Melting point: 197–208° C.

$^1$H-NMR (DMSO-d$_6$) δ: 2.66 (s, 3H), 2.83–2.85 (m, 1H), 3.09–3.28 (m, 2H), 3.19 (s, 6H), 3.55 (d, 2H, J=11 Hz), 3.63–3.68 (m, 1H), 3.80–4.00 (m, 3H), 4.09 (d, 1H, J=13 Hz), 4.30 (dd, 1H, J=3 Hz, 11 Hz), 6.24 (dt, 1H, J=8 Hz, 16 Hz), 6.42 (d, 1H, J=7 Hz), 6.50 (dt, 1H, J=3 Hz, 9 Hz), 6.75 (dd, J=6 Hz, 9 Hz), 6.81 (d, 1H, J=16 Hz), 6.88 (dd, 1H, J=3 Hz, 12 Hz), 8.14 (s, 1H), 11.69 (brs, 1H).

EXAMPLE 72

Synthesis of (+/−)-2-[3-[1-(2-Amino-6-dimethylamino-4-pyrimidinyl)-5-methyl-4-pyrazolyl]-2-trans-propen-1-yl]-1,2,3,4,10,10a-hexahydropyrazino[1,2-a]indole Hydrochloride

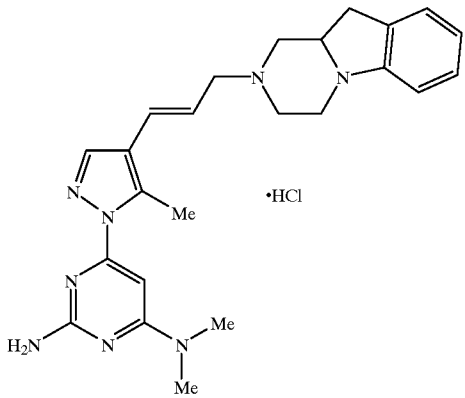

(+/−)-1,2,3,4,10,10a-Hexahydropyrazino[1,2-a]indole (50 mg) and the aldehyde obtained in Example 67-(5) (38 mg) were allowed to react and worked up in the same manner as in Example 69-(7) to give 30 mg of the title compound.

Melting point: 200–204° C. (with decomposition)

$^1$H-NMR (DMSO-d$_6$) δ: 2.5–2.6 (m, 1H), 2.65 (s, 3H), 2.9–3.0 (m, 1H), 3.07 (s, 6H), 3.3–3.6 (m, 5H), 3.8–4.0 (m, 4H), 6.16 (dt, 1H, J=16 Hz, 7 Hz), 6.29 (s, 1H), 6.65 (d, 1H, J=7 Hz), 6.67 (t, 1H, J=7 Hz), 6.75 (d, 1H, J=16 Hz), 7.07 (t, 1H, J=7 Hz), 7.12 (d, 1H, J=7 Hz), 8.00 (s, 1H), 11.1–11.0 (m, 1H).

Industrial Applicability

The pyrazole derivatives of the present invention provide an antitumor activity and are useful as an antitumor agent for treating various tumors.

What is claimed is:

1. A compound represented by formula (I) or a salt thereof:

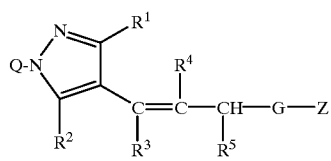

(I)

wherein

R$^1$ and R$^2$, which may be the same or different, each represent a hydrogen atom, a halogen atom, a hydroxy group, an alkoxy group, an amino group, an alkylamino group, an aryl group or an alkyl group, in which the alkyl group may be substituted with a halogen atom, an amino group, an alkylamino group, a hydroxy group, an alkoxy group, a thiol group or an alkylthio group;

R$^3$ and R$^4$, which may be the same or different, each represent a hydrogen atom, a halogen atom, an alkoxy group, an amino group, an alkylamino group, an aryl group or an alkyl group, in which the alkyl group may be substituted with a halogen atom, an amino group, an alkylamino group, a hydroxy group, an alkoxy group, a thiol group or an alkylthio group;

R$^5$ represents a hydrogen atom, an alkyl group, an alkenyl group, an alkynyl group, an aryl group or an arylalkyl group, in which the alkyl group may be substituted with a halogen atom, an amino group, an alkylamino group, a hydroxy group, an alkoxy group, a thiol group or an alkylthio group;

Q represents an amidino group, a cycloalkyl group, a phenyl group or a monocyclic heterocyclic group except a pyrimidinyl group bonded to the N atom at its 2-position, and the cycloalkyl, phenyl or monocyclic heterocyclic group may have one or more substituents selected from the group consisting of an alkyl group, an alkyl group substituted with a halogen atom, an amino group, an alkylamino group, a hydroxy group, an alkoxy group, a thiol group or an alkylthio group, a halogen atom, a hydroxy group, an alkoxy group, an alkoxyalkoxy group, an amino group, an alkylamino group, an acylamino group, an alkylaminoalkylamino group, a nitro group, a cyano group, a carbamoyl group, a thiol group, an alkylthio group, an arylthio group, an alkylsulfinyl group, an arylsulfinyl group, an alkylsulfonyl group, an arylsulfonyl group, an aminosulfonyl group, an alkylaminosulfonyl group, an arylaminosulfonyl group, and an aryl group;

G represents a nitrogen-containing saturated heterocyclic structure represented by formula:

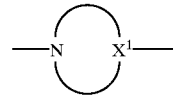

wherein

X$^1$ represents a nitrogen atom, in which the ring may have a keto group and may have one or more substituents selected from the group consisting of an alkyl group, an alkyl group substituted with a halogen atom, an amino group, an alkylamino group, a hydroxy group, an alkoxy group, a thiol group or an alkylthio group, a halogen atom, a hydroxy group, an alkoxy group, an amino group, an alkylamino group, and an aryl group;

Z represents a phenyl group, a heterocyclic group or a phenyl or heterocyclic group having one or more substituents selected from the group consisting of an alkyl group, an alkyl group substituted with a halogen atom, an amino group, an alkylamino group, a hydroxy group, an alkoxy group, a thiol group or an alkylthio group, a halogen atom, a hydroxy group, an alkoxy group, a thiol group, an alkylthio group, an amino group, an alkylamino group, an acylamino group, a nitro group, a cyano group, a carbamoyl group, and an aryl group.

2. The compound according to claim 1 or a salt thereof, wherein G is a group derived from piperazine.

3. The compound according to claim 1 or a salt thereof; wherein Q is a monocyclic heterocyclic group.

4. The compound according to claim 1 or a salt thereof, wherein Z is a phenyl group having one or more substituents selected from the group consisting of an alkyl group, an alkyl group substituted with a halogen atom, an amino group, an alkylamino group, a hydroxy group, an alkoxy group, a thiol group or an alkylthio group, a halogen atom, a hydroxy group, an alkoxy group, a thiol group, an alkylthio group, an amino group, an alkylamino group, an acylamino group, a nitro group, a cyano group, a carbamoyl group, and an aryl group.

5. The compound according to claim 1 or a salt thereof, wherein Z is a phenyl group having one or two substituents selected from the group consisting of a halogen atom, a hydroxy group, a cyano group, an alkyl group, and an alkyl group substituted with a halogen atom, an amino group, an alkylamino group, a hydroxy group, an alkoxy group, a thiol group or an alkylthio group.

6. An antitumor agent containing the compound as defined in claim 1 or a salt thereof as an active ingredient.

7. The compound according to claim 1 or a salt thereof, wherein the compound is 1-[1-(4,6-diamino-1,3,5-triazin-2-yl)-5-methyl-4-pyrazolyl]-3-[4-(3,5-difluoro-phenyl)-1-piperazinyl]-1-trans-propene hydrochloride.

* * * * *